United States Patent [19]
Croteau et al.

[11] Patent Number: 6,043,072
[45] Date of Patent: Mar. 28, 2000

[54] NUCLEIC ACIDS ENCODING TAXUS GERANYLGERANYL DIPHOSPHATE SYNTHASE, AND METHODS OF USE

[75] Inventors: Rodney B. Croteau, Pullman; Jerry L. Hefner, Seattle, both of Wash.

[73] Assignee: Washington State University Research Foundation, Pullman, Wash.

[21] Appl. No.: 09/187,050

[22] Filed: Nov. 5, 1998

[51] Int. Cl.[7] .............................. C12N 9/10; C12N 1/20; C12N 15/00; C07H 21/04; C07K 1/00
[52] U.S. Cl. .................. 435/193; 435/252.3; 435/320.1; 435/419; 536/23.2; 536/23.6; 530/350
[58] Field of Search ................................. 435/193, 252.3, 435/320.1, 419; 536/23.2, 23.6; 530/350

[56] References Cited

PUBLICATIONS

Zhu, X.F., Suzuki, K., Okada, K., Tanaka, K., Nakagawa, T., Kawamukai, M. and Matsuda, H. (1997) *Plant Cell Physiol.*, 38:357–361.
Scolnik, P.A. and Bartley, G.E. (1995) *Plant Physiol.*, 108:1343.
Kuntz, M., Römer, S., Suire, C., Hugueney, P., Weil, J.H., Schantz, R. and Camara, B. (1992) *Plant J.*, 2:25–34.
Bantignies, B., Liboz, T. and Ambid, C. (1996) *Plant Physiol.*, 110:336.
Aitken, S.M., Attucci, S., Ibrahim, R.K. and Gulick, P.J. (1995) *Plant Physiol.*, 108:837–838.
Bonk, M., Hoffman, B., Von Lintig, J., Schledz, M., Al–Babili, S., Hobeika, E., Kleinig, H. and Beyer, P. (1997) *Eur. J. Biochem.*, 247:942–950.
Zhu, X.F., Suzuki, K., Saito, T., Okada, K., Tanaka, K., Nakagawa, T., Matsuda, H. and Kawamukai, M. (1997) *Plant Mol. Biol.*, 35:331–341.

*Primary Examiner*—Ponnathapu Achutamurthy
*Assistant Examiner*—Tekchand Saidha
*Attorney, Agent, or Firm*—Christensen O'Connor Johnson & Kindness PLLC

[57] ABSTRACT

A cDNA encoding geranylgeranyl diphosphate synthase from Canadian Yew (*Taxus canadensis*) has been isolated and sequenced, and the corresponding amino acid sequence has been determined. Accordingly, an isolated DNA sequence (SEQ ID NO:1) is provided which codes for the expression of geranylgeranyl diphosphate synthase (SEQ ID NO:2), from Canadian Yew (*Taxus canadensis*). In other aspects, replicable recombinant cloning vehicles are provided which code for geranylgeranyl diphosphate synthase, or for a base sequence sufficiently complementary to at least a portion of geranylgeranyl diphosphate synthase DNA or RNA to enable hybridization therewith. In yet other aspects, modified host cells are provided that have been transformed, transfected, infected and/or injected with a recombinant cloning vehicle and/or DNA sequence encoding geranylgeranyl diphosphate synthase. Thus, systems and methods are provided for the recombinant expression of the aforementioned recombinant geranylgeranyl diphosphate synthase that may be used to facilitate its production, isolation and purification in significant amounts. Recombinant geranylgeranyl diphosphate synthase may be used to obtain expression or enhanced expression of geranylgeranyl diphosphate synthase in plants in order to enhance the production of geranylgeranyl diphosphate, or diterpenes derived therefrom, or may be otherwise employed for the regulation or expression of geranylgeranyl diphosphate synthase, or the production of its products.

13 Claims, 5 Drawing Sheets

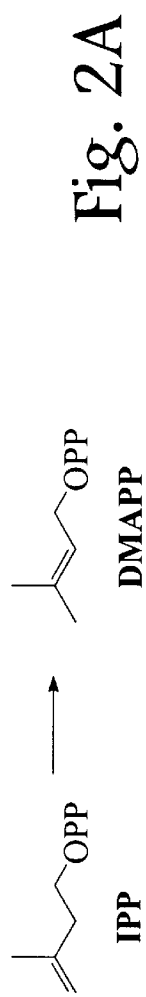
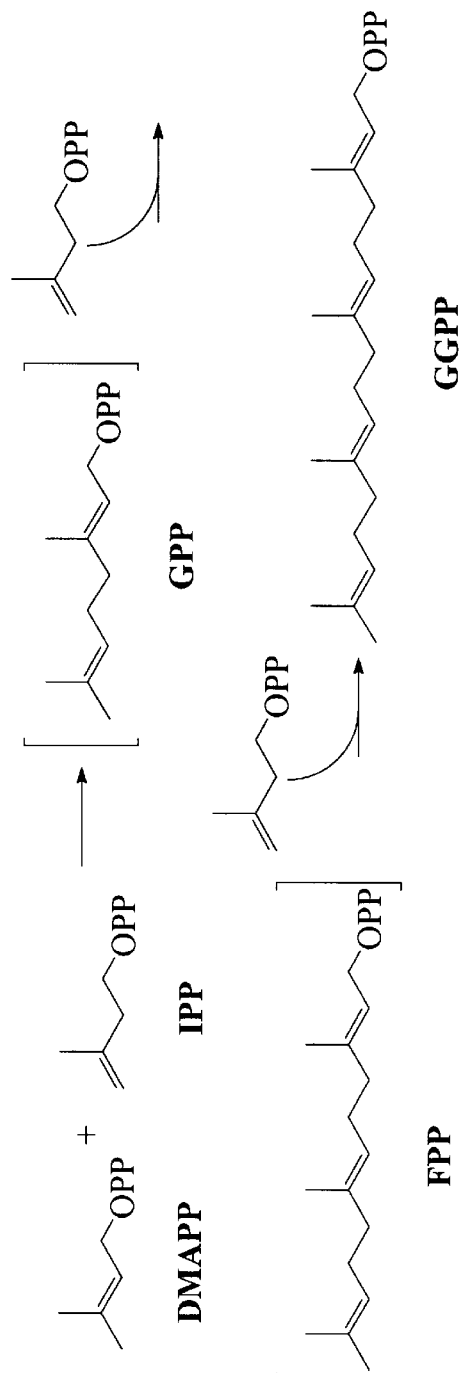
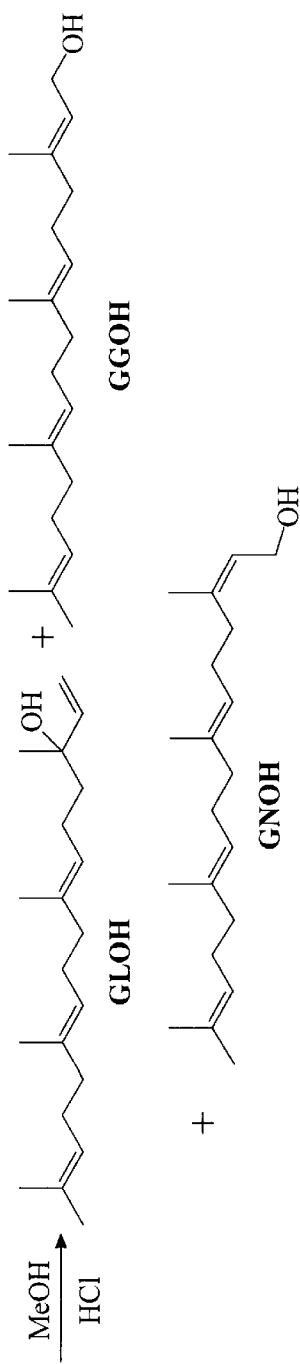
Fig. 2A
Fig. 2B
Fig. 2C

NUCLEIC ACIDS ENCODING TAXUS GERANYLGERANYL DIPHOSPHATE SYNTHASE, AND METHODS OF USE

This invention was funded in part by grant CA-55254 from the National Institutes of Health, and by National Institutes of Health Traineeship (T32GM08336). The government has certain rights in this invention.

FIELD OF THE INVENTION

This invention relates to nucleic acid sequences encoding geranylgeranyl diphosphate synthase, in particular to nucleic acid sequences encoding geranylgeranyl diphosphate synthase from yew.

BACKGROUND OF THE INVENTION

The diterpenoid anti-cancer drug paclitaxel and related taxanes accumulate in resin cells of Taxus (yew) stem, needle and root tissue (Croom, E. M., Jr. (1995) in *Taxol: Science and Applications* (Suffness, M., Ed.), pp. 37–70, CRC Press, Boca Raton, Fla.), and in cell cultures of yew (Ketchum, R. E. B. and Gibson, D. M. (1996) *Plant Cell Tiss. Org. Cult.*, 46:9–16; Christen, A. A. et al (1989) *Proc. Am. Assoc. Cancer Res.*, 30:566 [See also U.S. Pat. No. 5,019,504]) in which production is induced by methyl jasmonate (Yukimune, Y., Tabata, H., Higashi, M. and Hara, Y. (1996) *Nature Biotech.*, 14:1129–1132; Ketchum, R. E. B., Gibson, D. M., Croteau, R. B. and Shuler, M. L. (1998) *Biotech. Bioeng.*, in press). Paclitaxel has been approved for treatment of refractory ovarian and metastatic breast cancer and, more recently, for small cell lung cancer (Rose, W. C. (1995) in Taxol: Science and Applications (Suffness, M., Ed.), pp. 209–236, CRC Press, Boca Raton, Fla.), and ongoing clinical trials suggest expanded applications in cancer chemotherapy, both in treatment of additional cancer types and in use much earlier in the course of intervention (Holmes, F. A., Kudelka, A. P., Kavanagh, J. J., Huber, M. H., Ajani, J. A. and Valero, V. (1995) in Taxane Anticancer Agents: Basic Science and Current Status (Georg, G. I., Chen, T. T., Ojima, I. and Vyas, D. M., Eds.), pp. 31–57, American Chemical Society, Washington, D.C.). The supply and cost of the drug therefore remain important issues (Suffness, M. (1995) in Taxane Anticancer Agents: Basic Science and Current Status (Georg, G. I., Chen, T. T., Ojima, I. and Vyas, D. M., Eds.), pp. 1–17, American Chemical Society, Washington, D.C.).

Paclitaxel has been prepared by total synthesis (Nicolaou, K. C., Yang, Z., Liu, J. J., Ueno, H., Nantermet, P. G., Guy, R. K., Claiborne, C. F., Renaud, J., Couladouros, E. A., Paulvannin, K. and Sorensen, E. J. (1994) *Nature*, 367:630–634; Holton, R. A., Kim, H. B., Somoza, C., Liang, F., Biediger, R. J., Boatman, P. D., Shindo, M., Smith, C. C., Kim, S., Nadizadeh, H., Suzuki, Y., Tao, C., Vu, P., Tang, S., Zhang, P., Murthi, K. K., Gentile, L. N. and Liu, J. H. (1994) *J. Am. Chem. Soc.*, 116:1599–1600; Masters, J. J., Link, J. T., Snyder, L. B., Young, W. B. and Danishefsky, S. J. (1995) *Angew. Chem. Int. Ed. Engl.*, 34:1723–1726.); however, the synthetic routes are long, expensive, and too low yielding to be commercially useful (Borman, S. (1994) *Chem. Eng. News*, 72:32–34), and it is clear that, for the foreseeable future, the supply of this drug must continue to rely on biological methods of production (Suffness, M. (1995) in Taxane Anticancer Agents: Basic Science and Current Status (Georg, G. I., Chen, T. T., Ojima, I. and Vyas, D. M., Eds.), pp. 1–17, American Chemical Society, Washington, D.C.). It is therefore essential to understand the biosynthesis of paclitaxel, particularly the rate-limiting steps of the pathway, since the manipulation of these slow steps can be expected to lead to improved yield and to the production of the drug in large quantities at reasonable cost.

Paclitaxel is formed by the cyclization of the universal diterpenoid precursor geranylgeranyl diphosphate (West, C. A., Dudley, M. W. and Dueber, M. T. (1979) *Recent Adv. Phytochem.*, 13:163–198; West, C. A. (1981) in Biosynthesis of Isoprenoid Compounds (Porter, J. W. and Spurgeon, S. L., Eds.), Vol. 1, pp. 375–411, Wiley, New York, N.Y.; Gershenzon, J. and Croteau, R. (1993) in Lipid Metabolism in Plants (Moore, T. S., Jr., Ed.), pp. 339–388, CRC Press, Boca Raton, Fla.) to taxa-4(5),11(12)-diene (Koepp, A. E., Hezari, M., Zajicek, J., Stofer Vogel, B., LaFever, R. E., Lewis, N. G. and Croteau, R. (1995) *J. Biol. Chem.*, 270:8686–8690) to establish the taxane skeleton, which then undergoes extensive oxidative modification and addition of side chains (Hezari, M. and Croteau, R. (1997) *Planta Med.*, 63:291–295) (FIG. 1). The properties and mechanism of taxadiene synthase have been examined in some detail (Hezari, M., Lewis, N. G. and Croteau, R. (1995) *Arch. Biochem. Biophys.*, 322:437–444; Lin, X., Hezari, M., Koepp, A. E., Floss, H. G. and Croteau, R. (1996) *Biochemistry*, 35:2968–2977), the corresponding cDNA has been cloned (Wildung, M. R. and Croteau, R. (1996) *J. Biol. Chem.*, 271:9201–9204), and several of the subsequent cytochrome P450-catalyzed hydroxylations (Hezari, M. and Croteau, R. (1997) *Planta Med.*, 63:291–295; Hefner, J., Rubenstein, S. M., Ketchum, R. E. B., Gibson, D. M., Williams, R. M. and Croteau, R. (1996) *Chem. Biol.*, 3:479–489) and acylation steps (Zocher, R., Weckwerth, W., Hacker, C., Kammer, B., Hornbogen, T. and Ewald, D. (1996) *Biochem. Biophys. Res. Commun.*, 229:16–20) of the pathway have been demonstrated.

Genes encoding GGPP synthase are of interest because this branch point prenyltransferase (West, C. A., Dudley, M. W. and Dueber, M. T. (1979) *Recent Adv. Phytochem.*, 13:163–198; West, C. A. (1981) in Biosynthesis of Isoprenoid Compounds (Porter, J. W. and Spurgeon, S. L., Eds.), Vol. 1, pp. 375–411, Wiley, New York, N.Y.; Gershenzon, J. and Croteau, R. (1993) in Lipid Metabolism in Plants (Moore, T. S., Jr., Ed.), pp. 339–388, CRC Press, Boca Raton, Fla.) provides the substrate for protein prenylation (Rilling, H. C., Breunger, E., Epstein, W. W. and Crain, P. F. (1989) *Science*, 247:318–320; Clarke, S. (1992) *Annu. Rev. Biochem.*, 61:355–386.), the formation of the phytol moiety of chlorophylls (Kleinig, H. (1989) *Annu. Rev. Plant Physiol. Plant Mol. Biol.*, 40:39–59), side-chain syntheses of prenylated quinones and tocopherols (Schultz, G., Soll, J., Fiedler, E. and Schulze-Siebert, D. (1985) *Physiol. Plant.*, 64:123–129), the production of carotenoid pigments (Chappell, J. (1995) *Plant Physiol.*, 107:1–6; Bonk, M., Hoffman, B., Von Lintig, J., Schledz, M., Al-Babili, S., Hobeika, E., Kleinig, H. and Beyer, P. (1997) *Eur. J. Biochem.*, 247:942–950; Bartley, G. E. and Scolnik, P. A. (1994) *Annu. Rev. Plant Physiol. Plant Mol. Biol.*, 45:287–301; Bartley, G. E. and Scolnik, P. A. (1995) *Plant Cell*, 7:1027–1038.) and gibberellin plant hormones (Sun, T. and Kamiya, Y. (1994) *Plant Cell*, 6:1509–1518), as well as for the biosynthesis of diterpenoid natural products, such as casbene (Dudley, M. W., Green, T. R. and West, C. A. (1986) *Plant Physiol.*, 81:343–348), oryzalexins (West, C. A., Lois, A. F., Wickham, K. A. and Ren, Y. -Y. (1990) *Recent Adv. Phytochem.*, 24:219–248) and paclitaxel (Koepp, A. E., Hezari, M., Zajicek, J., Stofer Vogel, B., LaFever, R. E., Lewis, N. G. and Croteau, R. (1995) *J. Biol. Chem.*, 270:8686–8690). Since GGPP synthase controls the rate of production of the branch point precursor of paclitaxel, and other useful diterpenes, there exists a need for methods of enhancing the production of GGPP synthase in cells and tissues that produce paclitaxel and other useful diterpenes.

SUMMARY OF THE INVENTION

In accordance with the foregoing, a cDNA encoding geranylgeranyl diphosphate synthase (GGPP synthase) from Canadian Yew (*Taxus canadensis*) has been isolated and sequenced, and the corresponding amino acid sequence has been deduced. Accordingly, the present invention relates to isolated DNA sequences which code for the expression of geranylgeranyl diphosphate synthase, such as the sequence designated SEQ ID NO:1 which encodes a geranylgeranyl diphosphate synthase (GGPP synthase) protein (SEQ ID NO:2) from Yew (*Taxus canadensis*). Additionally, the present invention relates to isolated, recombinant geranylgeranyl diphosphate synthase (GGPP synthase) protein from Yew (*Taxus canadensis*). In other aspects, the present invention is directed to replicable recombinant cloning vehicles comprising a nucleic acid sequence, e.g., a DNA sequence which codes for a geranylgeranyl diphosphate synthase, or for a base sequence sufficiently complementary to at least a portion of DNA or RNA encoding geranylgeranyl diphosphate synthase to enable hybridization therewith (e.g., antisense RNA or fragments of DNA complementary to a portion of DNA or RNA molecules encoding geranylgeranyl diphosphate synthase which are useful as polymerase chain reaction primers or as probes for geranylgeranyl diphosphate synthase or related genes). In yet other aspects of the invention, modified host cells are provided that have been transformed, transfected, infected and/or injected with a recombinant cloning vehicle and/or DNA sequence of the invention. In yet other aspects of the invention, nucleic acid molecules are provided that are useful as hybridization probes for identifying genes encoding geranylgeranyl diphosphate synthase proteins from microorganisms, such as *Taxomyces andreanae* and *Penicillium raistrickii*. Thus, the present invention provides for the recombinant expression of geranylgeranyl diphosphate synthase, and the inventive concepts may be used to facilitate the production, isolation and purification of significant quantities of recombinant geranylgeranyl diphosphate synthase (or of its primary enzyme products) for subsequent use, to obtain expression or enhanced expression of geranylgeranyl diphosphate synthase in plants, microorganisms or animals, or may be otherwise employed in an environment where the regulation or expression of geranylgeranyl diphosphate synthase is desired for the production of this synthase, or its enzyme product, or derivatives thereof. In another aspect, the present invention relates to manipulation of the level of production of diterpenes, including paclitaxel.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 2 shows the conversion of isopentenyl diphosphate (IPP) to dimethylallyl diphosphate (DMAPP) by isopentenyl diphosphate isomerase (FIG. 2A), and the geranylgeranyl diphosphate (GGPP) synthase-catalyzed condensation of IPP with the allylic diphosphate co-substrates DMAPP, geranyl diphosphate (GPP) and farnesyl diphosphate (FPP) (FIG. 2B). The product chain-length and double bond geometry are determined by the specificity of the prenyltransferase. The solvolysis products geranylgeraniol (GGOH), geranyllinalool (GLOH) and geranylnerol (GNOH) derived by treatment of GGPP with methanolic HCl are also illustrated (FIG. 2C).

DETAILED DESCRIPTION OF THE PREFERRED EMBODIMENT

Figure 1:
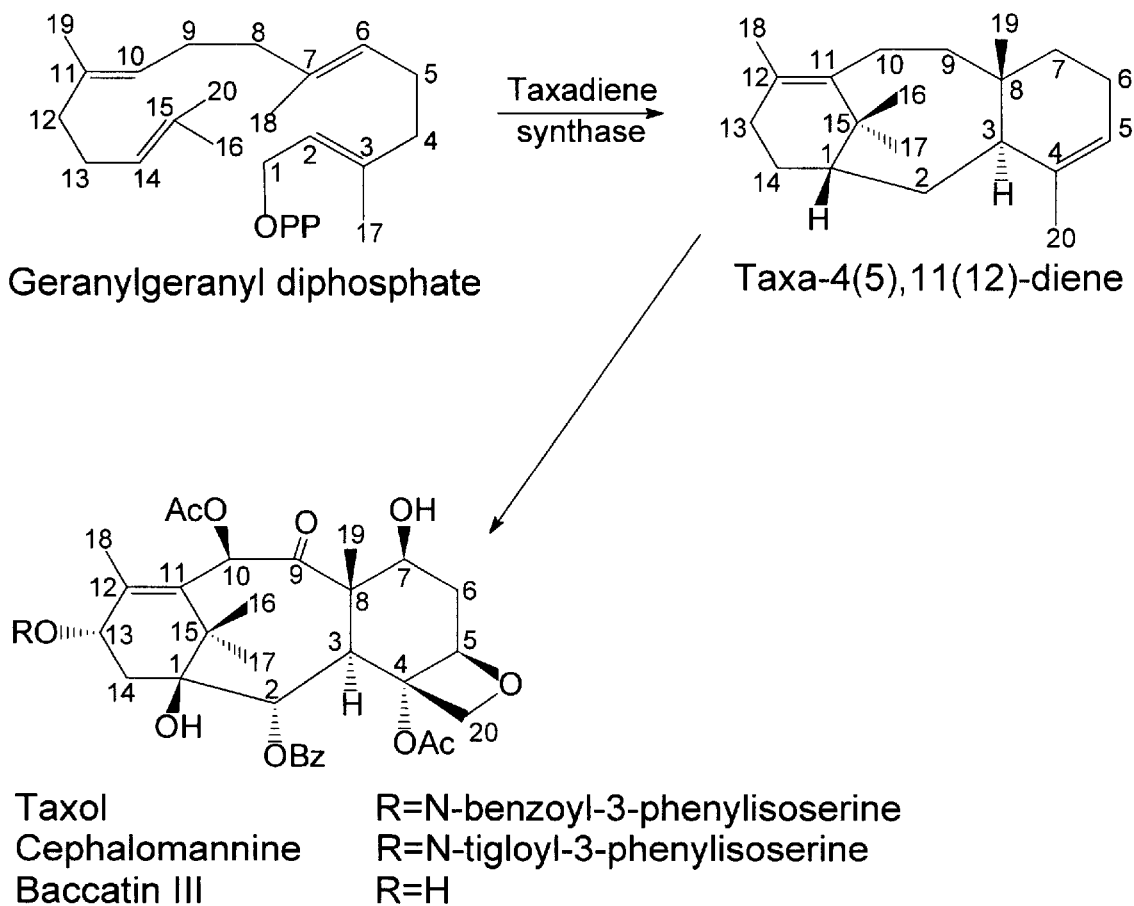
FIG. 1 depicts the cyclization of geranylgeranyl diphosphate to taxa-4(5),11 (12)-diene and elaboration of the olefin intermediate to paclitaxel.

As used herein, the terms "amino acid" and "amino acids" refer to all naturally occurring L-α-amino acids or their residues. The amino acids are identified by either the single-letter or three-letter designations:

| | | |
|---|---|---|
| Asp | D | aspartic acid |
| Thr | T | threonine |
| Ser | S | serine |
| Glu | E | glutamic acid |
| Pro | P | proline |
| Gly | G | glycine |
| Ala | A | alanine |
| Cys | C | cysteine |
| Val | V | valine |
| Met | M | methionine |
| Ile | I | isoleucine |
| Leu | L | leucine |
| Tyr | Y | tyrosine |

-continued

| Phe | F | phenylalanine |
| His | H | histidine |
| Lys | K | lysine |
| Arg | R | arginine |
| Trp | W | tryptophan |
| Gln | Q | glutamine |
| Asn | N | asparagine |

As used herein, the term "nucleotide" means a monomeric unit of DNA or RNA containing a sugar moiety (pentose), a phosphate and a nitrogenous heterocyclic base. The base is linked to the sugar moiety via the glycosidic carbon (1' carbon of pentose) and that combination of base and sugar is called a nucleoside. The base characterizes the nucleotide with the four bases of DNA being adenine ("A"), guanine ("G"), cytosine ("C") and thymine ("T"). Inosine ("I") is a synthetic base that can be used to substitute for any of the four, naturally-occurring bases (A, C, G or T). The four RNA bases are A,G,C and uracil ("U"). The nucleotide sequences described herein comprise a linear array of nucleotides connected by phosphodiester bonds between the 3' and 5' carbons of adjacent pentoses.

"Oligonucleotide" refers to short length single or double stranded sequences of deoxyribonucleotides linked via phosphodiester bonds. The oligonucleotides are chemically synthesized by known methods and purified, for example, on polyacrylamide gels.

The term "geranylgeranyl diphosphate synthase" (abbreviated as "GGPP synthase") is used herein to mean an enzyme capable of forming geranylgeranyl diphosphate (GGPP) by any one of, or all of, the following, numbered chemical reactions: (1) condensation of isopentenyl diphosphate (EPP) and dimethylallyl diphosphate (DMAPP) to form geranyl diphosphate (GPP), followed by condensation of GPP and IPP to form farnesyl diphosphate (FPP), followed by condensation of FPP and EPP to form GGPP; (2) condensation of GPP and EPP to form FPP, followed by condensation of FPP and IPP to form GGPP; (3) condensation of FPP and IPP to form geranylgeranyl diphosphate (GGPP).

Abbreviations used are: bp, base pair; DMAPP, dimethylallyl diphosphate; IPP, isopentenyl diphosphate; GPP, geranyl diphosphate; FPP, farnesyl diphosphate; GGPP, geranylgeranyl diphosphate; Mopso, 3-(N-morpholino)-2-hydroxypropane-sulfonic acid; Tris, Tris-(hydroxymethyl) aminomethane; UTR, untranslated region; TLC, thin layer chromatography; Tr, truncation site; GC, gas chromatography; Hepes, N-2-hydroxyethylpiperazine-N'-2-ethanesulfonic acid; kb, kilobase pairs.

The abbreviation "SSC" refers to a buffer used in nucleic acid hybridization solutions. One liter of the 20x (twenty times concentrate) stock SSC buffer solution (pH 7.0) contains 175.3 g sodium chloride and 88.2 g sodium citrate.

The terms "alteration", "amino acid sequence alteration", "variant" and "amino acid sequence variant" refer to geranylgeranyl diphosphate synthase molecules with some differences in their amino acid sequences as compared to the corresponding, native, i.e., naturally-occurring, geranylgeranyl diphosphate synthases. Ordinarily, the variants will possess at least about 70% homology with the corresponding native geranylgeranyl diphosphate synthases, and preferably, they will be at least about 80% homologous with the corresponding, native geranylgeranyl diphosphate synthases. The amino acid sequence variants of the geranylgeranyl diphosphate synthases falling within this invention possess substitutions, deletions, and/or insertions at certain positions. Sequence variants of geranylgeranyl diphosphate synthases may be used to attain desired enhanced or reduced enzymatic activity, modified regiochemistry or stereochemistry, or altered substrate utilization or product distribution.

Substitutional geranylgeranyl diphosphate synthase variants are those that have at least one amino acid residue in the native geranylgeranyl diphosphate synthase sequence removed and a different amino acid inserted in its place at the same position. The substitutions may be single, where only one amino acid in the molecule has been substituted, or they may be multiple, where two or more amino acids have been substituted in the same molecule. Substantial changes in the activity of the geranylgeranyl diphosphate synthase molecules of the present invention may be obtained by substituting an amino acid with a side chain that is significantly different in charge and/or structure from that of the native amino acid. This type of substitution would be expected to affect the structure of the polypeptide backbone and/or the charge or hydrophobicity of the molecule in the area of the substitution.

Moderate changes in the activity of the geranylgeranyl diphosphate synthase molecules of the present invention would be expected by substituting an amino acid with a side chain that is similar in charge and/or structure to that of the native molecule. This type of substitution, referred to as a conservative substitution, would not be expected to substantially alter either the structure of the polypeptide backbone or the charge or hydrophobicity of the molecule in the area of the substitution.

Insertional geranylgeranyl diphosphate synthase variants are those with one or more amino acids inserted immediately adjacent to an amino acid at a particular position in the native geranylgeranyl diphosphate synthase molecule. Immediately adjacent to an amino acid means connected to either the α-carboxy or (α-amino functional group of the amino acid. The insertion may be one or more amino acids. Ordinarily, the insertion will consist of one or two conservative amino acids. Amino acids similar in charge and/or structure to the amino acids adjacent to the site of insertion are defined as conservative. Alternatively, this invention includes insertion of an amino acid with a charge and/or structure that is substantially different from the amino acids adjacent to the site of insertion.

Deletional variants are those where one or more amino acids in the native geranylgeranyl diphosphate synthase molecules have been removed. Ordinarily, deletional variants will have one or two amino acids deleted in a particular region of the geranylgeranyl diphosphate synthase molecule.

The terms "biological activity", "biologically active", "activity" and "active" refer to the ability of the geranylgeranyl diphosphate synthases of the present invention to catalyze the formation of geranylgeranyl diphosphate (GGPP) by any one of, or all of, the following chemical reactions and sequence of chemical reactions: (1) condensation of isopentenyl diphosphate (IPP) and dimethylallyl diphosphate (DMAPP) to form geranyl diphosphate (GPP), followed by condensation of GPP and IPP to form farnesyl diphosphate (FPP), followed by condensation of FPP and IPP to form GGPP; (2) condensation of GPP and EPP to form FPP, followed by condensation of FPP and IPP to form GGPP; (3) condensation of FPP and IPP to form geranylgeranyl diphosphate (GGPP). Geranylgeranyl diphosphate synthase activity is measured in an enzyme activity assay, such as the assay described in Example 4. Amino acid sequence variants of the geranylgeranyl diphosphate synthases of the present invention may have desirable altered biological activity including, for example, altered reaction kinetics, substrate utilization, product distribution or other characteristics such as regiochemistry and stereochemistry.

The terms "DNA sequence encoding", "DNA encoding" "nucleic acid molecule encoding" and "nucleic acid encoding" refer to the order or sequence of deoxyribonucleotides along a strand of deoxyribonucleic acid. The order of these deoxyribonucleotides determines the order of amino acids along the translated polypeptide chain. The DNA sequence thus codes for the amino acid sequence.

The terms "replicable vector" "replicable expression vector" and "expression vector" refer to a piece of DNA, usually double-stranded, which may have inserted into it another piece of DNA (the insert DNA) such as, but not limited to, a cDNA molecule. The vector is used to transport the insert DNA into a suitable host cell. The insert DNA may be derived from the host cell, or may be derived from a different cell or organism. Once in the host cell, the vector can replicate independently of or coincidental with the host chromosomal DNA, and several copies of the vector and its inserted DNA may be generated. The terms "replicable expression vector" and "expression vector" refer exclusively to vectors that contain the necessary elements that permit translating the insert DNA into a polypeptide. Many molecules of the polypeptide encoded by the insert DNA can thus be rapidly synthesized.

The terms "transformed host cell," "transformed" and "transformation" refer to the introduction of DNA into a cell. The cell is termed a "host cell", and it may be a prokaryotic or a eukaryotic cell. Typical prokaryotic host cells include various strains of E. coli. Typical eukaryotic host cells are plant cells, such as maize cells, yeast cells, insect cells or animal cells. The introduced DNA is usually in the form of a vector containing an inserted piece of DNA. The introduced DNA sequence may be from the same species as the host cell or from a different species from the host cell, or it may be a hybrid DNA sequence, containing some foreign DNA and some DNA derived from the host species.

In accordance with the present invention, a cDNA (SEQ ID NO:1) encoding geranylgeranyl diphosphate synthase (SEQ ID NO:2) from Canadian Yew (*Taxus canadensis*) was isolated and sequenced in the following manner. A phage cDNA library from induced *T. canadensis* cells was prepared in λPG15. Total RNA was isolated from 14-day-old suspension cell cultures which had been induced with 200 μM methyl jasmonate 7 d prior to harvest by filtration. PolyA+ RNA was prepared by chromatography on oligo(dT)-cellulose.

An initial PCR product was amplified using 150 pmol/reaction of a reverse degenerate primer (SEQ ID NO:3), which corresponded to part of a specific amino acid sequence which was conserved among certain acetyltransferase enzymes. This primer fortuitously hybridized to two different regions of a geranylgeranyl diphosphate synthase mRNA. The resulting 861 bp fragment was ligated into pCR 2.1 Topo and the recombinant vector was transformed into E. coli XL1-Blue cells. Forty-five positive colonies were isolated from which plasmids were purified then sequenced. Only one isolated plasmid contained an insert sequence (SEQ ID NO:4) resembling geranylgeranyl diphosphate synthases from angiosperm plant species. When compared to other GGPP synthase sequences, this clone (SEQ ID NO:4) was found to encode the first 194 amino acids of the translated protein in addition to 279 bp of the 5'-UTR.

A 583 bp portion of this initial PCR product (extending from nucleotide 279 to nucleotide 861 of the 861 bp cDNA sequence set forth in SEQ ID NO:4) was used as a hybridization probe to obtain a full-length geranylgeranyl diphosphate synthase cDNA sequence. Thus, a nondegenerate forward primer (SEQ ID NO:5) and a nondegenerate reverse primer (SEQ ID NO:6) were designed which corresponded to nucleotides 279 to 300, and 839 to 861, respectively, of the 861 bp cDNA sequence set forth in SEQ ID NO:4. Nondegenerate forward primer (SEQ ID NO:5) and nondegenerate reverse primer (SEQ ID NO:6) were used to amplify the intervening 583 bp region of the 861 bp cDNA sequence set forth in SEQ ID NO:4.

The resulting, gel purified, amplified, cDNA fragment was then labeled with [$\alpha$-$^{32}$P]ATP and used to probe the *T. canadensis* cDNA library, containing approximately 80,000 independent clones. Sixteen positive clones were obtained, of which five encoded a putative geranylgeranyl diphosphate synthase protein.

The sequence of four of the five putative geranylgeranyl diphosphate synthase cDNA clones was identical and is set forth in SEQ ID NO:1. One full-length coding region, free of stop codons, was identified which begins 308 bp from the 5'-terminus of the sequence set forth in SEQ ID NO:1, and ends at a UGA codon at position 1489 of the sequence set forth in SEQ ID NO:1, thereby yielding a coding region of 1182 bp, with a 5'-UTR of 308 bp and a 3'-UTR of approximately 400 bp.

All known GGPP synthase sequences of plant origin appear to encode a transit peptide for organellar compartmentation of this prenyltransferase. Many of these enzymes have been shown to be localized to plastids. Since it was assumed that the *T. canadensis* GGPP synthase cDNA likewise would encode an organellar transit peptide, and that the resulting preprotein would likely be less catalytically efficient than the mature, proteolytically processed form, the deduced amino acid sequence of the putative, Taxus GGPP synthase (SEQ ID NO:2) was compared to angiosperm GGPP synthase sequences in order to identify the N-terminal and C-terminal boundaries of the mature protein.

Thus, comparison of plant-derived GGPP synthase amino acid sequences with the deduced *T. canadensis* protein (SEQ ID NO:2) showed that high-level conservation begins at $F^{99}$ of the amino acid sequence set forth in SEQ ID NO:2, indicating a logical truncation site at nucleotide 295 ($Tr^{295}$) of the GGPP synthase cDNA sequence set forth in SEQ ID NO:1; a second site (at nucleotide 313, $Tr^{313}$) was chosen (six residues downstream) because of the location of the convenient $M^{105}$ residue.

PCR primers containing a KpnI site (SEQ ID NO:7) or a BamHI site (SEQ ID NO:8) were designed to the 3'- and 5'-termini, respectively, of the presumptive full-length coding sequence. Additionally, a 5'-terminal primer (SEQ ID NO:9) (containing a BamHI site) was designed to generate a 5'-truncated version of the GGPP synthase protein sequence set forth in SEQ ID NO:2 beginning at $Tr^{295}$, while a second 5'-terminal primer (SEQ ID NO:10) (containing a BamHI site) was designed to generate a 5'-truncated version of the GGPP synthase protein sequence set forth in SEQ ID NO:2 beginning at $Tr^{313}$. Thus, the 5'-truncated versions of the GGPP synthase protein generated by the primer combinations SEQ ID NO:9 plus SEQ ID NO:7, and SEQ ID NO:10 plus SEQ ID NO:7 both lacked a transit peptide. After amplification with Pfu DNA polymerase, the BamHI/KpnI-digested fragment corresponding to each coding sequence was then subcloned into pYeDP60.

The three pYeDP60/*T. canadensis* GGPP synthase constructs were transformed and expressed in ANY119, an *S. cerevisiae* mutant (the bet2-1 mutant) that is defective for the 0-subunit of type II geranylgeranyltransferase. This mutation is lethal at high temperature but can be complemented by increasing the expression level of GGPP synthase. To determine if the three *T. canadensis* GGPP synthase forms (the full-length preprotein, the 5'-truncated protein beginning at Tr$^{295}$ and the 5'-truncated protein beginning at Tr$^{313}$) could be functionally expressed in yeast at levels sufficient to rescue this mutant when grown at the restrictive temperature, the expression of the three constructs was tested on three different carbon sources that differentially regulate GAL10-CYC1 promoter activity. The results of these expression studies indicated that both the full-length GGPP synthase clone (SEQ ID NO:1) and the Tr$^{295}$ truncation rescue the bet2-1 mutant and that, even under repressed conditions, enough leaky expression of GGPP synthase occurs to complement the mutation. When high level expression of the heterologous GGPP synthase was fully induced in yeast, the gene was toxic to the host yeast cells. The expression studies in yeast demonstrated that the full-length and Tr$^{295}$ GGPP synthase constructs yield active GGPP synthase, but the shorter Tr$^{313}$ truncation construct does not.

Additionally, a phage cDNA library from induced *T. cuspidata* cells was prepared in λPG15. Total RNA was isolated using an RNA Maxi kit (Qiagen) from 14-day-old suspension cell cultures which had been induced with 200 μM methyl jasmonate 7 d prior to harvest by filtration. PolyA$^+$ RNA was prepared by chromatography on oligo (dT)-cellulose (Pharmacia Biotech). The cDNA library was synthesized using a λZAP-cDNA synthesis kit and ZAP-cDNA gigapack III gold cloning kit (Stratagene) by following the manufacturer's instructions, except that λPG15 replaced λZAP as the cloning vector.

A partial-length cDNA clone (SEQ ID NO: II) encoding a GGPP synthase (SEQ ID NO:12) was amplified by PCR using the primers set forth in SEQ ID NO:7 and SEQ ID NO:9. The *T. cuspidata* GGPP synthase partial cDNA (SEQ ID NO:11) encodes the mature form of the *T. cuspidata* GGPP synthase enzyme, i.e., the form of the enzyme that lacks the transit peptide at the amino terminus. The deduced amino acid sequence of the *T. cuspidata* enzyme (SEQ ID NO:12) is identical to the mature form of the *T. canadensis* enzyme. At the nucleotide level, the *T. cuspidata* cDNA (SEQ ID NO:11) is almost identical (98.6% similarity) to the *T. canadensis* GGPP synthase cDNA (SEQ ID NO: I).

The isolation of cDNAs (SEQ ID NO:1; SEQ ID NO:11) encoding geranylgeranyl diphosphate synthase (SEQ ID NO:2; SEQ ID NO:12) permits the development of efficient expression systems for this functional enzyme; provides useful tools for examining the developmental regulation of GGPP synthase; permits investigation of the reaction mechanism(s) of this enzyme, and permits the isolation of other geranylgeranyl diphosphate synthases. For example, the nucleic acids of the present invention can be used as hybridization probes to identify geranylgeranyl diphosphate synthase genes from microorganisms, such as *Taxomyces andreanae* and *Penicillium raistrickii*, that are capable of producing paclitaxel. The isolation of geranylgeranyl diphosphate synthase cDNAs (SEQ ID NO:1; SEQ ID NO:11) also permits the transformation of a wide range of organisms in order to enhance, or otherwise alter, the synthesis of geranylgeranyl diphosphate, and of its derivative diterpenes, such as paclitaxel.

Although the geranylgeranyl diphosphate synthase protein set forth in SEQ ID NO:2 directs the enzyme to plastids, substitution of the presumptive targeting sequence of this enzyme (SEQ ID NO:2, amino acid residue numbers 1 to 98) with other transport sequences well known in the art (See, for example, the following publications, the cited portions of which are incorporated by reference herein: von Heijne et al., *Eur. J. Biochem.*, 180:535–545, 1989; Stryer, *Biochemistry*, W. H. Freeman and Company, New York, N.Y., p. 769 [1988]) may be employed to direct geranylgeranyl diphosphate synthase to other cellular or extracellular locations.

In addition to the native geranylgeranyl diphosphate synthase amino acid sequence of, for example, SEQ ID NO:2, sequence variants produced by deletions, substitutions, mutations and/or insertions are intended to be within the scope of the invention except insofar as limited by the prior art. The geranylgeranyl diphosphate synthase amino acid sequence variants of this invention may be constructed by mutating the DNA sequences that encode the wild-type synthases, such as by using techniques commonly referred to as site-directed mutagenesis. Nucleic acid molecules encoding the geranylgeranyl diphosphate synthases of the present invention can be mutated by a variety of PCR techniques well known to one of ordinary skill in the art. (See, for example, the following publications, the cited portions of which are incorporated by reference herein: "PCR Strategies", M. A. Innis, D. H. Gelfand and J. J. Sninsky, eds., 1995, Academic Press, San Diego, Calif. (Chapter 14); "PCR Protocols: A Guide to Methods and Applications", M. A. Innis, D. H. Gelfand, J. J. Sninsky and T. J. White, eds., Academic Press, NY (1990).

By way of non-limiting example, the two primer system utilized in the Transformer Site-Directed Mutagenesis kit from Clontech, may be employed for introducing site-directed mutants into the geranylgeranyl diphosphate synthase genes of the present invention. Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of *E. coli*. Plasmid DNA is isolated from the transformed bacteria, restricted with the relevant restriction enzyme (thereby linearizing the unmutated plasmids), and then retransformed into *E. coli*. This system allows for generation of mutations directly in an expression plasmid, without the necessity of subcloning or generation of single-stranded phagemids. The tight linkage of the two mutations and the subsequent linearization of unmutated plasmids results in high mutation efficiency and allows minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Transformants can be screened by sequencing the plasmid DNA through the mutagenized region to identify and sort mutant clones. Each mutant DNA can then be fully sequenced or restricted and analyzed by electrophoresis on Mutation Detection Enhancement gel (J. T. Baker) to confirm that no other alterations in the sequence have occurred (by band shift comparison to the unmutagenized control).

Again, by way of non-limiting example, the two primer system utilized in the QuikChange™ Site-Directed Mutagenesis kit from Stratagene (LaJolla, Calif.), may be employed for introducing site-directed mutants into the geranylgeranyl diphosphate synthase genes of the present invention. Double-stranded plasmid DNA, containing the insert bearing the target mutation site, is denatured and mixed with two oligonucleotides complementary to each of the strands of the plasmid DNA at the target mutation site. The annealed oligonucleotide primers are extended using Pfu DNA polymerase, thereby generating a mutated plasmid containing staggered nicks. After temperature cycling, the unmutated, parental DNA template is digested with restriction enzyme DpnI which cleaves methylated or hemimethylated DNA, but which does not cleave unmethylated DNA. The parental, template DNA is almost always methylated or hemimethylated since most strains of E. coli, from which the template DNA is obtained, contain the required methylase activity. The remaining, annealed vector DNA incorporating the desired mutation(s) is transformed into E. coli.

The mutated geranylgeranyl diphosphate synthase gene can be cloned into a pET (or other) overexpression vector that can be employed to transform E. coli such as strain E. coli BL21(DE3)pLysS, for high level production of the mutant protein, and purification by standard protocols. Examples of plasmid vectors and E. coli strains that can be used to express high levels of the geranylgeranyl diphosphate synthase proteins of the present invention are set forth in Sambrook et al, *Molecular Cloning, A Laboratory Manual,* 2nd Edition (1989), Chapter 17. The method of FAB-MS mapping can be employed to rapidly check the fidelity of mutant expression. This technique provides for sequencing segments throughout the whole protein and provides the necessary confidence in the sequence assignment. In a mapping experiment of this type, protein is digested with a protease (the choice will depend on the specific region to be modified since this segment is of prime interest and the remaining map should be identical to the map of unmutagenized protein). The set of cleavage fragments is fractionated by microbore HPLC (reversed phase or ion exchange, again depending on the specific region to be modified) to provide several peptides in each fraction, and the molecular weights of the peptides are determined by FAB-MS. The masses are then compared to the molecular weights of peptides expected from the digestion of the predicted sequence, and the correctness of the sequence quickly ascertained. Since the exemplary mutagenesis techniques set forth herein produce site-directed mutations, sequencing of the altered peptide should not be necessary if the mass spectrograph agrees with prediction. If necessary to verify a changed residue, CAD-tandem MS/MS can be employed to sequence the peptides of the mixture in question, or the target peptide can be purified for subtractive Edman degradation or carboxypeptidase Y digestion depending on the location of the modification.

In the design of a particular site directed mutagenesis experiment, it is generally desirable to first make a non-conservative substitution (e.g., Ala for Cys, His or Glu) and determine if activity is greatly impaired as a consequence. The properties of the mutagenized protein are then examined with particular attention to the kinetic parameters of $K_m$ and $k_{cat}$ as sensitive indicators of altered function, from which changes in binding and/or catalysis per se may be deduced by comparison to the native enzyme. If the residue is by this means demonstrated to be important by activity impairment, or knockout, then conservative substitutions can be made, such as Asp for Glu to alter side chain length, Ser for Cys, or Arg for His. For hydrophobic segments, it is largely size that is usefully altered, although aromatics can also be substituted for alkyl side chains. Changes in the normal product distribution can indicate which step(s) of the reaction sequence have been altered by the mutation. Modification of the hydrophobic pocket can be employed to change binding conformations for substrates and result in altered regiochemistry and/or stereochemistry.

Other site directed mutagenesis techniques may also be employed with the nucleotide sequences of the invention. For example, restriction endonuclease digestion of DNA followed by ligation may be used to generate deletion variants of geranylgeranyl diphosphate synthase, as described in section 15.3 of Sambrook et al. *Molecular Cloning: A Laboratory Manual,* 2nd Ed., Cold Spring Harbor Laboratory Press, New York, N.Y. [1989], incorporated herein by reference. A similar strategy may be used to construct insertion variants, as described in section 15.3 of Sambrook et al., supra.

Oligonucleotide-directed mutagenesis may also be employed for preparing substitution variants of this invention. It may also be used to conveniently prepare the deletion and insertion variants of this invention. This technique is well known in the art as described by Adelman et al. (DNA 2:183 [1983]); Sambrook et al., supra; "Current Protocols in Molecular Biology", 1991, Wiley (NY), F. T. Ausubel, R. Brent, R. E. Kingston, D. D. Moore, J. D. Seidman, J. A. Smith and K. Struhl, eds, incorporated herein by reference.

Generally, oligonucleotides of at least 25 nucleotides in length are used to insert, delete or substitute two or more nucleotides in the geranylgeranyl diphosphate synthase molecule. An optimal oligonucleotide will have 12 to 15 perfectly matched nucleotides on either side of the nucleotides coding for the mutation. To mutagenize wild-type geranylgeranyl diphosphate synthase, the oligonucleotide is annealed to the single-stranded DNA template molecule under suitable hybridization conditions. A DNA polymerizing enzyme, usually the Klenow fragment of E. coli DNA polymerase I, is then added. This enzyme uses the oligonucleotide as a primer to complete the synthesis of the mutation-bearing strand of DNA. Thus, a heteroduplex molecule is formed such that one strand of DNA encodes the wild-type synthase inserted in the vector, and the second strand of DNA encodes the mutated form of the synthase inserted into the same vector. This heteroduplex molecule is then transformed into a suitable host cell.

Mutants with more than one amino acid substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. An alternative method involves two or more rounds of mutagenesis to produce the desired mutant. The first round is as described for the single mutants: wild-type geranylgeranyl diphosphate synthase DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

A gene encoding geranylgeranyl diphosphate synthase may be incorporated into any organism (intact plant, animal, microbe, etc.), or cell culture derived therefrom, that produces substrates that can be converted to geranylgeranyl diphosphate. A geranylgeranyl diphosphate synthase gene may be introduced into any organism for a variety of purposes including, but not limited to: production of geranylgeranyl diphosphate synthase, or its product geranylgeranyl diphosphate; enhancement of the rate of production and/or the absolute amount of one or more diterpenes derived from geranylgeranyl diphosphate; enhancement of the rate of production and/or the absolute amount of paclitaxel or related taxoids; the enhanced production of resin acids; the enhanced production of gibberellin plant hormones. While the nucleic acid molecules of the present invention can be introduced into any organism, the nucleic acid molecules of the present invention will preferably be introduced into a gymnosperm species, most preferably a Taxus species.

Advantages associated with expression of the nucleic acid molecules of the present invention in a gymnosperm species, most preferably a Taxus species, include, but are not limited to: (1) compatible codon usage for maximum translational efficiency; (2) recognition of the encoded preprotein by the plastid import system; (3) maximum fidelity in proteolytic processing by the plastids to the mature enzyme form and (4) optimum protein-protein interaction with upstream and downstream enzymes of the paclitaxel pathway for most efficient channeling of metabolites.

Eukaryotic expression systems may be utilized for the production of geranylgeranyl diphosphate synthase since they are capable of carrying out any required posttranslational modifications and of directing the enzyme to the proper cellular compartment. A representative eukaryotic expression system for this purpose uses the recombinant baculovirus, *Autographa californica* nuclear polyhedrosis virus (AcNPV; M. D. Summers and G. E. Smith, *A Manual of Methods for Baculovirus Vectors and Insect Cell Culture Procedures* [1986]; Luckow et al., *Bio-technology*, 6:47–55 [1987]) for expression of the geranylgeranyl diphosphate synthases of the invention. Infection of insect cells (such as cells of the species *Spodoptera frugiperda*) with the recombinant baculoviruses allows for the production of large amounts of the geranylgeranyl diphosphate synthase proteins. In addition, the baculovirus system has other important advantages for the production of recombinant geranylgeranyl diphosphate synthase. For example, baculoviruses do not infect humans and can therefore be safely handled in large quantities. In the baculovirus system, a DNA construct is prepared including a DNA segment encoding geranylgeranyl diphosphate synthase and a vector. The vector may comprise the polyhedron gene promoter region of a baculovirus, the baculovirus flanking sequences necessary for proper cross-over during recombination (the flanking sequences comprise about 200–300 base pairs adjacent to the promoter sequence) and a bacterial origin of replication which permits the construct to replicate in bacteria. The vector is constructed so that (i) the DNA segment is placed adjacent (or operably linked or "downstream" or "under the control of") to the polyhedron gene promoter and (ii) the promoter/geranylgeranyl diphosphate synthase combination is flanked on both sides by 200–300 base pairs of baculovirus DNA (the flanking sequences).

To produce the geranylgeranyl diphosphate synthase DNA construct, a cDNA clone encoding the full length geranylgeranyl diphosphate synthase is obtained using methods such as those described herein. The DNA construct is contacted in a host cell with baculovirus DNA of an appropriate baculovirus (that is, of the same species of baculovirus as the promoter encoded in the construct) under conditions such that recombination is effected. The resulting recombinant baculoviruses encode the full geranylgeranyl diphosphate synthase. For example, an insect host cell can be cotransfected or transfected separately with the DNA construct and a functional baculovirus. Resulting recombinant baculoviruses can then be isolated and used to infect cells to effect production of the geranylgeranyl diphosphate synthase. Host insect cells include, for example, *Spodoptera frugiperda* cells, that are capable of producing a baculovirus-expressed geranylgeranyl diphosphate synthase. Insect host cells infected with a recombinant baculovirus of the present invention are then cultured under conditions allowing expression of the baculovirus-encoded geranylgeranyl diphosphate synthase. Geranylgeranyl diphosphate synthase thus produced is then extracted from the cells using methods known in the art.

Other eukaryotic microbes such as yeasts may also be used to practice this invention. The baker's yeast *Saccharomyces cerevisiae*, is a commonly used yeast, although several other strains are available. The plasmid YRp7 (Stinchcomb et al., *Nature*, 282:39 [1979]; Kingsman et al., *Gene* 7:141 [1979]; Tschemper et al., *Gene*, 10:157 [1980]) is commonly used as an expression vector in Saccharomyces. This plasmid contains the trp1 gene that provides a selection marker for a mutant strain of yeast lacking the ability to grow in tryptophan, such as strains ATCC No. 44,076 and PEP4-1 (Jones, *Genetics*, 85:12 [1977]). The presence of the trp1 lesion as a characteristic of the yeast host cell genome then provides an effective environment for detecting transformation by growth in the absence of tryptophan. Yeast host cells are generally transformed using the polyethylene glycol method, as described by Hinnen (*Proc. Natl. Acad. Sci. USA*, 75:1929 [1978]). Additional yeast transformation protocols are set forth in Gietz et al., *N.A.R,* 20(17):1425(1992); Reeves et al., *FEMS*, 99(2–3): 193–197, (1992), both of which publications are incorporated herein by reference.

Suitable promoting sequences in yeast vectors include the promoters for 3-phosphoglycerate kinase (Hitzeman et al., *J. Biol. Chem.*, 255:2073 [1980]) or other glycolytic enzymes (Hess et al., *J. Adv. Enzyme Reg.* 7:149 [1968]; Holland et al., *Biochemistry*, 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In the construction of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

Cell cultures derived from multicellular organisms, such as plants, may be used as hosts to practice this invention. Transgenic plants can be obtained, for example, by transferring plasmids that encode geranylgeranyl diphosphate synthase and a selectable marker gene, e.g., the kan gene encoding resistance to kanamycin, into *Agrobacterium tumifaciens* containing a helper Ti plasmid as described in Hoeckema et al., *Nature,* 303:179–181 [1983] and culturing the Agrobacterium cells with leaf slices, or other tissues or cells, of the plant to be transformed as described by An et al., *Plant Physiology,* 81:301–305 [1986]. Transformation of cultured plant host cells is normally accomplished through *Agrobacterium tumifaciens*. Cultures of mammalian host cells and other host cells that do not have rigid cell membrane barriers are usually transformed using the calcium phosphate method as originally described by Graham and Van der Eb (*Virology,* 52:546 [1978]) and modified as described in sections 16.32–16.37 of Sambrook et al., supra. However, other methods for introducing DNA into cells such as Polybrene (Kawai and Nishizawa, *Mol. Cell. Biol.,* 4:1172 [1984]), protoplast fusion (Schaffner, *Proc. Natl. Acad. Sci. USA,* 77:2163 [1980]), electroporation (Neumann et al., *EMBO J.,* 1:841 [1982]), and direct microinjection into nuclei (Capecchi, *Cell,* 22:479 [1980]) may also be used. Additionally, animal transformation strategies are reviewed in Monastersky G. M. and Robl, J. M., *Strategies in Transgenic Animal Science,* ASM Press, Washington, D.C., 1995, incorporated herein by reference. Transformed plant calli may be selected through the selectable marker by growing the cells on a medium containing, e.g., kanamycin, and appropriate amounts of phytohormone such as naphthalene acetic acid and benzyladenine for callus and shoot induction. The plant cells may then be regenerated and the resulting plants transferred to soil using techniques well known to those skilled in the art.

In addition, a gene regulating geranylgeranyl diphosphate synthase production can be incorporated into the plant along with a necessary promoter which is inducible. In the practice of this embodiment of the invention, a promoter that only responds to a specific external or internal stimulus is fused to the target cDNA. Thus, the gene will not be transcribed except in response to the specific stimulus. As long as the gene is not being transcribed, its gene product is not produced.

An illustrative example of a responsive promoter system that can be used in the practice of this invention is the glutathione-S-transferase (GST) system in maize. GSTs are a family of enzymes that can detoxify a number of hydrophobic electrophilic compounds that often are used as pre-emergent herbicides (Weigand et al., *Plant Molecular Biology,* 7:235–243 [1986]). Studies have shown that the GSTs are directly involved in causing this enhanced herbicide tolerance. This action is primarily mediated through a specific 1.1 kb mRNA transcription product. In short, maize has a naturally occurring quiescent gene already present that can respond to external stimuli and that can be induced to produce a gene product. This gene has previously been identified and cloned. Thus, in one embodiment of this invention, the promoter is removed from the GST responsive gene and attached to a geranylgeranyl diphosphate synthase gene that previously has had its native promoter removed. This engineered gene is the combination of a promoter that responds to an external chemical stimulus and a gene responsible for successful production of geranylgeranyl diphosphate synthase.

In addition to the methods described above, several methods are known in the art for transferring cloned DNA into a wide variety of plant species, including gymnosperms, angiosperms, monocots and dicots (see, e.g., Glick and Thompson, eds., *Methods in Plant Molecular Biology,* CRC Press, Boca Raton, Fla. [1993], incorporated by reference herein). Representative examples include electroporation-facilitated DNA uptake by protoplasts in which an electrical pulse transiently permeabilizes cell membranes, permitting the uptake of a variety of biological molecules, including recombinant DNA (Rhodes et al., *Science,* 240(4849):204–207 [1988]); treatment of protoplasts with polyethylene glycol (Lyznik et al., *Plant Molecular Biology,* 13:151–161 [1989]); and bombardment of cells with DNA-laden microprojectiles which are propelled by explosive force or compressed gas to penetrate the cell wall (Klein et al *Plant Physiol.* 91:440–444 [1989] and Boynton et al., *Science,* 240(4858):1534–1538 [1988]). Transformation of Taxus species can be achieved, for example, by employing the methods set forth in Han et al, *Plant Science,* 95:187–196 (1994), incorporated by reference herein. A method that has been applied to Rye plants (*Secale cereale*) is to directly inject plasmid DNA, including a selectable marker gene, into developing floral tillers (de la Pena et al., *Nature* 325:274–276 (1987)). Further, plant viruses can be used as vectors to transfer genes to plant cells. Examples of plant viruses that can be used as vectors to transform plants include the Cauliflower Mosaic Virus (Brisson et al., *Nature* 310: 511–514 (1984); Additionally, plant transformation strategies and techniques are reviewed in Birch, R. G., *Ann Rev Plant Phys Plant Mol Biol,* 48:297 (1997); Forester et al., *Exp. Agric.,* 33:15–33 (1997). The aforementioned publications disclosing plant transformation techniques are incorporated herein by reference, and minor variations make these technologies applicable to a broad range of plant species.

Each of these techniques has advantages and disadvantages. In each of the techniques, DNA from a plasmid is genetically engineered such that it contains not only the gene of interest, but also selectable and screenable marker genes. A selectable marker gene is used to select only those cells that have integrated copies of the plasmid (the construction is such that the gene of interest and the selectable and screenable genes are transferred as a unit). The screenable gene provides another check for the successful culturing of only those cells carrying the genes of interest. A commonly used selectable marker gene is neomycin phosphotransferase II (NPT II). This gene conveys resistance to kanamycin, a compound that can be added directly to the growth media on which the cells grow. Plant cells are normally susceptible to kanamycin and, as a result, die. The presence of the NPT II gene overcomes the effects of the kanamycin and each cell with this gene remains viable. Another selectable marker gene which can be employed in the practice of this invention is the gene which confers resistance to the herbicide glufosinate (Basta). A screenable gene commonly used is the 0-glucuronidase gene (GUS). The presence of this gene is characterized using a histochemical reaction in which a sample of putatively transformed cells is treated with a GUS assay solution. After an appropriate incubation, the cells containing the GUS gene turn blue.

The plasmid containing one or more of these genes is introduced into either plant protoplasts or callus cells by any of the previously mentioned techniques. If the marker gene is a selectable gene, only those cells that have incorporated the DNA package survive under selection with the appropriate phytotoxic agent. Once the appropriate cells are identified and propagated, plants are regenerated. Progeny from the transformed plants must be tested to insure that the DNA package has been successfully integrated into the plant genome.

Mammalian host cells may also be used in the practice of the invention. Examples of suitable mammalian cell lines include monkey kidney CVI line transformed by SV40 (COS-7, ATCC CRL 1651); human embryonic kidney line 293S (Graham et al., J. Gen. Virol., 36:59 [1977]); baby hamster kidney cells (BHK, ATCC CCL 10); Chinese hamster ovary cells (Urlab and Chasin, *Proc. Natl. Acad. Sci USA* 77:4216 [1980]); mouse sertoli cells (TM4, Mather, *Biol. Reprod.,* 23:243 [1980]); monkey kidney cells (CVI-76, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL 5 1); rat hepatoma cells (HTC, MI.54, Baumann et al., *J. Cell Biol.,* 85:1 [1980]); and TRI cells (Mather et al., *Annals N.Y. Acad Sci.,* 383:44 [1982]). Expression vectors for these cells ordinarily include (if necessary) DNA sequences for an origin of replication, a promoter located in front of the gene to be expressed, a ribosome binding site, an RNA splice site, a polyadenylation site, and a transcription terminator site.

Promoters used in mammalian expression vectors are often of viral origin. These viral promoters are commonly derived from polyoma virus, Adenovirus 2, and most frequently Simian Virus 40 (SV40). The SV40 virus contains two promoters that are termed the early and late promoters. These promoters are particularly useful because they are both easily obtained from the virus as one DNA fragment that also contains the viral origin of replication (Fiers et al., *Nature,* 273:113 [1978]). Smaller or larger SV40 DNA fragments may also be used, provided they contain the approximately 250-bp sequence extending from the HindIII site toward the BglI site located in the viral origin of replication.

Alternatively, promoters that are naturally associated with the foreign gene (homologous promoters) may be used provided that they are compatible with the host cell line selected for transformation.

An origin of replication may be obtained from an exogenous source, such as SV40 or other virus (e.g., Polyoma, Adeno, VSV, BPV) and inserted into the cloning vector. Alternatively, the origin of replication may be provided by the host cell chromosomal replication mechanism. If the vector containing the foreign gene is integrated into the host cell chromosome, the latter is often sufficient.

The use of a secondary DNA coding sequence can enhance production levels of geranylgeranyl diphosphate synthase in transformed cell lines. The secondary coding sequence typically comprises the enzyme dihydrofolate reductase (DIFR). The wild-type form of DHFR is normally inhibited by the chemical methotrexate (MTX). The level of DHFR expression in a cell will vary depending on the amount of MTX added to the cultured host cells. An additional feature of DHFR that makes it particularly useful as a secondary sequence is that it can be used as a selection marker to identify transformed cells. Two forms of DHFR are available for use as secondary sequences, wild-type DHFR and MTX-resistant DHFR. The type of DHFR used in a particular host cell depends on whether the host cell is DHFR deficient (such that it either produces very low levels of DHFR endogenously, or it does not produce functional DHFR at all). DHFR-deficient cell lines such as the CHO cell line described by Urlaub and Chasin, supra, are transformed with wild-type DHFR coding sequences. After transformation, these DHFR-deficient cell lines express functional DHFR and are capable of growing in a culture medium lacking the nutrients hypoxanthine, glycine and thymidine. Nontransformed cells will not survive in this medium.

The MTX-resistant form of DHFR can be used as a means of selecting for transformed host cells in those host cells that endogenously produce normal amounts of functional DHFR that is MTX sensitive. The CHO-Kl cell line (ATCC No. CL 61) possesses these characteristics, and is thus a useful cell line for this purpose. The addition of MTX to the cell culture medium will permit only those cells transformed with the DNA encoding the MTX-resistant DHFR to grow. The nontransformed cells will be unable to survive in this medium.

Prokaryotes may also be used as host cells for the initial cloning steps of this invention. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include *E. coli* K12 strain 94 (ATCC No. 31,446), *E. coli* strain W3 110 (ATCC No. 27,325) *E. coli* X1776 (ATCC No. 31,537), and *E. coli* B; however many other strains of *E. coli*, such as HB101, JM101, NM522, NM538, NM539, and many other species and genera of prokaryotes including bacilli such as *Bacillus subtilis,* other enterobacteriaceae such as *Salmonella typhimurium* or *Serratia marcesans,* and various Pseudomonas species may all be used as hosts. Prokaryotic host cells or other host cells with rigid cell walls are preferably transformed using the calcium chloride method as described in section 1.82 of Sambrook et al., supra. Alternatively, electroporation may be used for transformation of these cells. Prokaryote transformation techniques are set forth in Dower, W. J., in Genetic Engineering, Principles and Methods, 12:275–296, Plenum Publishing Corp., 1990; Hanahan et al., *Meth. Enzymol.,* 204:63 (1991).

As a representative example, cDNA sequences encoding geranylgeranyl diphosphate synthase may be transferred to the $(His)_6$•Tag pET vector commercially available (from Novagen) for overexpression in *E. coil* as heterologous host. This pET expression plasmid has several advantages in high level heterologous expression systems. The desired cDNA insert is ligated in frame to plasmid vector sequences encoding six histidines followed by a highly specific protease recognition site (thrombin) that are joined to the amino terminus codon of the target protein. The histidine "block" of the expressed fusion protein promotes very tight binding to immobilized metal ions and permits rapid purification of the recombinant protein by immobilized metal ion affinity chromatography. The histidine leader sequence is then cleaved at the specific proteolysis site by treatment of the purified protein with thrombin, and the geranylgeranyl diphosphate synthase again purified by immobilized metal ion affinity chromatography, this time using a shallower imidazole gradient to elute the recombinant synthases while leaving the histidine block still adsorbed. This overexpression-purification system has high capacity, excellent resolving power and is fast, and the chance of a contaminating *E. coil* protein exhibiting similar binding behavior (before and after thrombin proteolysis) is extremely small.

As will be apparent to those skilled in the art, any plasmid vectors containing replicon and control sequences that are derived from species compatible with the host cell may also be used in the practice of the invention. The vector usually has a replication site, marker genes that provide phenotypic selection in transformed cells, one or more promoters, and a polylinker region containing several restriction sites for insertion of foreign DNA. Plasmids typically used for transformation of *E. coli* include pBR322, pUC18, pUC19, pUCI18, pUC119, and Bluescript M13, all of which are described in sections 1.12–1.20 of Sambrook et al., supra. However, many other suitable vectors are available as well. These vectors contain genes coding for ampicillin and/or tetracycline resistance which enables cells transformed with these vectors to grow in the presence of these antibiotics.

The promoters most commonly used in prokaryotic vectors include the β-lactamase (penicillinase) and lactose promoter systems (Chang et al. *Nature*, 375:615 [1978]; Itakura et al., *Science*, 198:1056 [1977]; Goeddel et al., *Nature*, 281:544 [1979]) and a tryptophan (trp) promoter system (Goeddel et al., *Nucl. Acids Res.*, 8:4057 [1980]; EPO Appl. Publ. No. 36,776), and the alkaline phosphatase systems. While these are the most commonly used, other microbial promoters have been utilized, and details concerning their nucleotide sequences have been published, enabling a skilled worker to ligate them functionally into plasmid vectors (see Siebenlist et al., *Cell*, 20:269 [1980]).

Many eukaryotic proteins normally secreted from the cell contain an endogenous secretion signal sequence as part of the amino acid sequence. Thus, proteins normally found in the cytoplasm can be targeted for secretion by linking a signal sequence to the protein. This is readily accomplished by ligating DNA encoding a signal sequence to the 5' end of the DNA encoding the protein and then expressing this fusion protein in an appropriate host cell. The DNA encoding the signal sequence may be obtained as a restriction fragment from any gene encoding a protein with a signal sequence. Thus, prokaryotic, yeast, and eukaryotic signal sequences may be used herein, depending on the type of host cell utilized to practice the invention. The DNA and amino acid sequence encoding the signal sequence portion of several eukaryotic genes including, for example, human growth hormone, proinsulin, and proalbumin are known (see Stryer, *Biochemistry* W. H. Freeman and Company, New York, N.Y., p. 769 [1988]), and can be used as signal sequences in appropriate eukaryotic host cells. Yeast signal sequences, as for example acid phosphatase (Arima et al., *Nuc. Acids Res.*, 11:1657 [1983]), α-factor, alkaline phosphatase and invertase may be used to direct secretion from yeast host cells. Prokaryotic signal sequences from genes encoding, for example, LamB or OmpF (Wong et al., *Gene*, 68:193 [1988]), MalE, PhoA, or beta-lactamase, as well as other genes, may be used to target proteins from prokaryotic cells into the culture medium.

Trafficking sequences from plants, animals and microbes can be employed in the practice of the invention to direct the geranylgeranyl diphosphate synthase proteins of the present invention to the cytoplasm, endoplasmic reticulum, mitochondria or other cellular components, or to target the protein for export to the medium. These considerations apply to the overexpression of geranylgeranyl diphosphate synthase, and to direction of expression within cells or intact organisms to permit gene product function in any desired location.

The construction of suitable vectors containing DNA encoding replication sequences, regulatory sequences, phenotypic selection genes and the geranylgeranyl diphosphate synthase DNA of interest are prepared using standard recombinant DNA procedures. Isolated plasmids and DNA fragments are cleaved, tailored, and ligated together in a specific order to generate the desired vectors, as is well known in the art (see, for example, Sambrook et al., supra).

As discussed above, geranylgeranyl diphosphate synthase variants are preferably produced by means of mutation(s) that are generated using the method of site-specific mutagenesis. This method requires the synthesis and use of specific oligonucleotides that encode both the sequence of the desired mutation and a sufficient number of adjacent nucleotides to allow the oligonucleotide to stably hybridize to the DNA template.

The foregoing may be more fully understood in connection with the following representative examples, in which "Plasmids" are designated by a lower case p followed by an alphanumeric designation. The starting plasmids used in this invention are either commercially available, publicly available on an unrestricted basis, or can be constructed from such available plasmids using published procedures. In addition, other equivalent plasmids are known in the art and will be apparent to the ordinary artisan.

"Digestion", "cutting" or "cleaving" of DNA refers to catalytic cleavage of the DNA with an enzyme that acts only at particular locations in the DNA. These enzymes are called restriction endonucleases, and the site along the DNA sequence where each enzyme cleaves is called a restriction site. The restriction enzymes used in this invention are commercially available and are used according to the instructions supplied by the manufacturers. (See also sections 1.60–1.61 and sections 3.38–3.39 of Sambrook et al., supra.)

"Recovery" or "isolation" of a given fragment of DNA from a restriction digest means separation of the resulting DNA fragment on a polyacrylamide or an agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al. (*Nucleic Acids Res.*, 9:6103–6114 [1982]), and Goeddel et al. (*Nucleic Acids Res.*, supra).

The following examples merely illustrate the best mode now contemplated for practicing the invention, but should not be construed to limit the invention.

EXAMPLE 1

Isolation of a Full-Length Geranylgeranyl Diphosphate Synthase cDNA Clone Unless otherwise stated, the following substrates and reagents were utilized in the Examples set forth herein. General molecular biology reagents were obtained from Gibco BRL Life Technologies, Inc., (Rockville, Md.), Stratagene Cloning Systems, Inc., (La Jolla, Calif.), or New England Biolabs, Inc., (Beverly, Mass.), unless otherwise indicated. Biochemicals and standards were obtained from Sigma Chemical Company (St. Louis, Mo.), except as follows. [4-$^{14}$C]Isopentenyl diphosphate (54.1 Ci/mol), [α-$^{32}$P]dCTP (3000 Ci/mol) and [α-$^{32}$P]dATP (3000 Ci/mol) were obtained from DuPont NEN Company (Boston, Mass.); [1-$^{3}$H$_1$]geranylgeranyl diphosphate (120 Ci/mol) was prepared by a modification of the method of Cramer and Böhm (Cramer, F. and Böhm, W. (1959) *Angew. Chem.*, 71:775) and was purified as previously described (LaFever, R. E., Stofer Vogel, B. and Croteau, R. (1994) *Arch. Biochem. Biophys.*, 313:139–149); Farnesyl diphosphate was obtained from American Radiolabeled Chemicals Inc. (St. Louis, Mo.); and Geranylgeraniol and geranyllinalool were obtained from Kuraray Co. and American Tokyo Kasei, Inc., respectively.

Unless otherwise stated, the following cell cultures were utilized in the Examples set forth herein. *T. canadensis* suspension-cultured cells were initiated from embryos and maintained as previously described, and the growth and paclitaxel content of the cells were monitored as before (Hezari, M., Ketchum, R. E. B., Gibson, D. M. and Croteau, R. (1997) *Arch. Biochem. Biophys.,* 337:185–190). *Escherichia coli* strains LE392, XL1-Blue, and XL1-Blue MRF' were used for standard molecular biology procedures. *E. coli* JM109 (λCC) (unpublished, chloramphenicol resistant strain containing cre expressed on a λ lysogen) and the yeast/*E. coli* phage λ expression vector λPG15 (Brunelli, J. P. and Pall, M. L. (1993) *Yeast,* 9:1309–1318) were gifts from Dr. M. Pall, Washington State University. *Saccharomyces cerevisiae* train ANY119 was a generous gift from Dr. S. Ferro-Novick, Howard Hughes Medical Institute, Yale University (Jiang, Y., Proteau, P., Poulter, D. and Ferro-Novick, S. (1995) *J. Biol. Chem.,* 270:21793–21799), and the expression strain INVSc1 was purchased from Invitrogen. The yeast expression vector pYeDP60 (Pompon, D., Benedicte, L., Bronine, A. and Urban, P. (1996) *Methods Enzymol.,* 272:51–64) was kindly provided by Dr. D. Pompon, CNRS, Université Pierre et Marie Curie, Gif-sur-Yvette, France.

A phage cDNA library from induced *T. canadensis* cells was prepared in λPG15. Total RNA was isolated using an RNA Maxi kit (Qiagen) from 14-day-old suspension cell cultures which had been induced with 200 μM methyl jasmonate 7 d prior to harvest by filtration. PolyA⁺ RNA was prepared by chromatography on oligo(dT)-cellulose (Pharmacia Biotech, Piscataway, N.J.). The cDNA library was synthesized using a λZAP-cDNA synthesis kit and ZAP-cDNA gigapack III gold cloning kit (Stratagene) by following the manufacturer's instructions, except that λPG15 replaced λZAP as the cloning vector.

A geranylgeranyl diphosphate synthase cDNA was cloned in the following manner. An initial PCR product was amplified using 150 pmol/reaction of a reverse degenerate primer (SEQ ID NO:3), which corresponded to part of a specific amino acid sequence which was conserved among certain acetyltransferase enzymes. This primer fortuitously hybridized to two different regions of a geranylgeranyl diphosphate synthase mRNA. PCR was carried out by heating the reaction mixture to 94° C. for 1 minute, lowering the temperature to 42° C. for 1 minute, then raising the temperature to 74° C. for 2 minutes. This temperature profile was repeated for 32 cycles. The resulting 861 bp fragment was ligated into pCR 2.1 Topo (Invitrogen Corporation, San Diego, Calif.) and the recombinant vector was transformed into *E. coli* XL1-Blue cells. Forty-five positive colonies were isolated from which plasmids were purified then sequenced using Amplitaq DNA polymerase and FS cycle sequencing on an ABI prism™ 373 DNA sequencer. It was found that only one isolated plasmid contained an insert sequence (SEQ ID NO:4) resembling geranylgeranyl diphosphate synthases from angiosperm plant species (translated Blast score of $1.0 \times 10^{-46}$). When compared to other GGPP synthase sequences, this clone (SEQ ID NO:4) was found to encode the first 194 amino acids of the translated protein in addition to 279 bp of the 5'-UTR.

A 583 bp portion of the initial 861 bp PCR product (extending from nucleotide 279 to nucleotide 861 of the cDNA sequence set forth in SEQ ID NO:4) was used as a hybridization probe to obtain a full-length geranylgeranyl diphosphate synthase cDNA sequence. Thus, a nondegenerate forward primer (SEQ ID NO:5) and a nondegenerate reverse primer (SEQ ID NO:6) were designed which corresponded to nucleotides 279 to 300, and 839 to 861, respectively, of the 861 bp cDNA sequence set forth in SEQ ID NO:4. Nondegenerate forward primer (SEQ ID NO:5) and nondegenerate reverse primer (SEQ ID NO:6) were used to amplify the intervening 583 bp region of the 861 bp cDNA sequence set forth in SEQ ID NO:4 by using approximately $1.0 \times 10^8$ molecules of the 861 bp fragment (SEQ ID NO:4) as template along with 5 pmol of each of nondegenerate forward primer (SEQ ID NO:5) and nondegenerate reverse primer (SEQ ID NO:6) in a 100 μl PCR reaction. The temperature profile and cycling conditions were as given above, except that the annealing temperature was raised from 42° C. to 50° C.

The resulting, gel purified, amplified cDNA fragment was then labeled with [α-³²P]ATP by the random hexamer method (Sambrook, J., Fritsch, E. F. and Maniatis, T. (1989) *Molecular Cloning: A Laboratory Manual,* 2nd ed., Cold Spring Harbor Laboratory, Cold Spring Harbor, N.Y.) and used to probe the *T. canadensis* cDNA library, containing approximately 80,000 independent clones. After two rounds of purification, 16 positive clones were excised, in vivo, as the plasmid pYPGE15 by infecting *E. coli* JM109 (λCC). Sequencing revealed that five of the 16 independent isolates each encoded a protein which, based on sequence comparison to other reported GGPP synthases (comparison at the protein level by translated Blast search gave a smallest sum probability of $1.1 \times 10^{-140}$), was identified as geranylgeranyl diphosphate synthase.

The sequence of four of the five cDNA clones was identical and is set forth in SEQ ID NO:1. One full-length coding region, free of stop codons, was found beginning at a methionine codon beginning 308 bp from the 5'-terminus of the sequence set forth in SEQ ID NO:1, and ending at a UGA codon at nucleic acid residues 1487 to 1489 of the sequence set forth in SEQ ID NO:1, thereby yielding a coding region of 1182 bp with a 5'-UTR of 308 bp and a 3'-UTR of approximately 400 bp.

When compared with other reported, plant-derived GGPP synthases, the deduced amino acid sequence of this gymnosperm enzyme open reading frame shows reasonable similarity throughout nearly the entire coding region, including the conserved aspartate and arginine residues which have been shown to be important in substrate binding and catalysis (Ashby, M. N. and Edwards, P. A. (1990) *J. Biol. Chem.,* 265:13157–13164; Joly, A. and Edwards, P. A. (1993) *J. Biol. Chem.,* 268:26983–26989; Tarshis, L. C., Proteau, P. J., Kellogg, B. A., Sacchettini, J. C. and Poulter, C. D. (1996) *Proc. Natl. Acad. Sci. USA,* 93:15018–15023; Song, L. and Poulter, C. D. (1994) *Proc. Natl. Acad. Sci. USA,* 91:3044–3048). Pairwise comparisons of the *T. canadensis* GGPP synthase (SEQ ID NO:2) with the corresponding sequences from a variety of other plant species reveal amino acid identities in the range of 45 to 64%. It is important to note, however, that the majority of the putative GGPP synthase clones from other plants have been identified only by sequence comparison and not by functional expression of the relevant activity. Although it seems likely that the clones that have not been authenticated by expression do encode GGPP synthases, evolutionary studies suggest that short chain prenyltransferases can not be easily grouped by function based on sequence analysis alone (Chen, A., Kroon, P. A. and Poulter, C. D. (1994) *Protein Sci.,* 3:600–607). Of the six defined *Arabidopsis thaliana* GGPP synthase sequences, only two have been characterized biochemically (Zhu, X. F., Suzuki, K., Saito, T., Okada, K., Tanaka, K., Nakagawa, T., Matsuda, H. and Kawamukai, M. (1997) *Plant Mol. Biol.*, 35:331–341; Zhu, X. F., Suzuki, K., Okada, K., Tanaka, K., Nakagawa, T., Kawamukai, M. and Matsuda, H. (1997) *Plant Cell Physiol.*, 38:357–361), and of the remaining GGPP synthase cDNAs of plant origin, only those from *Capsicum annuzm* (Kuntz, M., Römer, S., Suire, C., Hugueney, P., Weil, J. H., Schantz, R. and Camara, B. (1992) *Plant J.*, 2:25–34) and *Sinapis alba* (Bonk, M., Hoffman, B., Von Lintig, J., Schledz, M., Al-Babili, S., Hobeika, E., Kleinig, H. and Beyer, P. (1997) *Eur. J Biochem.*, 247:942–950) have been confirmed by functional expression of prenyltransferase activity.

Figure 3:
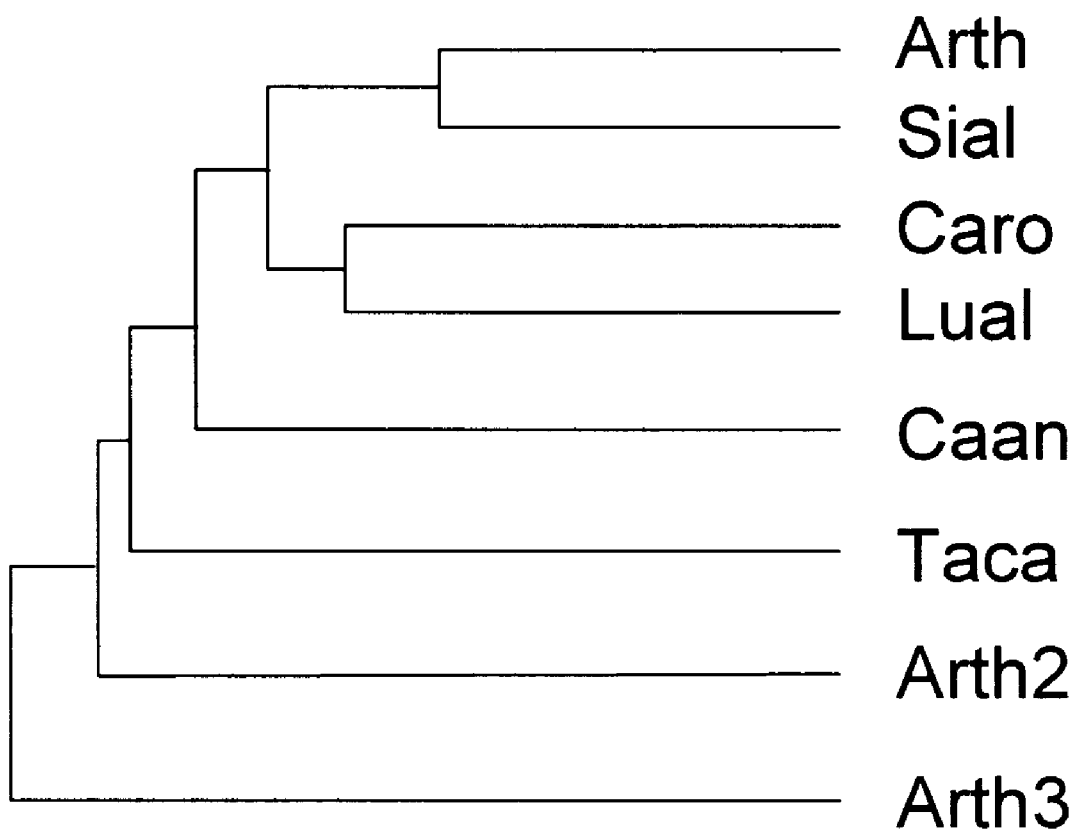
FIG. 3 shows the relationship of eight plant-derived GGPP synthase sequences based on amino acid similarity, as described in Example 1. Species abbreviations and Genbank accession numbers are: Arth, *Arabidopsis thaliana*, Z99708; Arth2, *A. thaliana* sequence 2, D85029 (Zhu, X. F., Suzuki, K., Okada, K., Tanaka, K., Nakagawa, T., Kawamukai, M. and Matsuda, H. (1997) *Plant Cell Physiol.*, 38:357–361); Arth3, *A. thaliana* sequence 3, L40577 (Scolnik, P. A. and Bartley, G. E. (1995) *Plant Physiol.*, 108:1343.); Caan, *Capsicum annuum*, X80267, (Kuntz, M., Römer, S., Suire, C., Hugueney, P., Weil, J. H., Schantz, R. and Camara, B. (1992) *Plant J.*, 2:25–34); Caro, *Catharanthus roseus*, X92893 (Bantignies, B., Liboz, T. and Ambid, C. (1996) *Plant Physiol.*, 110:336); Lual, *Lupinus albus*, U15778 (Aitken, S. M., Attucci, S., Ibrahim, R. K. and Gulick, P. J. (1995) *Plant Physiol.*, 108:837–838); Sial, *Sinapis alba*, X98795 (Bonk, M., Hoffman, B., Von Lintig, J., Schledz, M., Al-Babili, S., Hobeika, E., Kleinig, H. and Beyer, P. (1997) *Eur. J. Biochem.*, 247:942–950.); and Taca, *Taxus canadensis*, as reported herein.

Evaluation of the relatedness of the GGPP synthases of plant origin (FIG. 3) indicates that the GGPP synthase sequence disclosed herein (SEQ ID NO:2), the first GGPP synthase sequence from a gymnosperm, bears a closer relationship to GGPP synthases from angiosperms than do two of the clones from *A. thaliana*, Arth2 and Arth3. This is due not only in part to the highly variable transit peptide region characteristic of these enzymes (Chen, A., Kroon, P. A. and Poulter, C. D. (1994) *Protein Sci.*, 3:600–607), but also to the fact that the Arth3 sequence lacks some key areas of amino acid conservation.

EXAMPLE 2

Generation of GGPP Synthase Expression Constructs and Complementation Assays in Yeast All known GGPP synthase sequences of plant origin appear to encode a transit peptide for organellar compartmentation of this prenyltransferase (Kleinig, H. (1989) *Annu. Rev. Plant Physiol. Plant Mol. Biol.*, 40:39–59; Chen, A., Kroon, P. A. and Poulter, C. D. (1994) *Protein Sci.*, 3:600–607). Many of these enzymes have been shown to be localized to plastids (Kuntz, M., Römer, S., Suire, C., Hugueney, P., Weil, J. H., Schantz, R. and Camara, B. (1992) *Plant J.*, 2:25–34; Bonk, M., Hoffman, B., Von Lintig, J., Schledz, M., Al-Babili, S., Hobeika, E., Kleinig, H. and Beyer, P. (1997) *Eur. J. Biochem.*, 247:942–950; Laferrière, A. and Beyer, P. (1991) *Biochem. Biophys. Acta*, 1077:167–172), although at least one, from *A. thaliana*, is targeted specifically to mitochondria (Zhu, X. F., Suzuki, K., Saito, T., Okada, K., Tanaka, K., Nakagawa, T., Matsuda, H. and Kawamukai, M. (1997) *Plant Mol. Biol.*, 35:331–341). Since it was assumed that the *T. canadensis* GGPP synthase cDNA likewise would encode an organellar transit peptide, and that the resulting preprotein would likely be less catalytically efficient than the mature, proteolytically processed form, the deduced amino acid sequence of the putative, Taxus GGPP synthase (SEQ ID NO:2) was compared to angiosperm GGPP synthase sequences in order to identify the N-terminal and C-terminal boundaries of the mature protein.

The amino acid sequence comparisons were made using the GCG (Genetics Computer Group (1994) Program Manual for the Wisconsin Package, Version 8, Genetics Computer Group, 575 Science Drive, Madison, Wis.) program Pileup with a blosum 62 comparison matrix. The gap creation and gap extension penalties were 12.0 and 4.0, respectively. These sequence alignments were displayed using the EGCG (Program Manual for the EGCG Package, Peter Rice, The Sanger Centre, Hinxton Hall, Cambridge, CB 101 RQ, England) program Prettybox with the plurality set at 4.1. Thus, comparison of plant-derived GGPP synthase amino acid sequences with the deduced *T. canadensis* protein (SEQ ID NO:2) showed that high-level conservation begins at $F^{99}$ of the amino acid sequence set forth in SEQ ID NO:2, indicating a logical truncation site at nucleotide 295 ($Tr^{295}$) of the GGPP synthase cDNA sequence set forth in SEQ ID NO:2; a second site (at nucleotide 313, $Tr^{313}$) was chosen (six residues downstream) because of the location of the convenient $M^{105}$ residue.

PCR primers containing a KpnI site (SEQ ID NO:7) or a BamHI site (SEQ ID NO:8) were designed to the 3'- and 5'-termini, respectively, of the presumptive full-length coding sequence (SEQ ID NO:1). Additionally, a 5'-terminal primer (SEQ ID NO:9) was designed to correspond to a 5'-truncated version of the GGPP synthase protein sequence set forth in SEQ ID NO:2 beginning at $Tr^{295}$, while a second 5'-terminal primer (SEQ ID NO:10) was designed to correspond to a 5'-truncated version of the GGPP synthase protein sequence set forth in SEQ ID NO:2 beginning at $Tr^{313}$. The primers set forth in SEQ ID NO:9 and SEQ ID NO:10 were designed in order to express putative mature proteins devoid of the transit peptide. After amplification with Pfu DNA polymerase, the three cDNA fragments were ligated into PCR-Script CAM SK(+) (Stratagene), then sequenced to ensure that no errors had arisen during amplification. The BamHI/KpnI-digested fragment corresponding to each coding sequence was then subcloned into pYeDP60 under the control of the GAL10-CYC1 promoter.

The pYeDP60 constructs were transformed into the *S. cerevisiae* mutant ANY119 using the lithium acetate procedure (Treco, D. (1989) in *Current Protocols in Molecular Biology* (Ausubel, F. M., Brent, R., Kingston, R. E., Moore, D. D., Seidman, J. G., Smith, J. A. and White, T. J., Eds.), pp. 13.7.1–13.7.2, John Wiley and Sons, New York), and the transformed yeast were then plated on a synthetic medium containing glucose as the sole carbon source (but lacking uracil) and grown for 4 d at 25° C. Isolated colonies, corresponding to each construct, were then replica streaked onto SGI, N3 and SLI media and grown for 3, 5 or 7 d, respectively, at 25° C or 37° C.

SGI and SLI synthetic media contain, respectively, 20 g/liter glucose (G) or 20 g/liter galactose (L) in 1 g/liter bactocasamino acids (Difco), 6.7 g/liter yeast nitrogen base without amino acid (Difco), and 40 mg/liter DL-tryptophan. SGAI and SLAI are identical to SGI and SLI except that 30 mg/liter adenine is added. YPGE complete medium contains 5 g/liter glucose, 10 g/liter yeast extract (Difco), 10 g/liter bactopeptone (Difco Laboratories, Inc., Detroit, Mich.), and 3% (by vol) ethanol. YPG(A) and YPL(A), respectively, contain 20 g/liter glucose or 20 g/liter galactose in 10 g/liter yeast extract, 10 g/liter bactopeptone, and, when required, 30 mg/liter adenine (A).

The three pYeDP60/*T. canadensis* GGPP synthase constructs were introduced into and expressed in ANY119, an *S. cerevisiae* mutant that is defective for the β-subunit of type II geranylgeranyltransferase. This mutation is lethal at high temperature but can be complemented by increasing the expression level of GGPP synthase (Jiang, Y., Proteau, P., Poulter, D. and Ferro-Novick, S. (1995) *J. Biol. Chem.*, 270:21793–21799). To determine if the *T. canadensis* GGPP synthase forms could be functionally expressed in yeast at levels sufficient to rescue this mutant when grown at the restrictive temperature, the expression of the three constructs was tested on three different carbon sources that differentially regulate GAL10-CYC1 promoter activity (Pompon, D., Benedicte, L., Bronine, A. and Urban, P. (1996) *Methods Enzymol.*, 272:51–64). This promoter is repressed in the presence of glucose (SGI medium), induced in the presence of galactose (SLI medium) and behaves in a neutral manner with glycerol as the sole carbon source (N3 medium).

Isolated transformants bearing each construct (full-length, $Tr^{295}$ and $Tr^{313}$), as well as the empty vector (control), were streaked on each carbon source medium and grown at the permissive temperature (25° C.) and the restrictive temperature (37° C.). At 25° C., each of the transformants grew on SGI and N3 medium after 3d and 5 d, respectively. However, on SLI medium, modest growth was observed only for the control and $Tr^{313}$ constructs, even after 7 d. From these results, it was concluded that ANY119 uses galactose only poorly as a sole carbon source. At 37° C., no growth was observed on SLI after 7 d; however, on both SGI (3 d) and N3 (5 d), only transformants harboring the full-length and $Tr^{295}$ constructs showed growth, while no growth was exhibited by transformants bearing the control and $Tr^{313}$ constructs. These results indicate that both the full-length GGPP synthase clone and the $Tr^{295}$ truncation rescue the bet2-1 mutant and that, even under repressed conditions (on SGI), enough leaky expression of GGPP synthase occurs to complement the mutation.

To test the expression of GGPP synthase on galactose as carbon source, each construct was transformed into a yeast strain (INVSc1) that metabolizes this sugar efficiently. These INVSc1 transformants were plated on SLI medium and grown at 30° C. for 3 d, whereupon luxuriant growth was observed for the control yeast and that bearing the $Tr^{313}$ construct, whereas only scanty growth was seen for the yeast bearing the full-length construct; that bearing the $Tr^{295}$ construct did not grow at all. These results indicate that, when high level expression of the heterologous GGPP synthase is fully induced, the gene is toxic. Furthermore, it can be concluded from both these and the above results that the full-length and $Tr^{295}$ constructs yield active GGPP synthase but that the shorter $Tr^{313}$ truncation construct does not.

EXAMPLE 3

Analysis of Expression Level and Toxicity of Taxus GGPP Synthase in Yeast

To determine the amount of GGPP synthase protein expressed from each construct, the corresponding transformed INVSc1 cells were grown in large scale YPGE liquid cultures and induced by the addition of galactose, and the soluble proteins were extracted and analyzed by SDS-PAGE. Colonies were inoculated into 30 ml of SGI medium and grown at 30° C. for 20 h. One liter of YPGE medium (1% yeast extract, 1% peptone, 0.5% glucose and 3% ethanol) was then inoculated with 20 ml of the SGI starter culture which was grown at 28° C. to a concentration of $1.2 \times 10^8$ cells/ml. The cultures were then adjusted to 2% (v/v) galactose and grown to a final density of approximately $4.5 \times 10^8$ cells/ml. The cells were harvested by centrifugation at 6700 g for 5 min, the supernatant was decanted, and the cell pellets were resuspended in 200 ml of 50 mM Tris buffer (pH 7.6) containing 100 mM KCl.

After centrifugation as above, the cell pellet was resuspended in 80 ml of ice cold 50 mM Tris (pH 7.6) containing 10% (v/v) glycerol, 10 mM $MgCl_2$, 5 mM DTT, and 1 μg/ml leupeptin (extraction/assay buffer). All subsequent operations were conducted at 0–4° C. Cells were disrupted with 150 ml glass beads using a Biospec Bead-Beater operated at 90 V for 5 min, and the resulting debris was removed by centrifugation at 3000 g for 20 min to yield a supernatant that was further clarified by centrifugation at 31,000 g for 20 min. The resulting supernatant was used as the enzyme source. Protein concentration was estimated by the method of Bradford (Bradford, M. M. (1976) *Anal. Biochem.*, 72:248–254), and the preparations were evaluated by SDS-PAGE on 10% acrylamide gels (2.1 mg total protein per lane) by the method of Laemmli (Laemmli, U. K. (1970) *Nature,* 227:680–685) followed by silver staining (Blum, H., Beir, H. and Gross, H. J. (1987) *Electrophoresis,* 8:93–99). The size of the presumptive, mature, recombinant, homodimeric enzyme was determined by gel permeation chromatography using a Pharmacia 16/60 Superdex G-75 column eluted with 25 mM Mopso (pH 7.0) containing 10% (v/v) glycerol, 1% (v/v) ethylene glycol and 100 mM NaCl at a flow rate of 1 ml/min.

A prominent protein band at about 32 kDa was observed only in the extract of the yeast harboring the $Tr^{295}$ construct; this size corresponds to the calculated monomeric size of 32.1 kDa for this truncated GGPP synthase. None of the transformants bearing other constructs yielded extracts with protein banding patterns appreciably different from that of the empty vector control. These results suggest that the $Tr^{295}$ construct is expressed at a high level but that the $Tr^{313}$ truncation and full-length constructs are not sufficiently expressed to afford an observable soluble protein.

The toxicity of the constitutively expressed, recombinant GGPP synthase gene in yeast and in *E. coli* parallels the in vitro activity of the enzyme expressed in the truncation series. Thus, the $Tr^{295}$ construct is extremely toxic, the full-length gene (encoding the preprotein) causes a noticeable reduction in growth, whereas the $Tr^{313}$ construct has no effect on cell growth. This toxicity is not observed when the corresponding transformed yeast are grown on glucose or glycerol (uninduced condition), but only when the gene is actively expressed by growth under inducing conditions with galactose as the carbon source. The overexpression of this gene to produce a functional GGPP synthase probably interferes with metabolism by depleting intracellular pools of FPP, via diversion to GGPP, and thus limiting sterol biosynthesis. Similarly, in *E. coli* when $Tr^{295}$, or the full-length GGPP synthase clone (SEQ ID NO:1), is expressed under a strong constitutive promoter the cells will not grow. The vector used in these *E. coli* transformation experiments was pYPGE15, the plasmid derived from λPG15.

Conversely, the complementation of the ANY119 bet2-1 yeast mutant by GGPP synthase is thought to occur by an increase in the intracellular concentration of GGPP (Jiang, Y., Proteau, P., Poulter, D. and Ferro-Novick, S. (1995) *J. Biol. Chem.,* 270:21793–21799). Interestingly, complementation was observed when the cells were plated on medium containing glucose as the sole carbon source, conditions under which the GAL10-CYC1 hybrid promoter is thought to be fully repressed (Pompon, D., Benedicte, L., Bronine, A. and Urban, P. (1996) *Methods Enzymol.,* 272:51–64). Thus, it appears that there is sufficient leaky expression of this gene to rescue the mutant under these conditions. The fact that Jiang et al. (Jiang, Y., Proteau, P., Poulter, D. and Ferro-Novick, S. (1995) *J. Biol. Chem.,* 270:21793–21799) demonstrated that the level of mutant complementation was dependent on the level of expression of a cloned yeast GGPP synthase, combined with the tight regulation provided by the GAL10-CYC1 promoter, suggests that expression of even very low levels of the $Tr^{295}$ construct affords an enzyme with adequate catalytic activity to rescue the mutant.

EXAMPLE 4

Product Identification and Characterization of Recombinant GGPP Synthase

To confirm that the protein encoded by the isolated *T. canadensis* cDNA was indeed geranylgeranyl diphosphate synthase, prenyltransferase assays were performed with the corresponding yeast extracts using [4-$^{14}$C]IPP and FPP as co-substrates under conditions where background activity from endogenous yeast GGPP synthase was negligible.

The standard assay for prenyltransferase activities was performed with 21 mg protein in a total volume of 100 ml of the extraction/assay buffer disclosed in Example 3. DMAPP (200 mM), GPP (200 mM) or FPP (200 mM), and the homoallylic co-substrate [4-$^{14}$C]IPP (50 mM), were added as appropriate for the assay, and the reaction mixtures were incubated at 31° C. for 20 min. The reaction was quenched by the addition of 300 mil of methanol:conc. HCl (4:1, v/v), and the allylic diphosphate products were solvolyzed (50, 51) upon further incubation at 42° C. for 20 min. The resulting solvolysis products were extracted twice with 1 ml pentane, and were either analyzed by liquid scintillation counting (in toluene:ethanol (7:3, v/v) containing 0.4% Omnifluor (DuPont NEN); $^{14}$C counting efficiency=96.0%) or concentrated on ice under a gentle stream of Ar to ~100 ml for further analysis.

For radio-TLC analysis, samples were mixed with 10 mg each of geranylgeraniol (all trans), geranyllinalool (mixed geometric isomers), farnesol and geraniol and spotted on Whatman MKC 18F reversed phase plates that were developed with acetonitrile:acetone:water (15:4:1, v/v/v) and visualized with I$_2$vapor. Bands corresponding to the standards were scraped into scintillation vials for counting. For radio-GC analysis, the above pentane extract was diluted with 200 ml of an 8% ethereal solution of the internal standards before concentration on ice. Product identity was confirmed by radio-GC (Satterwhite, D. M. and Croteau, R. (1988) *J. Chromatogr.*, 452:61–73) coincidence with the authentic standard on a 12 ft x 0.125 in. polydimethylsiloxane column (15% SE-30 on 80/100-mesh Chromasorb WHP; (Alltech, Inc., Nicholasville, Ky.), with He as carrier and temperature programming from 150° C. (1 min hold) to 240° C. (20 min hold) at 8° C./min.

For kinetic evaluations, the protein concentrations and incubation times for the assays were reduced to 4 mg and 7.5 min, respectively, to ensure linearity, and the concentrations of IPP (0.5–100 mM), FPP (0.05–200 mM) and Mg$^{2+}$ (0.01–1000 mM) were independently varied in assays in which the remaining reactants were maintained at saturation. Double reciprocal plots were constructed for each data set and the equation of the best-fit line (r$^2$>0.97) was determined (KaleidaGraph, version 3.08, Synergy Software, Reading, Pa.). For evaluation of relative velocities, DMAPP, GPP and FPP were compared as the allylic co-substrate at concentrations of 12.5 mM and 25 mM.

Only the enzyme preparation from yeast expressing the Tr$^{295}$ construct was highly active; when compared on a protein basis, the preprotein (full-length construct) was only 12% as active as the truncated form expressed from Tr$^{295}$, whereas the enzyme expressed from truncation Tr$^{313}$ was not detectably active.

Expression of highly active *T. canadensis* GGPP synthase appears to be dependent on removal of the transit peptide in the Tr$^{295}$ construct. This truncation was designed based upon sequence homology, rather than upon predictive methods for the cleavage site (Keegstra, K., Olsen, J. J. and Theg, S. M. (1989) *Annu. Rev. Plant Physiol. Plant Mol. Biol.*, 40:471–501; von Heijne, G., Steppuhn, J. and Herrmann, R. G. (1989) *Eur. J. Biochem.*, 180:535–545). Even though the full-length preprotein was apparently much less active, and the Tr$^{313}$ truncated protein was apparently inactive, neither of these proteins was observed to be efficiently expressed, as determined by SDS-PAGE analysis of the protein extracts of the corresponding transformed yeast. Thus, because comparative specific activities could not be easily determined, it is premature to conclude that the preprotein is inherently less active than the processed, mature form, or that the truncation site of the Tr$^{313}$-expressed protein extends too far into the conserved region of the enzyme to yield a catalytically active species.

Figure 4:
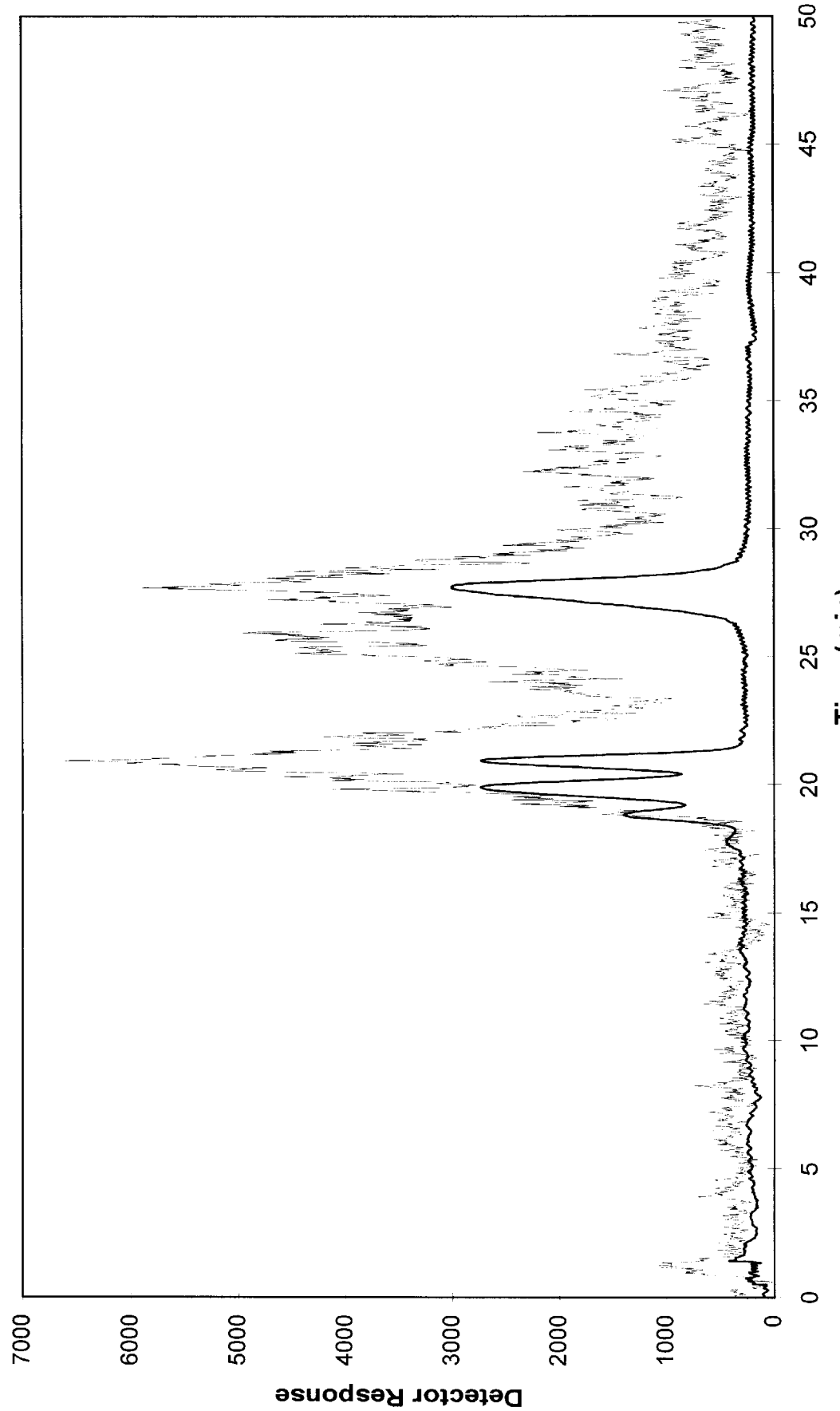
FIG. 4 shows a radio-GC analysis of the reaction product generated by *T. canadensis* GGPP synthase construct Tr$^{295}$ followed by acid-catalyzed solvolysis as described in Example 4. The smooth lower tracing indicates the elution pattern of the authentic standards geranyllinalool (mixed isomers, the all-trans-isomer elutes at 20.93 min) and geranylgeraniol (R$_t$=27.68 min). The radioactive component with R$_t$=25.93 min is consistent with the elution behavior of geranylnerol.

Analysis, by reversed phase TLC, of the solvolysis products of the prenyltransferase reaction (utilizing [4-$^{14}$C]IPP plus FPP as substrates) catalyzed by the truncated enzyme expressed from the Tr$^{295}$ construct revealed that 97% of the total radioactivity coincided with the geranylgeraniol and geranyllinalool standards (see FIG. 2), as expected. Radio-GC analysis (FIG. 4) of the reaction products indicated the presence of two components, coincident with all trans geranyllinalool (major component) and geranylgeraniol, respectively, and a third (middle peak) with relative retention time consistent with that of geranylnerol. This observed product distribution is consistent with that expected for the acid-catalyzed solvolysis of allylic diphosphates (Tidd, B. K. (1971) *J. Chem. Soc. (B)*, 1971:1168–1176), such as GGPP, confirming that a cDNA encoding GGPP synthase had been obtained.

Kinetic evaluation of the GGPP synthase by double reciprocal plotting afforded a K$_m$ value for IPP of 7 mM, for FPP of 6 mM, and for the required divalent metal ion (Mg$^{2+}$) of 35 mM; Mn$^{2+}$did not support catalysis by this enzyme. These K$_m$ values are in the range of those reported for other GGPP synthases, some of which, unlike this enzyme from Canadian yew, are able to utilize either Mn$^{2+}$or Mg$^{2+}$as cofactor although rarely with comparable efficiency (West, C. A., Dudley, M. W. and Dueber, M. T. (1979) *Recent Adv. Phytochem.*, 13:163–198; West, C. A. (1981) in Biosynthesis of Isoprenoid Compounds (Porter, J. W. and Spurgeon, S. L., Eds.), Vol. 1, pp. 375–411, Wiley, New York, N.Y.; Gershenzon, J. and Croteau, R. (1993) in Lipid Metabolism in Plants (Moore, T. S., Jr., Ed.), pp. 339–388, CRC Press, Boca Raton, Fla.; Ogura, K. and Koyama, T. (1998) *Chem. Rev.*, in press). The relative velocities of the reaction with the three possible allylic co-substrates, DMAPP, GPP, and FPP, were examined at concentrations of 12.5 and 25 mM, with IPP and Mg$^{2+}$concentrations at saturation, and shown to be DMAPP=33%, FPP=66%, and GPP =100%. The utilization of the C$_5$ and C$_{10}$ allylic co-substrates, in addition to FPP, has been observed previously with other GGPP synthases which, based on the above properties, the enzyme from *T. canadensis* appears to resemble (Laferrière, A. and Beyer, P. (1991) *Biochem. Biophys. Acta*, 1077:167–172; Ogura, K. and Koyama, T. (1998) *Chem. Rev.*, in press; Brinkhaus, F. L. and Rilling, H. C. (1988) *Arch. Biochem. Biophys.*, 266:607–612). Some GGPP synthases (i.e., farnesyl transferase) do not utilize DMAPP, and use GPP as the allylic cosubstrate only inefficently (West, C. A., Dudley, M. W. and Dueber, M. T. (1979) *Recent Adv. Phytochem.*, 13:163–198).

Gel permeation chromatography on a calibrated Superdex G-75 (Pharmacia, Biotech, Piscataway, N.J.) column yielded an elution volume corresponding to a molecular weight of approximately 60,000 for the GGPP synthase Tr$^{295}$ truncated protein which, along with the predicted size of 32.1 kDa and the results of SDS-PAGE, indicate that the enzyme exists as a functional dimer. This observation is consistent with the size and the subunit architecture determined for the native GGPP synthases from other sources (West, C. A., Dudley, M. W. and Dueber, M. T. (1979) *Recent Adv. Phytochem.*, 13:163–198; Laferrière, A. and Beyer, P. (1991)

Biochem. Biophys. Acta, 1077:167–172; Dogbo, O. and Camara, B. (1987) Biochem. Biophys. Acta, 920:140–148; Ogura, K. and Koyama, T. (1998) Chem. Rev., in press).

EXAMPLE 5

Changes in GGPP Synthase and Taxadiene Synthase Enzyme Activity and mRNA Levels in Response to Methyl Jasmonate Suspension cell cultures were treated with methyl jasmonate 7 d after subculture and harvested at 8, 12, 24, 48 or 168 h after elicitation, or immediately before induction. During this 7 d induction period, the wet cell mass increased by about 10% and the paclitaxel concentration in the medium (where the majority of the taxoids accumulate) rose from 2.5 mg/l to 32 mg/l, with the greatest increase occurring after 48 h. The concentration of paclitaxel was measured by calibrated HPLC with UV detection as described in Hezari et al, Arch. Biochem. Biophys., 337:185–190 (1997).

The regulation of gene expression over the time course of induction was examined by RNA-blot analysis of total RNA isolated from the cells using probes for GGPP synthase and taxadiene synthase, the first two enzymes of the paclitaxel pathway leading from primary metabolism (i.e., from IPP and DMAPP). Total RNA was isolated from T. canadensis suspension cell cultures using the method set forth in Example 1. Equivalent amounts of RNA (14.5 mg) from cells that had been harvested 8, 12, 24, 48, and 168 h after methyl jasmonate induction, as well as RNA isolated from non-induced cells (0 h), were separated by electrophoresis on a formaldehyde-denaturing agarose gel, along with RNA size standards (Promega Corporation, Madison, Wis.). The separated RNA was blotted to nylon membrane by capillary action and then fixed by UV irradiation. Radiolabeled probes corresponding to the full length GGPP synthase coding region (nucleotide 308 to nucleotide 1489 of the nucleic acid sequence set forth in SEQ ID NO:1), and to an internal fragment (nucleotides 173 to 1875 inclusive) of the taxadiene synthase cDNA reported in Wildung, M. R. and Croteau, R. (1996) J. Biol. Chem., 271:9201–9204, generated by PCR, were synthesized using a Ready-To-Go probe synthesis kit (Pharmacia Biotech, Piscataway, N.J.), then purified using a Sephadex G-50 spin column (Pharmacia). The blot was incubated sequentially with each probe for 16 h at 65° C., then washed twice with 2×SSC at room temperature, and then thrice with 0.5×SSC at 65° C. The blot was imaged using a Bio-Rad GS-525 Molecular Imager® System and Molecular Analyst version 2.1 software.

A rapid increase in the steady state mRNA levels for both GGPP synthase and taxadiene synthase was observed at 8 h, and these levels remained significantly elevated through at least 48 h before decline. However, even after 168 h, the steady state levels of these transcripts were discernibly higher than the non-induced control.

The same T. canadensis cell cultures used for RNA blot analysis were also used to determine the relative activities of GGPP synthase and taxadiene synthase over the course of methyl jasmonate induction of paclitaxel biosynthesis. One gram (fresh wt.) of cells corresponding to each time point were ground to a fine powder in liquid nitrogen then placed in 5 ml of 30 mM Hepes buffer (pH 7.9) containing 15 mM MgCl$_2$, 5 mM sodium ascorbate, 5 mM Na$_2$S$_2$O$_5$, 5 mM dithiothreitol, 10% (v/v) glycerol, 1% (w/v) polyvinylpyrrolidone (M$_r$~10,000) and 0.3 g each of polyvinylpolypyrrolidone and Amberlite XAD-4, and agitated gently for 30 min at 4° C. Particulate material and cellular debris were removed from the homogenates by centrifugation, first at 3000 g, then at 31,000 g, for 20 min at 4° C. Protein concentration in the supernatant used as the enzyme source was estimated by the method of Bradford (Bradford, M. M. (1976) Anal. Biochem. 72:24814 254).

GGPP synthase activity was determined by the standard prenyltransferase assay described in Example 4, except that 100 μl of crude extract (150 μg protein) isolated from T. canadensis cell cultures was used as the enzyme source and the reactions were incubated for 10 min. Taxadiene synthase activity was determined by measuring the Mg$^{2+}$-dependent conversion of [1-$^3$H$_1$]geranylgeranyl diphosphate (15 μM) to the olefin product as described in Hezari, M., Lewis, N. G. and Croteau, R. (1995) Arch. Biochem. Biophys., 322:437–444; Hezari, M., Ketchum, R. E. B., Gibson, D. M. and Croteau, R. (1997) Arch. Biochem. Biophys., 337:185–190. In this assay, 500 μl of the crude extract (750 μg protein) was incubated at 3 1° C. for 1 h.

Figure 5:
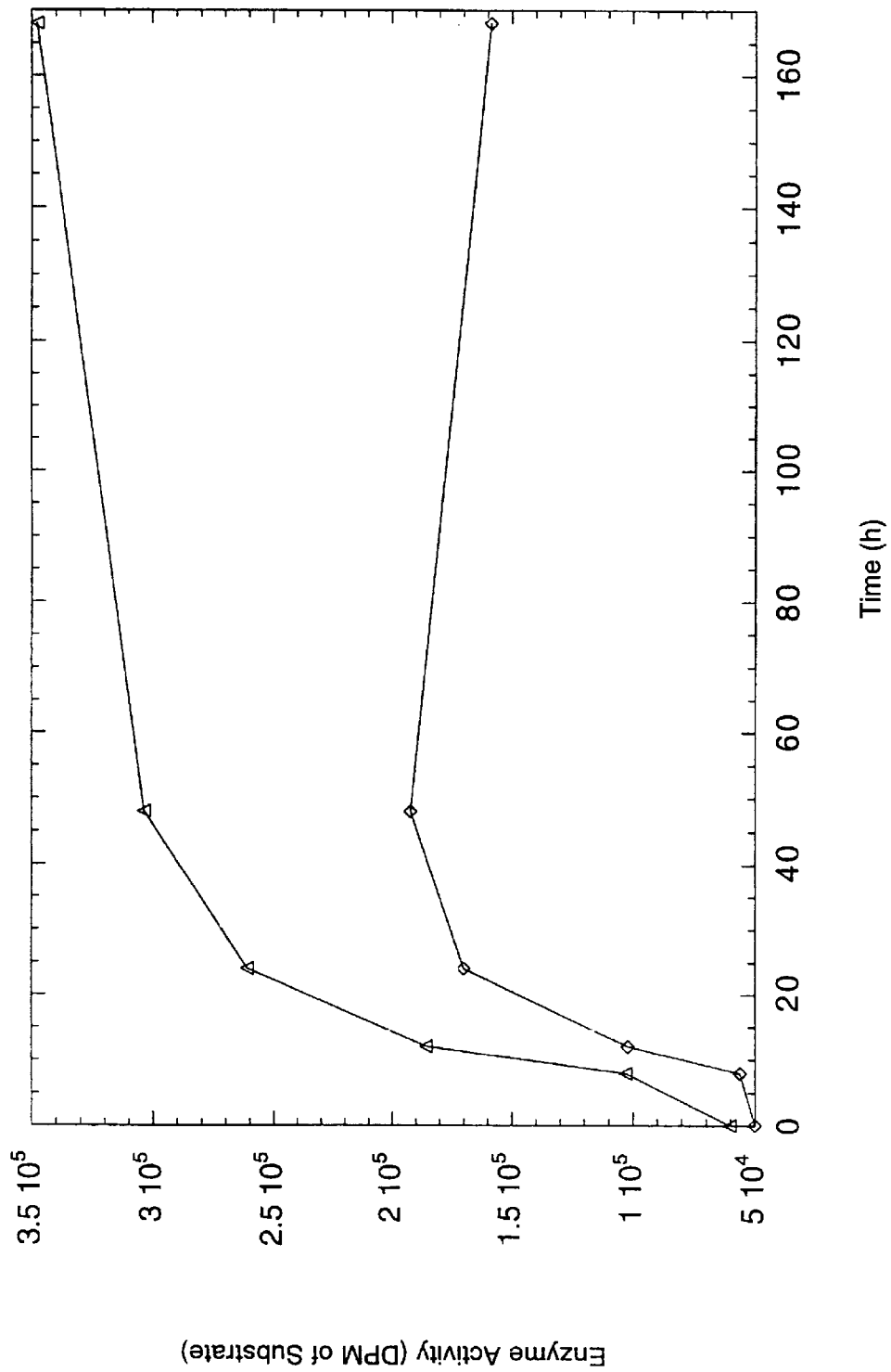
FIG. 5 shows the time course of GGPP synthase (the line marked with triangles) and taxadiene synthase (the line marked with diamonds) activity measured in extracts of *T. canadensis* suspension cell cultures following induction with methyl jasmonate, as described in Example 5. The 0 h time point corresponds to the enzyme activities from cells harvested immediately prior to methyl jasmonate addition.

Activity for the first two pathway enzymes also increased over time in response to methyl jasmonate (FIG. 5). Following a short induction period, the activity levels for both GGPP synthase and taxadiene synthase rose steadily to 48 h, with relatively little change thereafter. This kinetic behavior is consistent with the initiation of steady production rates of paclitaxel at about 48 h. In comparing the northern blot analyses to the enzyme activity curves (FIG. 5), it is apparent that there is a delay of at least a day between the peak steady state mRNA levels and the peak of activities for both corresponding synthases, which may suggest that these messages are translated with low efficiency or that additional levels of post-transcriptional or post-translational control are in operation. The time frame for this induced response of Taxus cells to methyl jasmonate is comparable to that of elicitor-induced sesquiterpenoid phytoalexin production in tobacco (Facchini, P. J. and Chappell, J. (1992) Proc. Natl. Acad. Sci. USA, 89:11088–11092; Vögeli, U. and Chappell, J. (1988) Plant Physiol., 88:1291–1296; Threlfall, D. R. and Whitehead, I. M. (1988) Phytochemistry, 27:2567–2580) or diterpenoid phytoalexin production in castor bean (West, C. A., Lois, A. F., Wickham, K. A. and Ren, Y. -Y. (1990) Recent Adv. Phytochem., 24:219–248), and only slightly faster, but of shorter duration, than wound-induced oleoresin terpene production in grand fir (Steele, C. L., Katoh, S., Bohlmann, J. and Croteau, R. (1998) Plant Physiol., 116, 1497–1504).

In comparing the activity levels of GGPP synthase and taxadiene synthase derived from non-induced and induced cells (FIG. 5), it is apparent that GGPP synthase is present in substantial excess. However, it should be noted that these synthase activities were measured in crude extracts which may not accurately reflect in vivo differences in activity levels. Nevertheless, based on the magnitude of the difference, it seems unlikely that the prenyltransferase is rate limiting in either constitutive or induced paclitaxel production. In considering future approaches for biological production of the drug, however, the fact that the T. canadensis GGPP synthase cDNA is cloned and can be functionally expressed in a eukaryotic host does allow for the eventual possibility of increasing paclitaxel yields in genetically engineered Taxus cells in which genes for slow steps of the pathway are overexpressed and where the maintenance of a high level supply of GGPP may be required.

EXAMPLE 6

Isolation of a GGPP Synthase cDNA Clone (SEQ ID NO:11) from *Taxus cuspidata*

A phage cDNA library from induced *T. cuspidata* cells was prepared in λPG15. Total RNA was isolated using an RNA Maxi kit (Qiagen N. V., Amsterdam, The Netherlands) from 14-day-old suspension cell cultures which had been induced with 200 μM methyl jasmonate 7 d prior to harvest by filtration. PolyA+ RNA was prepared by chromatography on oligo(dT)-cellulose (Pharmacia Biotech). The cDNA library was synthesized using a λZAP-cDNA synthesis kit and ZAP-cDNA gigapack III gold cloning kit (Stratagene) by following the manufacturer's instructions, except that λPG1 5 replaced λZAP as the cloning vector.

A partial-length cDNA clone (SEQ ID NO:11) encoding a GGPP synthase (SEQ ID NO:12) was amplified by PCR using the primers set forth in SEQ ID NO:7 and SEQ ID NO:9. The *T. cuspidata* GGPP synthase partial cDNA (SEQ ID NO:11) encodes the mature form of the *T. cuspidata* GGPP synthase enzyme, i.e., the form of the enzyme that lacks the transit peptide at the amino terminus. The deduced amino acid sequence of the *T. cuspidata* enzyme (SEQ ID NO:12) is identical to the mature form of the *T. canadensis* enzyme. At the nucleotide level, the *T. cuspidata* cDNA (SEQ ID NO:11) is almost identical (98.6% similarity) to the *T. canadensis* GGPP synthase cDNA (SEQ ID NO:1).

EXAMPLE 7

Physical Properties of GGPP Synthase Proteins Isolated from Various Taxus Species Table 1 sets forth certain physical properties of GGPP synthase proteins isolated from the following Taxus species: *T. canadensis; T. brevifolia; T. cuspidata* and *T. baccata*.

TABLE 1

| Native Molecular Weight of Homodimer | 60,000 ± 2,000 |
|---|---|
| $Km^{IPP}$ | 7 ± 1 μM |
| $Km^{FPP}$ | 6 ± 1 μM |
| $Km^{Mg^{2+}}$ | 35 ± 3 μM |
| pH optimum | 7.5 ± 0.2 |
| Cosubstrate Utilization Ratio GPP:FPP:DMAP | 3:2:1 |

Some authorities regard all eight species within the genus Taxus, including the foregoing Taxus species, as being so similar that they are not distinct species, but are actually geographic variants of the same species. See, *The Yew Tree: Biography of a Species*, page 57, H. Hartzell Jr., Hulogosi Press, Eugene, Oreg. (1991); Voliotis, D. *Historical and Environmental Significance of the Yew (Taxus baccata* L.). Israel Journal of Botany, 35:1–58 (1986); Bolsinger, C. and Jaramillo, A. E., "*Taxus brevifolia Nutt. Pacific Yew*" in Silvics of Forest Trees of North America. Pacific Northwest Research Station, pp 15–24 (1990).

EXAMPLE 8

Hybridization of *T. canadensis* GGPP Synthase cDNA (SEQ ID NO:1) to Other Nucleic Acid Sequences of the Present Invention Utilizing Northern blot analysis, the GGPP synthase cDNA clone set forth in SEQ ID NO:1, or its complementary sequence, is capable of hybridizing to other nucleic acids of the present invention under the following conditions: hybridization in 5×SSC at 65° C. for 16 hours. Once hybridized under the foregoing hybridization conditions, the GGPP synthase cDNA clone set forth in SEQ ID NO:1, or its complementary sequence, is capable of remaining hybridized to other nucleic acids of the present invention under the following wash conditions: two washes in 2×SSC at room temperature (20° C. to 25° C.) for 15 minutes per wash, followed by two washes in 0.2×SSC at 65° C. for 20 minutes per wash.

When screening a cDNA library, the GGPP synthase cDNA clone set forth in SEQ ID NO:1, or its complementary sequence, is capable of hybridizing to other nucleic acids of the present invention under the following conditions: hybridization in 3×SSC at 65° C. for 16 hours. Once hybridized under the foregoing hybridization conditions, the GGPP synthase cDNA clone set forth in SEQ ID NO:1, or its complementary sequence, is capable of remaining hybridized to other nucleic acids of the present invention under the following wash conditions: two washes in 2×SSC at room temperature (20° C. to 25° C.) for 20 minutes per wash, followed by one wash in 0.5×SSC at 55° C. for 30 minutes.

The ability of the nucleic acid molecules of the present invention to hybridize, and to remain hybridized, to the nucleic acid sequence set forth in SEQ ID NO:1, or to the complementary sequence of the nucleic acid sequence set forth in SEQ ID NO:1, can be determined utilizing the technique of hybridizing radiolabelled nucleic acid probes to nucleic acids immobilized on nitrocellulose filters or nylon membranes as set forth, for example, at pages 9.52 to 9.55 of Molecular Cloning, A Laboratory Manual (2nd edition), J. Sambrook, E. F. Fritsch and T. Maniatis eds, the cited pages of which are incorporated herein by reference.

In addition to the nucleic acid sequences set forth in SEQ ID NO:1 and SEQ ID NO:11, examples of representative nucleic acid sequences of the present invention that encode a Taxus GGPP synthase and which hybridize to the complementary sequence of the nucleic acid sequence disclosed in SEQ ID NO:1 under the foregoing hybridization conditions (and which remain hybridized under any of the foregoing wash conditions) are set forth in SEQ ID NO:13; SEQ ID NO:15; SEQ ID NO:17; SEQ ID NO:19; SEQ ID NO:21; SEQ ID NO:23; and SEQ ID NO:25.

In addition to the protein sequences set forth in SEQ ID NO:2 and SEQ ID NO:12, examples of representative GGPP synthase proteins of the present invention are set forth in SEQ ID NO:27; SEQ ID NO:28; SEQ ID NO:29; SEQ ID NO:30; SEQ ID NO:31; SEQ ID NO:32; SEQ ID NO:33 and SEQ ID NO:34.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An isolated nucleic acid molecule encoding a geranylgeranyl diphosphate synthase protein of SEQ ID NO:2 or SEQ ID NO:12.

2. An isolated nucleic acid molecule of claim 1 encoding a geranylgeranyl diphosphate synthase protein from a Taxus species selected from the group consisting of *Tacus canadensis, Taxus brevifolia, Taxus cuspidata* and *Taxus baccata*.

3. An isolated nucleic acid molecule of claim 1 encoding a geranylgeranyl diphosphate synthase protein from a Taxus species selected from the group consisting of *Taxus canadensis* and *Taxus cuspidata*.

4. An isolated nucleic acid molecule of claim 1 having the nucleotide sequence set forth in SEQ ID NO:1 or SEQ ID NO:11.

5. An isolated nucleic acid molecule that is capable of hybridizing to the nucleic acid sequence set forth in SEQ ID NO:1, or to the complementary sequence of the nucleic acid sequence set forth in SEQ ID NO:1, under hybridization conditions of 3×SSC at 65° C. for 16 hours, said isolated nucleic acid molecule being capable of remaining hybridized to the nucleic acid sequence set forth in SEQ ID NO:1, or to the complementary sequence of the nucleic acid sequence set forth in SEQ ID NO:1, under wash conditions of 0.5×SSC, 55° C. for 30 minutes.

6. A replicable expression vector comprising a nucleic acid sequence of claim 5.

7. A replicable expression vector of claim 6 comprising a nucleic acid sequence encoding a geranylgeranyl diphosphate synthase from a Taxus species selected from the group consisting of *Taxus canadensis, Taxus brevifolia, Taxus cuspidata* and *Taxus baccata*.

8. A replicable expression vector of claim 7 comprising a nucleic acid sequence encoding a geranylgeranyl diphosphate synthase from a Taxus species selected from the group consisting of *Taxus canadensis*, and *Taxus cuspidata*.

9. A replicable vector comprising a nucleic acid sequence that is capable of hybridizing to the nucleic acid sequence set forth in SEQ ID NO:1, or to the complementary sequence of the nucleic acid sequence set forth in SEQ ID NO:1, under hybridization conditions of 3 ×SSC at 65° C. for 16 hours, said hybridizing nucleic acid sequence being capable of remaining hybridized to the nucleic acid sequence set forth in SEQ ID NO:1, or to the complementary sequence of the nucleic acid sequence set forth in SEQ ID NO:1, under wash conditions of 0.5×SSC, 55° C. for 30 minutes.

10. A host cell comprising a vector of claim 6.

11. A host cell of claim 10 wherein said host cell is a Taxus cell.

12. A method of increasing geranylgeranyl diphosphate synthase activity in a suitable host cell comprising introducing into said host cell an expression vector of claim 11 under conditions enabling expression of said protein encoded by said vector.

13. The method of claim 12 wherein said host cell is a Taxus cell.

* * * * *

UNITED STATES PATENT AND TRADEMARK OFFICE
CERTIFICATE OF CORRECTION

PATENT NO. : 6,043,072
DATED : March 28, 2000
INVENTOR(S) : R.A. Croteau et al.

It is certified that error appears in the above-identified patent and that said Letters Patent is hereby corrected as shown below:

| COLUMN | LINE | |
|---|---|---|
| 5 | 35 | "(EPP)" should read --(IPP)-- |
| 5 | 38 | "EPP" should read --IPP-- |
| 5 | 39 | "EPP" should read --IPP-- |
| 5 | 43-44 | "dimethy-lallyl" should break as follows: --dimethyl-allyl-- |
| 6 | 38 | "(α-amino" should read --α-amino-- |
| 6 | 63 | "EPP" should read --IPP-- |
| 9 | 4 | "0-subunit" should read --β-subunit-- |
| 9 | 36 | "NO: II)" should read --NO:11)-- |
| 9 | 47 | "NO: I)" should read --NO:1)-- |
| 16 | 57 | "0-glucuronidase" should read --β-glucuronidase-- |
| 17 | 21 | "5 1):" should read --51);-- |
| 18 | 46 | "*E. coil*" should read --*E. coli*-- |

UNITED STATES PATENT AND TRADEMARK OFFICE
CERTIFICATE OF CORRECTION

PATENT NO.  : 6,043,072
DATED       : March 28, 2000
INVENTOR(S) : R.A. Croteau et al.

It is certified that error appears in the above-identified patent and that said Letters Patent is hereby corrected as shown below:

| COLUMN | LINE | |
|---|---|---|
| 18 | 65 | "*E. coil*" should read --*E. coli*-- |
| 20 | 49-50 | the line "Isolation of a Full-Length Geranylgeranyl Diphosphate Synthase cDNA Clone" should be a centered header |
| 20 | 50 | the phrase beginning "Unless otherwise stated, . . ." should start a new paragraph |
| 21 | 17 | "train" should read --strain-- |
| 23 | 7 | "*annuzm*" should read --*annuum*-- |
| 27 | 26 | "$I_2$vapor." should read --$I_2$ vapor.-- |
| 27 | 35 | "Ky.)," should read --Ky.)),-- |
| 30 | 5 | "72:24814 254)." should read --72:248-254).-- |
| 30 | 20 | "3 1°" should read --31°-- |
| 30 | 43 | "Y. -Y." should read --Y.-Y.-- |
| 31 | 15 | "λPG1 5" should read --λPG15-- |

UNITED STATES PATENT AND TRADEMARK OFFICE
CERTIFICATE OF CORRECTION

PATENT NO.   :   6,043,072
DATED        :   March 28, 2000
INVENTOR(S)  :   R.A. Croteau et al.

It is certified that error appears in the above-identified patent and that said Letters Patent is hereby corrected as shown below:

| COLUMN | LINE | |
|---|---|---|
| 101 (Claim 2, | line 3) | "*Tacus*" should read --*Taxus*-- |
| 102 (Claim 9, | line 5) | "3 xSS" should read --3xSSC-- |

Signed and Sealed this

Fifteenth Day of May, 2001

Attest:

NICHOLAS P. GODICI

Attesting Officer

Acting Director of the United States Patent and Trademark Office

SEQUENCE LISTING

<160> NUMBER OF SEQ ID NOS: 34

<210> SEQ ID NO 1
<211> LENGTH: 1889
<212> TYPE: DNA
<213> ORGANISM: Taxus canadensis
<220> FEATURE:
<221> NAME/KEY: CDS
<222> LOCATION: (308)..(1486)

<400> SEQUENCE: 1

```
ggaagagcgg caatcattct gtcatttaaa ggttttctgc accgaaatcc tttaatttta     60
aggttttctg gaaggtgtgt gtgaaaattt gaagaaaatt aacaagactg taagtgtttt    120
tatatattta tgagctttgg tttacttggg tgttactgaa ttggaacata cgtgcatgtc    180
ggagcaaagc agcatatttg aaatttgtgg gtgttctttg aggtgtgttg cggatataga    240
tttgattgtt cagagttagt gtattttttt tttttgttgg ttagattaat tgggcaagtt    300
```

```
atagaga atg gct tac acg gca atg gca gca ggg acc caa agc ttg caa       349
        Met Ala Tyr Thr Ala Met Ala Ala Gly Thr Gln Ser Leu Gln
          1               5                  10 ctc cgc act gtt gct tcc tat caa gaa tgc aat agt atg agg agt tgt       397
Leu Arg Thr Val Ala Ser Tyr Gln Glu Cys Asn Ser Met Arg Ser Cys
 15                  20                  25                  30 ttt aaa ttg aca cct ttt aaa agt ttt cat gga gtg aat ttc aat gtt       445
Phe Lys Leu Thr Pro Phe Lys Ser Phe His Gly Val Asn Phe Asn Val
                 35                  40                  45 ccc tca ctg ggt gct gct aat tgt gag att atg ggt cac ctg aaa ctt       493
Pro Ser Leu Gly Ala Ala Asn Cys Glu Ile Met Gly His Leu Lys Leu
             50                  55                  60 ggg tca ttg cca tat aaa caa tgt tcg gtg tca tct aaa tcc aca aaa       541
Gly Ser Leu Pro Tyr Lys Gln Cys Ser Val Ser Ser Lys Ser Thr Lys
         65                  70                  75 aca atg gcc cag ttg gtt gat ttg gct gaa aca gag aag gcg gag gga       589
Thr Met Ala Gln Leu Val Asp Leu Ala Glu Thr Glu Lys Ala Glu Gly
     80                  85                  90 aag gat att gaa ttt gat ttc aac gag tat atg aag tcc aag gct gtg       637
Lys Asp Ile Glu Phe Asp Phe Asn Glu Tyr Met Lys Ser Lys Ala Val
 95                 100                 105                 110 gca gtg gat gcg gca ctg gat aag gca atc cca ctt gaa tat cct gaa       685
Ala Val Asp Ala Ala Leu Asp Lys Ala Ile Pro Leu Glu Tyr Pro Glu
                115                 120                 125 aaa ata cat gaa tca atg agg tat tca ctt cta gca gga ggt aag cgc       733
Lys Ile His Glu Ser Met Arg Tyr Ser Leu Leu Ala Gly Gly Lys Arg
            130                 135                 140 gtc agg cct gct ctg tgc att gca gca tgt gag ctt gta gga ggg agt       781
Val Arg Pro Ala Leu Cys Ile Ala Ala Cys Glu Leu Val Gly Gly Ser
        145                 150                 155 cag gac ctt gcc atg cca act gcc tgt gca atg gag atg att cat acc       829
Gln Asp Leu Ala Met Pro Thr Ala Cys Ala Met Glu Met Ile His Thr
    160                 165                 170 atg tct ctg att cat gat gac ttg ccg tgc atg gat aat gat gat ttc       877
Met Ser Leu Ile His Asp Asp Leu Pro Cys Met Asp Asn Asp Asp Phe
175                 180                 185                 190 aga aga ggg aag cca aca aat cac aag gtc ttt gga gag gac act gct       925
Arg Arg Gly Lys Pro Thr Asn His Lys Val Phe Gly Glu Asp Thr Ala
                195                 200                 205
```

| | | |
|---|---|---|
| gtt ctt gca ggg gac gcc ctg ctt tca ttt gca ttt gag cat att gct<br>Val Leu Ala Gly Asp Ala Leu Leu Ser Phe Ala Phe Glu His Ile Ala<br>210 215 220 | | 973 |
| gtg gct aca agc aag act gtg cct agt gat agg act tta agg gtg ata<br>Val Ala Thr Ser Lys Thr Val Pro Ser Asp Arg Thr Leu Arg Val Ile<br>225 230 235 | | 1021 |
| tct gaa ttg ggt aag aca ata ggc tct caa ggg ctt gta ggg ggg cag<br>Ser Glu Leu Gly Lys Thr Ile Gly Ser Gln Gly Leu Val Gly Gly Gln<br>240 245 250 | | 1069 |
| gtg gtt gat att aca tcc gag ggg gat gct aat gtg gac ctg aaa acc<br>Val Val Asp Ile Thr Ser Glu Gly Asp Ala Asn Val Asp Leu Lys Thr<br>255 260 265 270 | | 1117 |
| ctg gaa tgg att cat ata cac aag act gct gtg ctc ttg gaa tgt tca<br>Leu Glu Trp Ile His Ile His Lys Thr Ala Val Leu Leu Glu Cys Ser<br>275 280 285 | | 1165 |
| gtt gtg agt gga ggg atc ctt ggt ggt gct aca gag gac gag att gcg<br>Val Val Ser Gly Gly Ile Leu Gly Gly Ala Thr Glu Asp Glu Ile Ala<br>290 295 300 | | 1213 |
| aga att cgg cgg tac gcc cgg tgt gtg ggg ctt ctg ttt cag gtt gtg<br>Arg Ile Arg Arg Tyr Ala Arg Cys Val Gly Leu Leu Phe Gln Val Val<br>305 310 315 | | 1261 |
| gat gac ata ctt gat gtc act aaa tct tct gaa gaa ttg gga aag act<br>Asp Asp Ile Leu Asp Val Thr Lys Ser Ser Glu Glu Leu Gly Lys Thr<br>320 325 330 | | 1309 |
| gca gga aag gat ttg ctt act gat aag gct act tat ccc aag ttg atg<br>Ala Gly Lys Asp Leu Leu Thr Asp Lys Ala Thr Tyr Pro Lys Leu Met<br>335 340 345 350 | | 1357 |
| ggc ctg gag aaa gca aaa gaa ttt gcc gct gaa ttg gcg acg aga gcc<br>Gly Leu Glu Lys Ala Lys Glu Phe Ala Ala Glu Leu Ala Thr Arg Ala<br>355 360 365 | | 1405 |
| aag gaa gag ctg tca tcc ttt gat cag ata aag gct gca cct ttg ttg<br>Lys Glu Glu Leu Ser Ser Phe Asp Gln Ile Lys Ala Ala Pro Leu Leu<br>370 375 380 | | 1453 |
| ggt ctt gca gat tac att gca ttc agg caa aac tgagaacaaa gctgtaaagc<br>Gly Leu Ala Asp Tyr Ile Ala Phe Arg Gln Asn<br>385 390 | | 1506 |
| tattcttaca tatcatctgt tttttttga catctgctga aaattagcaa ataacttttt | | 1566 |
| caagtttgta tctcccctga atcataacga ttcaggacat gaggtttctg gtaccattga | | 1626 |
| aaagggggcg ctcattgtag ttgttttta gctaattcca acctgttttc tatgtttcca | | 1686 |
| ctttggatca atttgatgta gattatgttt gtaggggtga cattgttaga cttgttacat | | 1746 |
| gtcatcaaat tgttttttgc ggccttaaca tggttttaac ttttcactag caataaggtg | | 1806 |
| gcctaaagtg tttatgtaat ttttcaatat agatagatat cttttaacaa aaaaaaaaa | | 1866 |
| aaaaaaaaaa aaaaaaaaa aaa | | 1889 |

<210> SEQ ID NO 2
<211> LENGTH: 393
<212> TYPE: PRT
<213> ORGANISM: Taxus canadensis

<400> SEQUENCE: 2

Met Ala Tyr Thr Ala Met Ala Ala Gly Thr Gln Ser Leu Gln Leu Arg
 1               5                  10                  15

Thr Val Ala Ser Tyr Gln Glu Cys Asn Ser Met Arg Ser Cys Phe Lys
            20                  25                  30

Leu Thr Pro Phe Lys Ser Phe His Gly Val Asn Phe Asn Val Pro Ser
        35                  40                  45

```
Leu Gly Ala Ala Asn Cys Glu Ile Met Gly His Leu Lys Leu Gly Ser
 50                  55                  60

Leu Pro Tyr Lys Gln Cys Ser Val Ser Ser Lys Ser Thr Lys Thr Met
 65                  70                  75                  80

Ala Gln Leu Val Asp Leu Ala Glu Thr Glu Lys Ala Glu Gly Lys Asp
                 85                  90                  95

Ile Glu Phe Asp Phe Asn Glu Tyr Met Lys Ser Lys Ala Val Ala Val
            100                 105                 110

Asp Ala Ala Leu Asp Lys Ala Ile Pro Leu Glu Tyr Pro Glu Lys Ile
            115                 120                 125

His Glu Ser Met Arg Tyr Ser Leu Leu Ala Gly Gly Lys Arg Val Arg
130                 135                 140

Pro Ala Leu Cys Ile Ala Ala Cys Glu Leu Val Gly Gly Ser Gln Asp
145                 150                 155                 160

Leu Ala Met Pro Thr Ala Cys Ala Met Glu Met Ile His Thr Met Ser
                165                 170                 175

Leu Ile His Asp Asp Leu Pro Cys Met Asp Asn Asp Asp Phe Arg Arg
                180                 185                 190

Gly Lys Pro Thr Asn His Lys Val Phe Gly Glu Asp Thr Ala Val Leu
            195                 200                 205

Ala Gly Asp Ala Leu Leu Ser Phe Ala Phe Glu His Ile Ala Val Ala
210                 215                 220

Thr Ser Lys Thr Val Pro Ser Asp Arg Thr Leu Arg Val Ile Ser Glu
225                 230                 235                 240

Leu Gly Lys Thr Ile Gly Ser Gln Gly Leu Val Gly Gly Gln Val Val
                245                 250                 255

Asp Ile Thr Ser Glu Gly Asp Ala Asn Val Asp Leu Lys Thr Leu Glu
            260                 265                 270

Trp Ile His Ile His Lys Thr Ala Val Leu Leu Glu Cys Ser Val Val
            275                 280                 285

Ser Gly Gly Ile Leu Gly Gly Ala Thr Glu Asp Glu Ile Ala Arg Ile
290                 295                 300

Arg Arg Tyr Ala Arg Cys Val Gly Leu Leu Phe Gln Val Val Asp Asp
305                 310                 315                 320

Ile Leu Asp Val Thr Lys Ser Ser Glu Glu Leu Gly Lys Thr Ala Gly
                325                 330                 335

Lys Asp Leu Leu Thr Asp Lys Ala Thr Tyr Pro Lys Leu Met Gly Leu
            340                 345                 350

Glu Lys Ala Lys Glu Phe Ala Ala Glu Leu Ala Thr Arg Ala Lys Glu
            355                 360                 365

Glu Leu Ser Ser Phe Asp Gln Ile Lys Ala Ala Pro Leu Leu Gly Leu
370                 375                 380

Ala Asp Tyr Ile Ala Phe Arg Gln Asn
385                 390

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: reverse
      degenerate primer
<220> FEATURE:
<221> NAME/KEY: misc_difference
<222> LOCATION: (1)..(20)
```

<223> OTHER INFORMATION: degenerate reverse PCR primer wherein "n" at
     position 9 represents I and "n" at positions 15
     and 18 represent I,c or a

<400> SEQUENCE: 3
ttytayccnt tygcnggnmg                                          20

<210> SEQ ID NO 4
<211> LENGTH: 861
<212> TYPE: DNA
<213> ORGANISM: Taxus canadensis

<400> SEQUENCE: 4
ggttttctgc accgaaatcc tttaatttta aggttttctg gaaggtgtgt gtgaaaattt    60
gaagaaaatt aacaagactg taagtgtttt tatatattta tgagctttgg tttacttggg   120
tgttactgaa ttggaacata cgtgcatgtc ggagcaaagc agcatatttg aaatttgtgg   180
gtgttctttg aggtgtgttg cggatataga tttgattgtt cagagttagt gtattttttt   240
tttttgttgg ttagattaat tgggcaagtt atagagaatg cttacacgg caatggcagc    300 agggacccaa agcttgcaac tccgcactgt tgcttcctat caagaatgca atagtatgag   360
gagttgtttt aaattgacac cttttaaaag ttttcatgga gtgaatttca atgttccctc   420
actgggtgct gctaattgtg agattatggg tcacctgaaa cttgggtcat tgccatataa   480
acaatgttcg gtgtcatcta aatccacaaa aacaatggcc cagttggttg atttggctga   540
aacagagaag gcggagggaa aggatattga atttgatttc aacgagtata tgaagtccaa   600
ggctgtggca gtggatgcgg cactggataa ggcaatccca cttgaatatc ctgaaaaaat   660
acatgaatca atgaggtatt cacttctagc aggaggtaag cgcgtcaggc ctgctctgtg   720
cattgcagca tgtgagcttg taggagggag tcaggacctt gccatgccaa ctgcctgtgc   780
aatggagatg attcatacca tgtctctgat tcatgatgac ttgccgtgca tggataatga   840
tgatttcaga agagggaagc c                                            861

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: forward
     degenerate primer
<220> FEATURE:
<221> NAME/KEY: misc_difference
<222> LOCATION: (1)..(22)
<223> OTHER INFORMATION: degenerate PCR primer

<400> SEQUENCE: 5
tggcttacac ggcaatggca gc                                       22

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:
     non-degenerate reverse PCR primer
<220> FEATURE:
<221> NAME/KEY: misc_difference
<222> LOCATION: (1)..(23)
<223> OTHER INFORMATION: Non-degenerate PCR primer

<400> SEQUENCE: 6
ggcttacccc agccgaaatc atc                                      23

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: PCR primer
<220> FEATURE:
<221> NAME/KEY: misc_difference
<222> LOCATION: (1)..(38)
<223> OTHER INFORMATION: PCR primer containing KpnI site

<400> SEQUENCE: 7
ggggtacctc agttttgcct gaatgcaatg taatctgc                                 38

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence:PCR primer
<220> FEATURE:
<221> NAME/KEY: misc_difference
<222> LOCATION: (1)..(35)
<223> OTHER INFORMATION: PCR primer including BamHI site

<400> SEQUENCE: 8
gaagatctat ggcttacacg gcaatggcag caggg                                    35

<210> SEQ ID NO 9
<211> LENGTH: 43
<212> TYPE: DNA
<213> ORGANISM: Artificial Sequence
<220> FEATURE:
<223> OTHER INFORMATION: Description of Artificial Sequence:PCR primer
<220> FEATURE:
<221> NAME/KEY: misc_difference
<222> LOCATION: (1)..(43)
<223> OTHER INFORMATION: PCR primer for synthesizing Tr295 truncation
      product

<400> SEQUENCE: 9
gaagatctat gtttgatttc aacgagtata tgaagtccaa ggc                           43

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence:PCR primer
<220> FEATURE:
<221> NAME/KEY: misc_difference
<222> LOCATION: (1)..(38)
<223> OTHER INFORMATION: PCR primer for synthesizing Tr313 truncation

<400> SEQUENCE: 10
gaagatctat gaagtccaag gctgtggcag tggatgcg                                 38

<210> SEQ ID NO 11
<211> LENGTH: 885
<212> TYPE: DNA
<213> ORGANISM: Taxus cuspidata
<220> FEATURE:
<221> NAME/KEY: CDS
<222> LOCATION: (1)..(855)

<400> SEQUENCE: 11

-continued

| | | |
|---|---|---|
| ttt gat ttc aac gag tat atg aag tcc aag gct gtg gca gtg gat gcg<br>Phe Asp Phe Asn Glu Tyr Met Lys Ser Lys Ala Val Ala Val Asp Ala<br>1               5                  10                 15 | 48 |
| gca ctg gat aag gca atc cca ctt gaa tat cct gaa aaa ata cat gaa<br>Ala Leu Asp Lys Ala Ile Pro Leu Glu Tyr Pro Glu Lys Ile His Glu<br>        20                  25                  30 | 96 |
| tca atg agg tat tca ctt cta gca gga ggt aag cgc gtt agg cct gct<br>Ser Met Arg Tyr Ser Leu Leu Ala Gly Gly Lys Arg Val Arg Pro Ala<br>    35                  40                  45 | 144 |
| ctg tgc att gca gca tgt gag ctt gta gga ggg agt cag gac ctt gcc<br>Leu Cys Ile Ala Ala Cys Glu Leu Val Gly Gly Ser Gln Asp Leu Ala<br>50                  55                  60 | 192 |
| atg cca act gcc tgt gca atg gag atg att cat acc atg tct ctg att<br>Met Pro Thr Ala Cys Ala Met Glu Met Ile His Thr Met Ser Leu Ile<br>65                  70                  75                  80 | 240 |
| cat gat gac ttg ccc tgc atg gat aat gat gat ttc aga aga ggg aag<br>His Asp Asp Leu Pro Cys Met Asp Asn Asp Asp Phe Arg Arg Gly Lys<br>            85                  90                  95 | 288 |
| ccc aca aat cac aag gtc ttt gga gag gac act gct gtt ctt gca ggg<br>Pro Thr Asn His Lys Val Phe Gly Glu Asp Thr Ala Val Leu Ala Gly<br>        100                 105                 110 | 336 |
| gat gcc ctg ctt tca ttt gca ttt gag cat att gct gtg gct aca agc<br>Asp Ala Leu Leu Ser Phe Ala Phe Glu His Ile Ala Val Ala Thr Ser<br>    115                 120                 125 | 384 |
| aag act gtg cct agt gat agg act tta agg gtg ata tct gaa ttg ggt<br>Lys Thr Val Pro Ser Asp Arg Thr Leu Arg Val Ile Ser Glu Leu Gly<br>130                 135                 140 | 432 |
| aag aca ata ggc tct caa ggg ctt gta ggg gga cag gtg gtt gat att<br>Lys Thr Ile Gly Ser Gln Gly Leu Val Gly Gly Gln Val Val Asp Ile<br>145                 150                 155                 160 | 480 |
| aca tcc gag ggg gat gct aat gtg gac ctg aaa acc ctg gaa tgg att<br>Thr Ser Glu Gly Asp Ala Asn Val Asp Leu Lys Thr Leu Glu Trp Ile<br>            165                 170                 175 | 528 |
| cat ata cac aag act gct gtg ctc ttg gaa tgt tca gtt gtg agt gga<br>His Ile His Lys Thr Ala Val Leu Leu Glu Cys Ser Val Val Ser Gly<br>        180                 185                 190 | 576 |
| ggg atc ctt ggt ggt gct aca gag gat gag att gcg aga att cgg cgg<br>Gly Ile Leu Gly Gly Ala Thr Glu Asp Glu Ile Ala Arg Ile Arg Arg<br>    195                 200                 205 | 624 |
| tat gcc cgg tgt gtg ggg ctt ctg ttt cag gtt gtt gat gac ata ctt<br>Tyr Ala Arg Cys Val Gly Leu Leu Phe Gln Val Val Asp Asp Ile Leu<br>210                 215                 220 | 672 |
| gat gtc act aaa tct tct gaa gaa ttg gga aag act gca ggg aag gat<br>Asp Val Thr Lys Ser Ser Glu Glu Leu Gly Lys Thr Ala Gly Lys Asp<br>225                 230                 235                 240 | 720 |
| ttg cta act gat aag gct act tat ccc aag ttg atg ggc ctg gag aaa<br>Leu Leu Thr Asp Lys Ala Thr Tyr Pro Lys Leu Met Gly Leu Glu Lys<br>            245                 250                 255 | 768 |
| gca aaa gaa ttt gct gct gaa ttg gcg acg aga gcc aag gaa gag ctg<br>Ala Lys Glu Phe Ala Ala Glu Leu Ala Thr Arg Ala Lys Glu Glu Leu<br>        260                 265                 270 | 816 |
| tca tcc ttt gat cag ata aag gct gca cct tta ttg ggt cttgcagatt<br>Ser Ser Phe Asp Gln Ile Lys Ala Ala Pro Leu Leu Gly<br>    275                 280                 285 | 865 |
| acattgcatt caggcaaaac | 885 |

<210> SEQ ID NO 12
<211> LENGTH: 285
<212> TYPE: PRT
<213> ORGANISM: Taxus cuspidata

<400> SEQUENCE: 12

```
Phe Asp Phe Asn Glu Tyr Met Lys Ser Lys Ala Val Ala Val Asp Ala
 1               5                  10                  15
Ala Leu Asp Lys Ala Ile Pro Leu Glu Tyr Pro Lys Ile His Glu
             20                  25                  30
Ser Met Arg Tyr Ser Leu Leu Ala Gly Lys Arg Val Arg Pro Ala
         35                  40                  45
Leu Cys Ile Ala Ala Cys Glu Leu Val Gly Gly Ser Gln Asp Leu Ala
     50                  55                  60
Met Pro Thr Ala Cys Ala Met Glu Met Ile His Thr Met Ser Leu Ile
 65                  70                  75                  80
His Asp Asp Leu Pro Cys Met Asp Asn Asp Phe Arg Arg Gly Lys
                 85                  90                  95
Pro Thr Asn His Lys Val Phe Gly Glu Asp Thr Ala Val Leu Ala Gly
                100                 105                 110
Asp Ala Leu Leu Ser Phe Ala Phe Glu His Ile Ala Val Ala Thr Ser
            115                 120                 125
Lys Thr Val Pro Ser Asp Arg Thr Leu Arg Val Ile Ser Glu Leu Gly
        130                 135                 140
Lys Thr Ile Gly Ser Gln Gly Leu Val Gly Gly Gln Val Val Asp Ile
145                 150                 155                 160
Thr Ser Glu Gly Asp Ala Asn Val Asp Leu Lys Thr Leu Glu Trp Ile
                165                 170                 175
His Ile His Lys Thr Ala Val Leu Leu Glu Cys Ser Val Val Ser Gly
            180                 185                 190
Gly Ile Leu Gly Gly Ala Thr Glu Asp Glu Ile Ala Arg Ile Arg Arg
        195                 200                 205
Tyr Ala Arg Cys Val Gly Leu Leu Phe Gln Val Val Asp Asp Ile Leu
    210                 215                 220
Asp Val Thr Lys Ser Ser Glu Glu Leu Gly Lys Thr Ala Gly Lys Asp
225                 230                 235                 240
Leu Leu Thr Asp Lys Ala Thr Tyr Pro Lys Leu Met Gly Leu Glu Lys
                245                 250                 255
Ala Lys Glu Phe Ala Ala Glu Leu Ala Thr Arg Ala Lys Glu Glu Leu
            260                 265                 270
Ser Ser Phe Asp Gln Ile Lys Ala Ala Pro Leu Leu Gly
        275                 280                 285
```

<210> SEQ ID NO 13
<211> LENGTH: 1179
<212> TYPE: DNA
<213> ORGANISM: Artificial Sequence
<220> FEATURE:
<223> OTHER INFORMATION: Description of Artificial Sequence: nucleic acid encoding Taxus GGPP synthase protein
<220> FEATURE:
<221> NAME/KEY: CDS
<222> LOCATION: (1)..(1179)
<223> OTHER INFORMATION: computer-generated nucleic acid sequence encoding a Taxus GGPP synthase protein

<400> SEQUENCE: 13

```
atg ggt tac acg gca atg gca gca ggg acc caa agc ttg caa ctc cgc      48
Met Gly Tyr Thr Ala Met Ala Ala Gly Thr Gln Ser Leu Gln Leu Arg
 1               5                  10                  15
```

-continued

| | |
|---|---|
| act gtt gct tcc tat caa gaa tgc aat agt atg agg agt tgt ttt aaa<br>Thr Val Ala Ser Tyr Gln Glu Cys Asn Ser Met Arg Ser Cys Phe Lys<br>         20                     25                   30 | 96 |
| ttg aca cct ttt aaa agt ttt cat gga gtg aat ttc aat gtt ccc tca<br>Leu Thr Pro Phe Lys Ser Phe His Gly Val Asn Phe Asn Val Pro Ser<br>     35                    40                    45 | 144 |
| ctg ggt gct gct aat tgt gag att atg ggt cac ctg aaa ctt ggg tca<br>Leu Gly Ala Ala Asn Cys Glu Ile Met Gly His Leu Lys Leu Gly Ser<br>50                   55                    60 | 192 |
| ttg cca tat aaa caa tgt tcg gtg tca tct aaa tcc aca aaa aca atg<br>Leu Pro Tyr Lys Gln Cys Ser Val Ser Ser Lys Ser Thr Lys Thr Met<br>65                   70                  75             80 | 240 |
| gcc cag ttg gtt gat ttg gct gaa aca gag aag gcg gag gga aag gat<br>Ala Gln Leu Val Asp Leu Ala Glu Thr Glu Lys Ala Glu Gly Lys Asp<br>               85                  90                95 | 288 |
| att gaa ttt gat ttc aac gag tat atg aag tcc aag gct gtg gca gtg<br>Ile Glu Phe Asp Phe Asn Glu Tyr Met Lys Ser Lys Ala Val Ala Val<br>            100                  105             110 | 336 |
| gat gcg gca ctg gat aag gca atc cca ctt gaa tat cct gaa aaa ata<br>Asp Ala Ala Leu Asp Lys Ala Ile Pro Leu Glu Tyr Pro Glu Lys Ile<br>115                    120                    125 | 384 |
| cat gaa tca atg agg tat tca ctt cta gca gga ggt aag cgc gtc agg<br>His Glu Ser Met Arg Tyr Ser Leu Leu Ala Gly Gly Lys Arg Val Arg<br>130                    135                  140 | 432 |
| cct gct ctg tgc att gca gca tgt gag ctt gta gga ggg agt cag gac<br>Pro Ala Leu Cys Ile Ala Ala Cys Glu Leu Val Gly Gly Ser Gln Asp<br>145                    150                155             160 | 480 |
| ctt gcc atg cca act gcc tgt gca atg gag atg att cat acc atg tct<br>Leu Ala Met Pro Thr Ala Cys Ala Met Glu Met Ile His Thr Met Ser<br>               165                  170             175 | 528 |
| ctg att cat gat gac ttg ccg tgc atg gat aat gat gat ttc aga aga<br>Leu Ile His Asp Asp Leu Pro Cys Met Asp Asn Asp Asp Phe Arg Arg<br>            180                  185                190 | 576 |
| ggg aag cca aca aat cac aag gtc ttt gga gag gac act gct gtt ctt<br>Gly Lys Pro Thr Asn His Lys Val Phe Gly Glu Asp Thr Ala Val Leu<br>               195                  200             205 | 624 |
| gca ggg gac gcc ctg ctt tca ttt gca ttt gag cat att gct gtg gct<br>Ala Gly Asp Ala Leu Leu Ser Phe Ala Phe Glu His Ile Ala Val Ala<br>210                    215                  220 | 672 |
| aca agc aag act gtg cct agt gat agg act tta agg gtg ata tct gaa<br>Thr Ser Lys Thr Val Pro Ser Asp Arg Thr Leu Arg Val Ile Ser Glu<br>225                    230                235             240 | 720 |
| ttg ggt aag aca ata ggc tct caa ggg ctt gta ggg ggg cag gtg gtt<br>Leu Gly Lys Thr Ile Gly Ser Gln Gly Leu Val Gly Gly Gln Val Val<br>               245                  250             255 | 768 |
| gat att aca tcc gag ggg gat gct aat gtg gac ctg aaa acc ctg gaa<br>Asp Ile Thr Ser Glu Gly Asp Ala Asn Val Asp Leu Lys Thr Leu Glu<br>            260                  265                270 | 816 |
| tgg att cat ata cac aag act gct gtg ctc ttg gaa tgt tca gtt gtg<br>Trp Ile His Ile His Lys Thr Ala Val Leu Leu Glu Cys Ser Val Val<br>               275                  280             285 | 864 |
| agt gga ggg atc ctt ggt ggt gct aca gag gac gag att gcg aga att<br>Ser Gly Gly Ile Leu Gly Gly Ala Thr Glu Asp Glu Ile Ala Arg Ile<br>290                    295                  300 | 912 |
| cgg cgg tac gcc cgg tgt gtg ggg ctt ctg ttt cag gtt gtg gat gac<br>Arg Arg Tyr Ala Arg Cys Val Gly Leu Leu Phe Gln Val Val Asp Asp<br>305                    310                315             320 | 960 |
| ata ctt gat gtc act aaa tct tct gaa gaa ttg gga aag act gca gga<br>Ile Leu Asp Val Thr Lys Ser Ser Glu Glu Leu Gly Lys Thr Ala Gly<br>               325                  330             335 | 1008 |

```
aag gat ttg ctt act gat aag gct act tat ccc aag ttg atg ggc ctg    1056
Lys Asp Leu Leu Thr Asp Lys Ala Thr Tyr Pro Lys Leu Met Gly Leu
            340                 345                 350 gag aaa gca aaa gaa ttt gcc gct gaa ttg gcg acg aga gcc aag gaa    1104
Glu Lys Ala Lys Glu Phe Ala Ala Glu Leu Ala Thr Arg Ala Lys Glu
        355                 360                 365 gag ctg tca tcc ttt gat cag ata aag gct gca cct ttg ttg ggt ctt    1152
Glu Leu Ser Ser Phe Asp Gln Ile Lys Ala Ala Pro Leu Leu Gly Leu
    370                 375                 380 gca gat tac att gca ttc agg caa aac                                1179
Ala Asp Tyr Ile Ala Phe Arg Gln Asn
385                 390
```

<210> SEQ ID NO 14
<211> LENGTH: 393
<212> TYPE: PRT
<213> ORGANISM: Artificial Sequence
<220> FEATURE:
<223> OTHER INFORMATION: Description of Artificial Sequence: Taxus GGPP
      synthase protein variant
<220> FEATURE:
<221> NAME/KEY: VARIANT
<222> LOCATION: (1)..(393)
<223> OTHER INFORMATION: Computer-generated Taxus GGPP synthase protein
      variant

<400> SEQUENCE: 14

```
Met Gly Tyr Thr Ala Met Ala Ala Gly Thr Gln Ser Leu Gln Leu Arg
  1               5                  10                  15

Thr Val Ala Ser Tyr Gln Glu Cys Asn Ser Met Arg Ser Cys Phe Lys
             20                  25                  30

Leu Thr Pro Phe Lys Ser Phe His Gly Val Asn Phe Asn Val Pro Ser
         35                  40                  45

Leu Gly Ala Ala Asn Cys Glu Ile Met Gly His Leu Lys Leu Gly Ser
     50                  55                  60

Leu Pro Tyr Lys Gln Cys Ser Val Ser Ser Lys Ser Thr Lys Thr Met
 65                  70                  75                  80

Ala Gln Leu Val Asp Leu Ala Glu Thr Glu Lys Ala Glu Gly Lys Asp
                 85                  90                  95

Ile Glu Phe Asp Phe Asn Glu Tyr Met Lys Ser Lys Ala Val Ala Val
            100                 105                 110

Asp Ala Ala Leu Asp Lys Ala Ile Pro Leu Glu Tyr Pro Glu Lys Ile
        115                 120                 125

His Glu Ser Met Arg Tyr Ser Leu Leu Ala Gly Gly Lys Arg Val Arg
    130                 135                 140

Pro Ala Leu Cys Ile Ala Ala Cys Glu Leu Val Gly Gly Ser Gln Asp
145                 150                 155                 160

Leu Ala Met Pro Thr Ala Cys Ala Met Glu Met Ile His Thr Met Ser
                165                 170                 175

Leu Ile His Asp Asp Leu Pro Cys Met Asp Asn Asp Asp Phe Arg Arg
            180                 185                 190

Gly Lys Pro Thr Asn His Lys Val Phe Gly Glu Asp Thr Ala Val Leu
        195                 200                 205

Ala Gly Asp Ala Leu Leu Ser Phe Ala Phe Glu His Ile Ala Val Ala
    210                 215                 220

Thr Ser Lys Thr Val Pro Ser Asp Arg Thr Leu Arg Val Ile Ser Glu
225                 230                 235                 240
```

-continued

```
Leu Gly Lys Thr Ile Gly Ser Gln Gly Leu Val Gly Gln Val Val
                245                 250                 255

Asp Ile Thr Ser Glu Gly Asp Ala Asn Val Asp Leu Lys Thr Leu Glu
            260                 265                 270

Trp Ile His Ile His Lys Thr Ala Val Leu Leu Glu Cys Ser Val Val
                275                 280                 285

Ser Gly Gly Ile Leu Gly Gly Ala Thr Glu Asp Glu Ile Ala Arg Ile
            290                 295                 300

Arg Arg Tyr Ala Arg Cys Val Gly Leu Leu Phe Gln Val Val Asp Asp
305                 310                 315                 320

Ile Leu Asp Val Thr Lys Ser Ser Glu Glu Leu Gly Lys Thr Ala Gly
                325                 330                 335

Lys Asp Leu Leu Thr Asp Lys Ala Thr Tyr Pro Lys Leu Met Gly Leu
                340                 345                 350

Glu Lys Ala Lys Glu Phe Ala Ala Glu Leu Ala Thr Arg Ala Lys Glu
            355                 360                 365

Glu Leu Ser Ser Phe Asp Gln Ile Lys Ala Ala Pro Leu Leu Gly Leu
370                 375                 380

Ala Asp Tyr Ile Ala Phe Arg Gln Asn
385                 390
```

<210> SEQ ID NO 15
<211> LENGTH: 1179
<212> TYPE: DNA
<213> ORGANISM: Artificial Sequence
<220> FEATURE:
<223> OTHER INFORMATION: Description of Artificial Sequence: nucleic acid sequence encoding Taxus GGPP synthase
<220> FEATURE:
<221> NAME/KEY: CDS
<222> LOCATION: (1)..(1179)
<223> OTHER INFORMATION: Computer-generated nucleic acid sequence encoding Taxus GGPP synthase protein

<400> SEQUENCE: 15

```
atg gct tac acg gga atg gca gca ggg acc caa agc ttg caa ctc cgc        48
Met Ala Tyr Thr Gly Met Ala Ala Gly Thr Gln Ser Leu Gln Leu Arg
  1               5                  10                  15 act gtt gct tcc tat caa gaa tgc aat agt atg agg agt tgt ttt aaa        96
Thr Val Ala Ser Tyr Gln Glu Cys Asn Ser Met Arg Ser Cys Phe Lys
             20                  25                  30 ttg aca cct ttt aaa agt ttt cat gga gtg aat ttc aat gtt ccc tca       144
Leu Thr Pro Phe Lys Ser Phe His Gly Val Asn Phe Asn Val Pro Ser
         35                  40                  45 ctg ggt gct gct aat tgt gag att atg ggt cac ctg aaa ctt ggg tca       192
Leu Gly Ala Ala Asn Cys Glu Ile Met Gly His Leu Lys Leu Gly Ser
     50                  55                  60 ttg cca tat aaa caa tgt tcg gtg tca tct aaa tcc aca aaa aca atg       240
Leu Pro Tyr Lys Gln Cys Ser Val Ser Ser Lys Ser Thr Lys Thr Met
 65                  70                  75                  80 gcc cag ttg gtt gat ttg gct gaa aca gag aag gcg gag gga aag gat       288
Ala Gln Leu Val Asp Leu Ala Glu Thr Glu Lys Ala Glu Gly Lys Asp
                 85                  90                  95 att gaa ttt gat ttc aac gag tat atg aag tcc aag gct gtg gca gtg       336
Ile Glu Phe Asp Phe Asn Glu Tyr Met Lys Ser Lys Ala Val Ala Val
            100                 105                 110 gat gcg gca ctg gat aag gca atc cca ctt gaa tat cct gaa aaa ata       384
Asp Ala Ala Leu Asp Lys Ala Ile Pro Leu Glu Tyr Pro Glu Lys Ile
        115                 120                 125
```

-continued

| | | |
|---|---|---|
| cat gaa tca atg agg tat tca ctt cta gca gga ggt aag cgc gtc agg<br>His Glu Ser Met Arg Tyr Ser Leu Leu Ala Gly Gly Lys Arg Val Arg<br>130                         135                    140 | 432 |
| cct gct ctg tgc att gca gca tgt gag ctt gta gga ggg agt cag gac<br>Pro Ala Leu Cys Ile Ala Ala Cys Glu Leu Val Gly Gly Ser Gln Asp<br>145                 150                    155                    160 | 480 |
| ctt gcc atg cca act gcc tgt gca atg gag atg att cat acc atg tct<br>Leu Ala Met Pro Thr Ala Cys Ala Met Glu Met Ile His Thr Met Ser<br>                 165                    170                    175 | 528 |
| ctg att cat gat gac ttg ccg tgc atg gat aat gat gat ttc aga aga<br>Leu Ile His Asp Asp Leu Pro Cys Met Asp Asn Asp Asp Phe Arg Arg<br>180                         185                    190 | 576 |
| ggg aag cca aca aat cac aag gtc ttt gga gag gac act gct gtt ctt<br>Gly Lys Pro Thr Asn His Lys Val Phe Gly Glu Asp Thr Ala Val Leu<br>                 195                    200                    205 | 624 |
| gca ggg gac gcc ctg ctt tca ttt gca ttt gag cat att gct gtg gct<br>Ala Gly Asp Ala Leu Leu Ser Phe Ala Phe Glu His Ile Ala Val Ala<br>210                         215                    220 | 672 |
| aca agc aag act gtg cct agt gat agg act tta agg gtg ata tct gaa<br>Thr Ser Lys Thr Val Pro Ser Asp Arg Thr Leu Arg Val Ile Ser Glu<br>225                         230                    235                    240 | 720 |
| ttg ggt aag aca ata ggc tct caa ggg ctt gta ggg ggg cag gtg gtt<br>Leu Gly Lys Thr Ile Gly Ser Gln Gly Leu Val Gly Gly Gln Val Val<br>                 245                    250                    255 | 768 |
| gat att aca tcc gag ggg gat gct aat gtg gac ctg aaa acc ctg gaa<br>Asp Ile Thr Ser Glu Gly Asp Ala Asn Val Asp Leu Lys Thr Leu Glu<br>                 260                    265                    270 | 816 |
| tgg att cat ata cac aag act gct gtg ctc ttg gaa tgt tca gtt gtg<br>Trp Ile His Ile His Lys Thr Ala Val Leu Leu Glu Cys Ser Val Val<br>275                         280                    285 | 864 |
| agt gga ggg atc ctt ggt ggt gct aca gag gac gag att gcg aga att<br>Ser Gly Gly Ile Leu Gly Gly Ala Thr Glu Asp Glu Ile Ala Arg Ile<br>290                         295                    300 | 912 |
| cgg cgg tac gcc cgg tgt gtg ggg ctt ctg ttt cag gtt gtg gat gac<br>Arg Arg Tyr Ala Arg Cys Val Gly Leu Leu Phe Gln Val Val Asp Asp<br>305                         310                    315                    320 | 960 |
| ata ctt gat gtc act aaa tct tct gaa gaa ttg gga aag act gca gga<br>Ile Leu Asp Val Thr Lys Ser Ser Glu Glu Leu Gly Lys Thr Ala Gly<br>                 325                    330                    335 | 1008 |
| aag gat ttg ctt act gat aag gct act tat ccc aag ttg atg ggc ctg<br>Lys Asp Leu Leu Thr Asp Lys Ala Thr Tyr Pro Lys Leu Met Gly Leu<br>                 340                    345                    350 | 1056 |
| gag aaa gca aaa gaa ttt gcc gct gaa ttg gcg acg aga gcc aag gaa<br>Glu Lys Ala Lys Glu Phe Ala Ala Glu Leu Ala Thr Arg Ala Lys Glu<br>                 355                    360                    365 | 1104 |
| gag ctg tca tcc ttt gat cag ata aag gct gca cct ttg ttg ggt ctt<br>Glu Leu Ser Ser Phe Asp Gln Ile Lys Ala Ala Pro Leu Leu Gly Leu<br>370                         375                    380 | 1152 |
| gca gat tac att gca ttc agg caa aac<br>Ala Asp Tyr Ile Ala Phe Arg Gln Asn<br>385                         390 | 1179 |

<210> SEQ ID NO 16
<211> LENGTH: 393
<212> TYPE: PRT
<213> ORGANISM: Artificial Sequence
<220> FEATURE:
<223> OTHER INFORMATION: Description of Artificial Sequence: Taxus GGPP
      synthase protein variant
<220> FEATURE:
<221> NAME/KEY: VARIANT
<222> LOCATION: (1)..(393)

<223> OTHER INFORMATION: Computer-generated Taxus GGPP synthase protein variant

<400> SEQUENCE: 16

```
Met Ala Tyr Thr Gly Met Ala Gly Thr Gln Ser Leu Gln Leu Arg
  1               5                  10                  15

Thr Val Ala Ser Tyr Gln Glu Cys Asn Ser Met Arg Ser Cys Phe Lys
                 20                  25                  30

Leu Thr Pro Phe Lys Ser Phe His Gly Val Asn Phe Asn Val Pro Ser
             35                  40                  45

Leu Gly Ala Ala Asn Cys Glu Ile Met Gly His Leu Lys Leu Gly Ser
         50                  55                  60

Leu Pro Tyr Lys Gln Cys Ser Val Ser Ser Lys Ser Thr Lys Thr Met
 65                  70                  75                  80

Ala Gln Leu Val Asp Leu Ala Glu Thr Glu Lys Ala Glu Gly Lys Asp
                 85                  90                  95

Ile Glu Phe Asp Phe Asn Glu Tyr Met Lys Ser Lys Ala Val Ala Val
            100                 105                 110

Asp Ala Ala Leu Asp Lys Ala Ile Pro Leu Glu Tyr Pro Glu Lys Ile
        115                 120                 125

His Glu Ser Met Arg Tyr Ser Leu Leu Ala Gly Gly Lys Arg Val Arg
    130                 135                 140

Pro Ala Leu Cys Ile Ala Ala Cys Glu Leu Val Gly Gly Ser Gln Asp
145                 150                 155                 160

Leu Ala Met Pro Thr Ala Cys Ala Met Glu Met Ile His Thr Met Ser
                165                 170                 175

Leu Ile His Asp Asp Leu Pro Cys Met Asp Asn Asp Asp Phe Arg Arg
            180                 185                 190

Gly Lys Pro Thr Asn His Lys Val Phe Gly Glu Asp Thr Ala Val Leu
        195                 200                 205

Ala Gly Asp Ala Leu Leu Ser Phe Ala Phe Glu His Ile Ala Val Ala
    210                 215                 220

Thr Ser Lys Thr Val Pro Ser Asp Arg Thr Leu Arg Val Ile Ser Glu
225                 230                 235                 240

Leu Gly Lys Thr Ile Gly Ser Gln Gly Leu Val Gly Gly Gln Val Val
                245                 250                 255

Asp Ile Thr Ser Glu Gly Asp Ala Asn Val Asp Leu Lys Thr Leu Glu
            260                 265                 270

Trp Ile His Ile His Lys Thr Ala Val Leu Leu Glu Cys Ser Val Val
        275                 280                 285

Ser Gly Gly Ile Leu Gly Gly Ala Thr Glu Asp Glu Ile Ala Arg Ile
    290                 295                 300

Arg Arg Tyr Ala Arg Cys Val Gly Leu Leu Phe Gln Val Val Asp Asp
305                 310                 315                 320

Ile Leu Asp Val Thr Lys Ser Ser Glu Glu Leu Gly Lys Thr Ala Gly
                325                 330                 335

Lys Asp Leu Leu Thr Asp Lys Ala Thr Tyr Pro Lys Leu Met Gly Leu
            340                 345                 350

Glu Lys Ala Lys Glu Phe Ala Ala Glu Leu Ala Thr Arg Ala Lys Glu
        355                 360                 365

Glu Leu Ser Ser Phe Asp Gln Ile Lys Ala Ala Pro Leu Leu Gly Leu
    370                 375                 380

Ala Asp Tyr Ile Ala Phe Arg Gln Asn
385                 390
```

<210> SEQ ID NO 17
<211> LENGTH: 1179
<212> TYPE: DNA
<213> ORGANISM: Artificial Sequence
<220> FEATURE:
<223> OTHER INFORMATION: Description of Artificial Sequence: nucleic acid sequence encoding Taxus GGPP synthase
<220> FEATURE:
<221> NAME/KEY: CDS
<222> LOCATION: (1)..(1179)
<223> OTHER INFORMATION: Computer-generated nucleic acid sequence encoding Taxus GGPP synthase protein

<400> SEQUENCE: 17

```
atg gct tac acg gca atg gga gca ggg acc caa agc ttg caa ctc cgc      48
Met Ala Tyr Thr Ala Met Gly Ala Gly Thr Gln Ser Leu Gln Leu Arg
 1               5                  10                  15 act gtt gct tcc tat caa gaa tgc aat agt atg agg agt tgt ttt aaa      96
Thr Val Ala Ser Tyr Gln Glu Cys Asn Ser Met Arg Ser Cys Phe Lys
            20                  25                  30 ttg aca cct ttt aaa agt ttt cat gga gtg aat ttc aat gtt ccc tca     144
Leu Thr Pro Phe Lys Ser Phe His Gly Val Asn Phe Asn Val Pro Ser
        35                  40                  45 ctg ggt gct gct aat tgt gag att atg ggt cac ctg aaa ctt ggg tca     192
Leu Gly Ala Ala Asn Cys Glu Ile Met Gly His Leu Lys Leu Gly Ser
    50                  55                  60 ttg cca tat aaa caa tgt tcg gtg tca tct aaa tcc aca aaa aca atg     240
Leu Pro Tyr Lys Gln Cys Ser Val Ser Ser Lys Ser Thr Lys Thr Met
65                  70                  75                  80 gcc cag ttg gtt gat ttg gct gaa aca gag aag gcg gag gga aag gat     288
Ala Gln Leu Val Asp Leu Ala Glu Thr Glu Lys Ala Glu Gly Lys Asp
                85                  90                  95 att gaa ttt gat ttc aac gag tat atg aag tcc aag gct gtg gca gtg     336
Ile Glu Phe Asp Phe Asn Glu Tyr Met Lys Ser Lys Ala Val Ala Val
            100                 105                 110 gat gcg gca ctg gat aag gca atc cca ctt gaa tat cct gaa aaa ata     384
Asp Ala Ala Leu Asp Lys Ala Ile Pro Leu Glu Tyr Pro Glu Lys Ile
        115                 120                 125 cat gaa tca atg agg tat tca ctt cta gca gga ggt aag cgc gtc agg     432
His Glu Ser Met Arg Tyr Ser Leu Leu Ala Gly Gly Lys Arg Val Arg
    130                 135                 140 cct gct ctg tgc att gca gca tgt gag ctt gta gga ggg agt cag gac     480
Pro Ala Leu Cys Ile Ala Ala Cys Glu Leu Val Gly Gly Ser Gln Asp
145                 150                 155                 160 ctt gcc atg cca act gcc tgt gca atg gag atg att cat acc atg tct     528
Leu Ala Met Pro Thr Ala Cys Ala Met Glu Met Ile His Thr Met Ser
                165                 170                 175 ctg att cat gat gac ttg ccg tgc atg gat aat gat gat ttc aga aga     576
Leu Ile His Asp Asp Leu Pro Cys Met Asp Asn Asp Asp Phe Arg Arg
            180                 185                 190 ggg aag cca aca aat cac aag gtc ttt gga gag gac act gct gtt ctt     624
Gly Lys Pro Thr Asn His Lys Val Phe Gly Glu Asp Thr Ala Val Leu
        195                 200                 205 gca ggg gac gcc ctg ctt tca ttt gca ttt gag cat att gct gtg gct     672
Ala Gly Asp Ala Leu Leu Ser Phe Ala Phe Glu His Ile Ala Val Ala
    210                 215                 220 aca agc aag act gtg cct agt gat agg act tta agg gtg ata tct gaa     720
Thr Ser Lys Thr Val Pro Ser Asp Arg Thr Leu Arg Val Ile Ser Glu
225                 230                 235                 240
```

```
ttg ggt aag aca ata ggc tct caa ggg ctt gta ggg ggg cag gtg gtt         768
Leu Gly Lys Thr Ile Gly Ser Gln Gly Leu Val Gly Gly Gln Val Val
                245                 250                 255 gat att aca tcc gag ggg gat gct aat gtg gac ctg aaa acc ctg gaa         816
Asp Ile Thr Ser Glu Gly Asp Ala Asn Val Asp Leu Lys Thr Leu Glu
            260                 265                 270 tgg att cat ata cac aag act gct gtg ctc ttg gaa tgt tca gtt gtg         864
Trp Ile His Ile His Lys Thr Ala Val Leu Leu Glu Cys Ser Val Val
        275                 280                 285 agt gga ggg atc ctt ggt ggt gct aca gag gac gag att gcg aga att         912
Ser Gly Gly Ile Leu Gly Gly Ala Thr Glu Asp Glu Ile Ala Arg Ile
    290                 295                 300 cgg cgg tac gcc cgg tgt gtg ggg ctt ctg ttt cag gtt gtg gat gac         960
Arg Arg Tyr Ala Arg Cys Val Gly Leu Leu Phe Gln Val Val Asp Asp
305                 310                 315                 320 ata ctt gat gtc act aaa tct tct gaa gaa ttg gga aag act gca gga        1008
Ile Leu Asp Val Thr Lys Ser Ser Glu Glu Leu Gly Lys Thr Ala Gly
                325                 330                 335 aag gat ttg ctt act gat aag gct act tat ccc aag ttg atg ggc ctg        1056
Lys Asp Leu Leu Thr Asp Lys Ala Thr Tyr Pro Lys Leu Met Gly Leu
            340                 345                 350 gag aaa gca aaa gaa ttt gcc gct gaa ttg gcg acg aga gcc aag gaa        1104
Glu Lys Ala Lys Glu Phe Ala Ala Glu Leu Ala Thr Arg Ala Lys Glu
        355                 360                 365 gag ctg tca tcc ttt gat cag ata aag gct gca cct ttg ttg ggt ctt        1152
Glu Leu Ser Ser Phe Asp Gln Ile Lys Ala Ala Pro Leu Leu Gly Leu
    370                 375                 380 gca gat tac att gca ttc agg caa aac                                    1179
Ala Asp Tyr Ile Ala Phe Arg Gln Asn
385                 390
```

<210> SEQ ID NO 18
<211> LENGTH: 393
<212> TYPE: PRT
<213> ORGANISM: Artificial Sequence
<220> FEATURE:
<223> OTHER INFORMATION: Description of Artificial Sequence: Taxus GGPP
      synthase protein  variant
<220> FEATURE:
<221> NAME/KEY: VARIANT
<222> LOCATION: (1)..(393)
<223> OTHER INFORMATION: Computer-generated Taxus GGPP synthase protein
      variant

<400> SEQUENCE: 18

```
Met Ala Tyr Thr Ala Met Gly Ala Gly Thr Gln Ser Leu Gln Leu Arg
1               5                   10                  15

Thr Val Ala Ser Tyr Gln Glu Cys Asn Ser Met Arg Ser Cys Phe Lys
            20                  25                  30

Leu Thr Pro Phe Lys Ser Phe His Gly Val Asn Phe Asn Val Pro Ser
        35                  40                  45

Leu Gly Ala Ala Asn Cys Glu Ile Met Gly His Leu Lys Leu Gly Ser
    50                  55                  60

Leu Pro Tyr Lys Gln Cys Ser Val Ser Lys Ser Thr Lys Thr Met
65                  70                  75                  80

Ala Gln Leu Val Asp Leu Ala Glu Thr Glu Lys Ala Glu Gly Lys Asp
                85                  90                  95

Ile Glu Phe Asp Phe Asn Glu Tyr Met Lys Ser Lys Ala Val Ala Val
            100                 105                 110

Asp Ala Ala Leu Asp Lys Ala Ile Pro Leu Glu Tyr Pro Glu Lys Ile
        115                 120                 125
```

His Glu Ser Met Arg Tyr Ser Leu Leu Ala Gly Lys Arg Val Arg
    130                 135                 140

Pro Ala Leu Cys Ile Ala Ala Cys Glu Leu Val Gly Ser Gln Asp
145                 150                 155                 160

Leu Ala Met Pro Thr Ala Cys Ala Met Glu Met Ile His Thr Met Ser
                165                 170                 175

Leu Ile His Asp Asp Leu Pro Cys Met Asp Asn Asp Phe Arg Arg
            180                 185                 190

Gly Lys Pro Thr Asn His Lys Val Phe Gly Glu Asp Thr Ala Val Leu
        195                 200                 205

Ala Gly Asp Ala Leu Leu Ser Phe Ala Phe Glu His Ile Ala Val Ala
    210                 215                 220

Thr Ser Lys Thr Val Pro Ser Asp Arg Thr Leu Arg Val Ile Ser Glu
225                 230                 235                 240

Leu Gly Lys Thr Ile Gly Ser Gln Gly Leu Val Gly Gly Gln Val Val
                245                 250                 255

Asp Ile Thr Ser Glu Gly Asp Ala Asn Val Asp Leu Lys Thr Leu Glu
            260                 265                 270

Trp Ile His Ile His Lys Thr Ala Val Leu Leu Glu Cys Ser Val Val
        275                 280                 285

Ser Gly Gly Ile Leu Gly Gly Ala Thr Glu Asp Glu Ile Ala Arg Ile
    290                 295                 300

Arg Arg Tyr Ala Arg Cys Val Gly Leu Leu Phe Gln Val Val Asp Asp
305                 310                 315                 320

Ile Leu Asp Val Thr Lys Ser Ser Glu Glu Leu Gly Lys Thr Ala Gly
                325                 330                 335

Lys Asp Leu Leu Thr Asp Lys Ala Thr Tyr Pro Lys Leu Met Gly Leu
            340                 345                 350

Glu Lys Ala Lys Glu Phe Ala Ala Glu Leu Ala Thr Arg Ala Lys Glu
        355                 360                 365

Glu Leu Ser Ser Phe Asp Gln Ile Lys Ala Ala Pro Leu Leu Gly Leu
    370                 375                 380

Ala Asp Tyr Ile Ala Phe Arg Gln Asn
385                 390

<210> SEQ ID NO 19
<211> LENGTH: 1179
<212> TYPE: DNA
<213> ORGANISM: Artificial Sequence
<220> FEATURE:
<223> OTHER INFORMATION: Description of Artificial Sequence: nucleic
      acid sequence encoding Taxus GGPP synthase
<220> FEATURE:
<221> NAME/KEY: CDS
<222> LOCATION: (1)..(1179)
<223> OTHER INFORMATION: Computer-generated nucleic acid sequence
      encoding Taxus GGPP synthase protein

<400> SEQUENCE: 19 atg gct tac acg gca atg gca gga ggg acc caa agc ttg caa ctc cgc      48
Met Ala Tyr Thr Ala Met Ala Gly Gly Thr Gln Ser Leu Gln Leu Arg
  1               5                  10                  15 act gtt gct tcc tat caa gaa tgc aat agt atg agg agt tgt ttt aaa      96
Thr Val Ala Ser Tyr Gln Glu Cys Asn Ser Met Arg Ser Cys Phe Lys
             20                  25                  30 ttg aca cct ttt aaa agt ttt cat gga gtg aat ttc aat gtt ccc tca     144
Leu Thr Pro Phe Lys Ser Phe His Gly Val Asn Phe Asn Val Pro Ser
         35                  40                  45

```
ctg ggt gct gct aat tgt gag att atg ggt cac ctg aaa ctt ggg tca        192
Leu Gly Ala Ala Asn Cys Glu Ile Met Gly His Leu Lys Leu Gly Ser
 50              55                  60 ttg cca tat aaa caa tgt tcg gtg tca tct aaa tcc aca aaa aca atg        240
Leu Pro Tyr Lys Gln Cys Ser Val Ser Ser Lys Ser Thr Lys Thr Met
 65              70                  75                  80 gcc cag ttg gtt gat ttg gct gaa aca gag aag gcg gag gga aag gat        288
Ala Gln Leu Val Asp Leu Ala Glu Thr Glu Lys Ala Glu Gly Lys Asp
                 85                  90                  95 att gaa ttt gat ttc aac gag tat atg aag tcc aag gct gtg gca gtg        336
Ile Glu Phe Asp Phe Asn Glu Tyr Met Lys Ser Lys Ala Val Ala Val
                100                 105                 110 gat gcg gca ctg gat aag gca atc cca ctt gaa tat cct gaa aaa ata        384
Asp Ala Ala Leu Asp Lys Ala Ile Pro Leu Glu Tyr Pro Glu Lys Ile
            115                 120                 125 cat gaa tca atg agg tat tca ctt cta gca gga ggt aag cgc gtc agg        432
His Glu Ser Met Arg Tyr Ser Leu Leu Ala Gly Gly Lys Arg Val Arg
        130                 135                 140 cct gct ctg tgc att gca gca tgt gag ctt gta gga ggg agt cag gac        480
Pro Ala Leu Cys Ile Ala Ala Cys Glu Leu Val Gly Gly Ser Gln Asp
145             150                 155                 160 ctt gcc atg cca act gcc tgt gca atg gag atg att cat acc atg tct        528
Leu Ala Met Pro Thr Ala Cys Ala Met Glu Met Ile His Thr Met Ser
                165                 170                 175 ctg att cat gat gac ttg ccg tgc atg gat aat gat gat ttc aga aga        576
Leu Ile His Asp Asp Leu Pro Cys Met Asp Asn Asp Asp Phe Arg Arg
                180                 185                 190 ggg aag cca aca aat cac aag gtc ttt gga gag gac act gct gtt ctt        624
Gly Lys Pro Thr Asn His Lys Val Phe Gly Glu Asp Thr Ala Val Leu
            195                 200                 205 gca ggg gac gcc ctg ctt tca ttt gca ttt gag cat att gct gtg gct        672
Ala Gly Asp Ala Leu Leu Ser Phe Ala Phe Glu His Ile Ala Val Ala
        210                 215                 220 aca agc aag act gtg cct agt gat agg act tta agg gtg ata tct gaa        720
Thr Ser Lys Thr Val Pro Ser Asp Arg Thr Leu Arg Val Ile Ser Glu
225             230                 235                 240 ttg ggt aag aca ata ggc tct caa ggg ctt gta ggg ggg cag gtg gtt        768
Leu Gly Lys Thr Ile Gly Ser Gln Gly Leu Val Gly Gly Gln Val Val
                245                 250                 255 gat att aca tcc gag ggg gat gct aat gtg gac ctg aaa acc ctg gaa        816
Asp Ile Thr Ser Glu Gly Asp Ala Asn Val Asp Leu Lys Thr Leu Glu
                260                 265                 270 tgg att cat ata cac aag act gct gtg ctc ttg gaa tgt tca gtt gtg        864
Trp Ile His Ile His Lys Thr Ala Val Leu Leu Glu Cys Ser Val Val
            275                 280                 285 agt gga ggg atc ctt ggt ggt gct aca gag gac gag att gcg aga att        912
Ser Gly Gly Ile Leu Gly Gly Ala Thr Glu Asp Glu Ile Ala Arg Ile
        290                 295                 300 cgg cgg tac gcc cgg tgt gtg ggg ctt ctg ttt cag gtt gtg gat gac        960
Arg Arg Tyr Ala Arg Cys Val Gly Leu Leu Phe Gln Val Val Asp Asp
305             310                 315                 320 ata ctt gat gtc act aaa tct tct gaa gaa ttg gga aag act gca gga       1008
Ile Leu Asp Val Thr Lys Ser Ser Glu Glu Leu Gly Lys Thr Ala Gly
                325                 330                 335 aag gat ttg ctt act gat aag gct act tat ccc aag ttg atg ggc ctg       1056
Lys Asp Leu Leu Thr Asp Lys Ala Thr Tyr Pro Lys Leu Met Gly Leu
                340                 345                 350
```

-continued

```
gag aaa gca aaa gaa ttt gcc gct gaa ttg gcg acg aga gcc aag gaa      1104
Glu Lys Ala Lys Glu Phe Ala Ala Glu Leu Ala Thr Arg Ala Lys Glu
        355                 360                 365 gag ctg tca tcc ttt gat cag ata aag gct gca cct ttg ttg ggt ctt      1152
Glu Leu Ser Ser Phe Asp Gln Ile Lys Ala Ala Pro Leu Leu Gly Leu
    370                 375                 380 gca gat tac att gca ttc agg caa aac                                  1179
Ala Asp Tyr Ile Ala Phe Arg Gln Asn
385                 390
```

<210> SEQ ID NO 20
<211> LENGTH: 393
<212> TYPE: PRT
<213> ORGANISM: Artificial Sequence
<220> FEATURE:
<223> OTHER INFORMATION: Description of Artificial Sequence: Taxus GGPP
      synthase protein variant
<220> FEATURE:
<221> NAME/KEY: VARIANT
<222> LOCATION: (1)..(393)
<223> OTHER INFORMATION: Computer-generated Taxus GGPP synthase protein
      variant

<400> SEQUENCE: 20

```
Met Ala Tyr Thr Ala Met Ala Gly Gly Thr Gln Ser Leu Gln Leu Arg
  1               5                  10                  15

Thr Val Ala Ser Tyr Gln Glu Cys Asn Ser Met Arg Ser Cys Phe Lys
                 20                  25                  30

Leu Thr Pro Phe Lys Ser Phe His Gly Val Asn Phe Asn Val Pro Ser
             35                  40                  45

Leu Gly Ala Ala Asn Cys Glu Ile Met Gly His Leu Lys Leu Gly Ser
         50                  55                  60

Leu Pro Tyr Lys Gln Cys Ser Val Ser Ser Lys Ser Thr Lys Thr Met
 65                  70                  75                  80

Ala Gln Leu Val Asp Leu Ala Glu Thr Glu Lys Ala Glu Gly Lys Asp
                 85                  90                  95

Ile Glu Phe Asp Phe Asn Glu Tyr Met Lys Ser Lys Ala Val Ala Val
            100                 105                 110

Asp Ala Ala Leu Asp Lys Ala Ile Pro Leu Glu Tyr Pro Glu Lys Ile
        115                 120                 125

His Glu Ser Met Arg Tyr Ser Leu Leu Ala Gly Gly Lys Arg Val Arg
    130                 135                 140

Pro Ala Leu Cys Ile Ala Ala Cys Glu Leu Val Gly Gly Ser Gln Asp
145                 150                 155                 160

Leu Ala Met Pro Thr Ala Cys Ala Met Glu Met Ile His Thr Met Ser
                165                 170                 175

Leu Ile His Asp Asp Leu Pro Cys Met Asp Asn Asp Asp Phe Arg Arg
            180                 185                 190

Gly Lys Pro Thr Asn His Lys Val Phe Gly Glu Asp Thr Ala Val Leu
        195                 200                 205

Ala Gly Asp Ala Leu Leu Ser Phe Ala Phe Glu His Ile Ala Val Ala
    210                 215                 220

Thr Ser Lys Thr Val Pro Ser Asp Arg Thr Leu Arg Val Ile Ser Glu
225                 230                 235                 240

Leu Gly Lys Thr Ile Gly Ser Gln Gly Leu Val Gly Gly Gln Val Val
                245                 250                 255

Asp Ile Thr Ser Glu Gly Asp Ala Asn Val Asp Leu Lys Thr Leu Glu
            260                 265                 270
```

```
Trp Ile His Ile His Lys Thr Ala Val Leu Leu Glu Cys Ser Val Val
            275                 280                 285

Ser Gly Gly Ile Leu Gly Gly Ala Thr Glu Asp Glu Ile Ala Arg Ile
            290                 295                 300

Arg Arg Tyr Ala Arg Cys Val Gly Leu Leu Phe Gln Val Val Asp Asp
305                 310                 315                 320

Ile Leu Asp Val Thr Lys Ser Ser Glu Glu Leu Gly Lys Thr Ala Gly
                325                 330                 335

Lys Asp Leu Leu Thr Asp Lys Ala Thr Tyr Pro Lys Leu Met Gly Leu
            340                 345                 350

Glu Lys Ala Lys Glu Phe Ala Ala Glu Leu Ala Thr Arg Ala Lys Glu
            355                 360                 365

Glu Leu Ser Ser Phe Asp Gln Ile Lys Ala Ala Pro Leu Leu Gly Leu
            370                 375                 380

Ala Asp Tyr Ile Ala Phe Arg Gln Asn
385                 390

<210> SEQ ID NO 21
<211> LENGTH: 1179
<212> TYPE: DNA
<213> ORGANISM: Artificial Sequence
<220> FEATURE:
<223> OTHER INFORMATION: Description of Artificial Sequence: nucleic
      acid sequence encoding Taxus GGPP synthase
<220> FEATURE:
<221> NAME/KEY: CDS
<222> LOCATION: (1)..(1179)
<223> OTHER INFORMATION: Computer-generated nucleic acid sequence
      encoding Taxus GGPP synthase protein

<400> SEQUENCE: 21 atg gct tac acg gca atg gca gca gcg acc caa agc ttg caa ctc cgc      48
Met Ala Tyr Thr Ala Met Ala Ala Ala Thr Gln Ser Leu Gln Leu Arg
  1               5                  10                  15 act gtt gct tcc tat caa gaa tgc aat agt atg agg agt tgt ttt aaa      96
Thr Val Ala Ser Tyr Gln Glu Cys Asn Ser Met Arg Ser Cys Phe Lys
             20                  25                  30 ttg aca cct ttt aaa agt ttt cat gga gtg aat ttc aat gtt ccc tca     144
Leu Thr Pro Phe Lys Ser Phe His Gly Val Asn Phe Asn Val Pro Ser
         35                  40                  45 ctg ggt gct gct aat tgt gag att atg ggt cac ctg aaa ctt ggg tca     192
Leu Gly Ala Ala Asn Cys Glu Ile Met Gly His Leu Lys Leu Gly Ser
     50                  55                  60 ttg cca tat aaa caa tgt tcg gtg tca tct aaa tcc aca aaa aca atg     240
Leu Pro Tyr Lys Gln Cys Ser Val Ser Ser Lys Ser Thr Lys Thr Met
 65                  70                  75                  80 gcc cag ttg gtt gat ttg gct gaa aca gag aag gcg gag gga aag gat     288
Ala Gln Leu Val Asp Leu Ala Glu Thr Glu Lys Ala Glu Gly Lys Asp
                 85                  90                  95 att gaa ttt gat ttc aac gag tat atg aag tcc aag gct gtg gca gtg     336
Ile Glu Phe Asp Phe Asn Glu Tyr Met Lys Ser Lys Ala Val Ala Val
            100                 105                 110 gat gcg gca ctg gat aag gca atc cca ctt gaa tat cct gaa aaa ata     384
Asp Ala Ala Leu Asp Lys Ala Ile Pro Leu Glu Tyr Pro Glu Lys Ile
        115                 120                 125 cat gaa tca atg agg tat tca ctt cta gca gga ggt aag cgc gtc agg     432
His Glu Ser Met Arg Tyr Ser Leu Leu Ala Gly Gly Lys Arg Val Arg
    130                 135                 140 cct gct ctg tgc att gca gca tgt gag ctt gta gga ggg agt cag gac     480
Pro Ala Leu Cys Ile Ala Ala Cys Glu Leu Val Gly Gly Ser Gln Asp
145                 150                 155                 160
```

```
ctt gcc atg cca act gcc tgt gca atg gag atg att cat acc atg tct    528
Leu Ala Met Pro Thr Ala Cys Ala Met Glu Met Ile His Thr Met Ser
            165                 170                 175 ctg att cat gat gac ttg ccg tgc atg gat aat gat gat ttc aga aga    576
Leu Ile His Asp Asp Leu Pro Cys Met Asp Asn Asp Asp Phe Arg Arg
            180                 185                 190 ggg aag cca aca aat cac aag gtc ttt gga gag gac act gct gtt ctt    624
Gly Lys Pro Thr Asn His Lys Val Phe Gly Glu Asp Thr Ala Val Leu
            195                 200                 205 gca ggg gac gcc ctg ctt tca ttt gca ttt gag cat att gct gtg gct    672
Ala Gly Asp Ala Leu Leu Ser Phe Ala Phe Glu His Ile Ala Val Ala
        210                 215                 220 aca agc aag act gtg cct agt gat agg act tta agg gtg ata tct gaa    720
Thr Ser Lys Thr Val Pro Ser Asp Arg Thr Leu Arg Val Ile Ser Glu
225                 230                 235                 240 ttg ggt aag aca ata ggc tct caa ggg ctt gta ggg ggg cag gtg gtt    768
Leu Gly Lys Thr Ile Gly Ser Gln Gly Leu Val Gly Gly Gln Val Val
            245                 250                 255 gat att aca tcc gag ggg gat gct aat gtg gac ctg aaa acc ctg gaa    816
Asp Ile Thr Ser Glu Gly Asp Ala Asn Val Asp Leu Lys Thr Leu Glu
            260                 265                 270 tgg att cat ata cac aag act gct gtg ctc ttg gaa tgt tca gtt gtg    864
Trp Ile His Ile His Lys Thr Ala Val Leu Leu Glu Cys Ser Val Val
        275                 280                 285 agt gga ggg atc ctt ggt ggt gct aca gag gac gag att gcg aga att    912
Ser Gly Gly Ile Leu Gly Gly Ala Thr Glu Asp Glu Ile Ala Arg Ile
        290                 295                 300 cgg cgg tac gcc cgg tgt gtg ggg ctt ctg ttt cag gtt gtg gat gac    960
Arg Arg Tyr Ala Arg Cys Val Gly Leu Leu Phe Gln Val Val Asp Asp
305                 310                 315                 320 ata ctt gat gtc act aaa tct tct gaa gaa ttg gga aag act gca gga   1008
Ile Leu Asp Val Thr Lys Ser Ser Glu Glu Leu Gly Lys Thr Ala Gly
            325                 330                 335 aag gat ttg ctt act gat aag gct act tat ccc aag ttg atg ggc ctg   1056
Lys Asp Leu Leu Thr Asp Lys Ala Thr Tyr Pro Lys Leu Met Gly Leu
            340                 345                 350 gag aaa gca aaa gaa ttt gcc gct gaa ttg gcg acg aga gcc aag gaa   1104
Glu Lys Ala Lys Glu Phe Ala Ala Glu Leu Ala Thr Arg Ala Lys Glu
            355                 360                 365 gag ctg tca tcc ttt gat cag ata aag gct gca cct ttg ttg ggt ctt   1152
Glu Leu Ser Ser Phe Asp Gln Ile Lys Ala Ala Pro Leu Leu Gly Leu
        370                 375                 380 gca gat tac att gca ttc agg caa aac                                1179
Ala Asp Tyr Ile Ala Phe Arg Gln Asn
385                 390

<210> SEQ ID NO 22
<211> LENGTH: 393
<212> TYPE: PRT
<213> ORGANISM: Artificial Sequence
<220> FEATURE:
<223> OTHER INFORMATION: Description of Artificial Sequence: Taxus GGPP
      synthase protein  variant
<220> FEATURE:
<221> NAME/KEY: VARIANT
<222> LOCATION: (1)..(393)
<223> OTHER INFORMATION: Computer-generated Taxus GGPP synthase protein
      variant

<400> SEQUENCE: 22

Met Ala Tyr Thr Ala Met Ala Ala Ala Thr Gln Ser Leu Gln Leu Arg
1               5                   10                  15
```

```
Thr Val Ala Ser Tyr Gln Glu Cys Asn Ser Met Arg Ser Cys Phe Lys
             20                  25                  30

Leu Thr Pro Phe Lys Ser Phe His Gly Val Asn Phe Asn Val Pro Ser
         35                  40                  45

Leu Gly Ala Ala Asn Cys Glu Ile Met Gly His Leu Lys Leu Gly Ser
     50                  55                  60

Leu Pro Tyr Lys Gln Cys Ser Val Ser Ser Lys Ser Thr Lys Thr Met
 65                  70                  75                  80

Ala Gln Leu Val Asp Leu Ala Glu Thr Glu Lys Ala Glu Gly Lys Asp
                 85                  90                  95

Ile Glu Phe Asp Phe Asn Glu Tyr Met Lys Ser Lys Ala Val Ala Val
            100                 105                 110

Asp Ala Ala Leu Asp Lys Ala Ile Pro Leu Glu Tyr Pro Glu Lys Ile
        115                 120                 125

His Glu Ser Met Arg Tyr Ser Leu Leu Ala Gly Gly Lys Arg Val Arg
    130                 135                 140

Pro Ala Leu Cys Ile Ala Ala Cys Glu Leu Val Gly Gly Ser Gln Asp
145                 150                 155                 160

Leu Ala Met Pro Thr Ala Cys Ala Met Glu Met Ile His Thr Met Ser
                165                 170                 175

Leu Ile His Asp Asp Leu Pro Cys Met Asp Asn Asp Asp Phe Arg Arg
            180                 185                 190

Gly Lys Pro Thr Asn His Lys Val Phe Gly Glu Asp Thr Ala Val Leu
        195                 200                 205

Ala Gly Asp Ala Leu Leu Ser Phe Ala Phe Glu His Ile Ala Val Ala
    210                 215                 220

Thr Ser Lys Thr Val Pro Ser Asp Arg Thr Leu Arg Val Ile Ser Glu
225                 230                 235                 240

Leu Gly Lys Thr Ile Gly Ser Gln Gly Leu Val Gly Gln Val Val
                245                 250                 255

Asp Ile Thr Ser Glu Gly Asp Ala Asn Val Asp Leu Lys Thr Leu Glu
            260                 265                 270

Trp Ile His Ile His Lys Thr Ala Val Leu Leu Glu Cys Ser Val Val
        275                 280                 285

Ser Gly Gly Ile Leu Gly Gly Ala Thr Glu Asp Glu Ile Ala Arg Ile
    290                 295                 300

Arg Arg Tyr Ala Arg Cys Val Gly Leu Leu Phe Gln Val Val Asp Asp
305                 310                 315                 320

Ile Leu Asp Val Thr Lys Ser Ser Glu Glu Leu Gly Lys Thr Ala Gly
                325                 330                 335

Lys Asp Leu Leu Thr Asp Lys Ala Thr Tyr Pro Lys Leu Met Gly Leu
            340                 345                 350

Glu Lys Ala Lys Glu Phe Ala Ala Glu Leu Ala Thr Arg Ala Lys Glu
        355                 360                 365

Glu Leu Ser Ser Phe Asp Gln Ile Lys Ala Ala Pro Leu Leu Gly Leu
    370                 375                 380

Ala Asp Tyr Ile Ala Phe Arg Gln Asn
385                 390

<210> SEQ ID NO 23
<211> LENGTH: 1179
<212> TYPE: DNA
<213> ORGANISM: Artificial Sequence
<220> FEATURE:
```

```
<223> OTHER INFORMATION: Description of Artificial Sequence: nucleic
      acid sequence encoding Taxus GGPP synthase
<220> FEATURE:
<221> NAME/KEY: CDS
<222> LOCATION: (1)..(1179)
<223> OTHER INFORMATION: Computer-generated nucleic acid sequence
      encoding Taxus GGPP synthase protein

<400> SEQUENCE: 23 atg gct tac acg gca atg gca gca ggg acc caa agc ttg caa ctc cgc          48
Met Ala Tyr Thr Ala Met Ala Ala Gly Thr Gln Ser Leu Gln Leu Arg
 1               5                  10                  15 act gtt ggt tcc tat caa gaa tgc aat agt atg agg agt tgt ttt aaa          96
Thr Val Gly Ser Tyr Gln Glu Cys Asn Ser Met Arg Ser Cys Phe Lys
             20                  25                  30 ttg aca cct ttt aaa agt ttt cat gga gtg aat ttc aat gtt ccc tca         144
Leu Thr Pro Phe Lys Ser Phe His Gly Val Asn Phe Asn Val Pro Ser
         35                  40                  45 ctg ggt gct gct aat tgt gag att atg ggt cac ctg aaa ctt ggg tca         192
Leu Gly Ala Ala Asn Cys Glu Ile Met Gly His Leu Lys Leu Gly Ser
     50                  55                  60 ttg cca tat aaa caa tgt tcg gtg tca tct aaa tcc aca aaa aca atg         240
Leu Pro Tyr Lys Gln Cys Ser Val Ser Ser Lys Ser Thr Lys Thr Met
 65                  70                  75                  80 gcc cag ttg gtt gat ttg gct gaa aca gag aag gcg gag gga aag gat         288
Ala Gln Leu Val Asp Leu Ala Glu Thr Glu Lys Ala Glu Gly Lys Asp
                 85                  90                  95 att gaa ttt gat ttc aac gag tat atg aag tcc aag gct gtg gca gtg         336
Ile Glu Phe Asp Phe Asn Glu Tyr Met Lys Ser Lys Ala Val Ala Val
            100                 105                 110 gat gcg gca ctg gat aag gca atc cca ctt gaa tat cct gaa aaa ata         384
Asp Ala Ala Leu Asp Lys Ala Ile Pro Leu Glu Tyr Pro Glu Lys Ile
        115                 120                 125 cat gaa tca atg agg tat tca ctt cta gca gga ggt aag cgc gtc agg         432
His Glu Ser Met Arg Tyr Ser Leu Leu Ala Gly Gly Lys Arg Val Arg
    130                 135                 140 cct gct ctg tgc att gca gca tgt gag ctt gta gga ggg agt cag gac         480
Pro Ala Leu Cys Ile Ala Ala Cys Glu Leu Val Gly Gly Ser Gln Asp
145                 150                 155                 160 ctt gcc atg cca act gcc tgt gca atg gag atg att cat acc atg tct         528
Leu Ala Met Pro Thr Ala Cys Ala Met Glu Met Ile His Thr Met Ser
                165                 170                 175 ctg att cat gat gac ttg ccg tgc atg gat aat gat gat ttc aga aga         576
Leu Ile His Asp Asp Leu Pro Cys Met Asp Asn Asp Asp Phe Arg Arg
            180                 185                 190 ggg aag cca aca aat cac aag gtc ttt gga gag gac act gct gtt ctt         624
Gly Lys Pro Thr Asn His Lys Val Phe Gly Glu Asp Thr Ala Val Leu
        195                 200                 205 gca ggg gac gcc ctg ctt tca ttt gca ttt gag cat att gct gtg gct         672
Ala Gly Asp Ala Leu Leu Ser Phe Ala Phe Glu His Ile Ala Val Ala
    210                 215                 220 aca agc aag act gtg cct agt gat agg act tta agg gtg ata tct gaa         720
Thr Ser Lys Thr Val Pro Ser Asp Arg Thr Leu Arg Val Ile Ser Glu
225                 230                 235                 240 ttg ggt aag aca ata ggc tct caa ggg ctt gta ggg ggg cag gtg gtt         768
Leu Gly Lys Thr Ile Gly Ser Gln Gly Leu Val Gly Gly Gln Val Val
                245                 250                 255 gat att aca tcc gag ggg gat gct aat gtg gac ctg aaa acc ctg gaa         816
Asp Ile Thr Ser Glu Gly Asp Ala Asn Val Asp Leu Lys Thr Leu Glu
            260                 265                 270
```

```
tgg att cat ata cac aag act gct gtg ctc ttg gaa tgt tca gtt gtg         864
Trp Ile His Ile His Lys Thr Ala Val Leu Leu Glu Cys Ser Val Val
            275                 280                 285 agt gga ggg atc ctt ggt ggt gct aca gag gac gag att gcg aga att         912
Ser Gly Gly Ile Leu Gly Gly Ala Thr Glu Asp Glu Ile Ala Arg Ile
290                 295                 300 cgg cgg tac gcc cgg tgt gtg ggg ctt ctg ttt cag gtt gtg gat gac         960
Arg Arg Tyr Ala Arg Cys Val Gly Leu Leu Phe Gln Val Val Asp Asp
305                 310                 315                 320 ata ctt gat gtc act aaa tct tct gaa gaa ttg gga aag act gca gga        1008
Ile Leu Asp Val Thr Lys Ser Ser Glu Glu Leu Gly Lys Thr Ala Gly
                325                 330                 335 aag gat ttg ctt act gat aag gct act tat ccc aag ttg atg ggc ctg        1056
Lys Asp Leu Leu Thr Asp Lys Ala Thr Tyr Pro Lys Leu Met Gly Leu
            340                 345                 350 gag aaa gca aaa gaa ttt gcc gct gaa ttg gcg acg aga gcc aag gaa        1104
Glu Lys Ala Lys Glu Phe Ala Ala Glu Leu Ala Thr Arg Ala Lys Glu
        355                 360                 365 gag ctg tca tcc ttt gat cag ata aag gct gca cct ttg ttg ggt ctt        1152
Glu Leu Ser Ser Phe Asp Gln Ile Lys Ala Ala Pro Leu Leu Gly Leu
370                 375                 380 gca gat tac att gca ttc agg caa aac                                    1179
Ala Asp Tyr Ile Ala Phe Arg Gln Asn
385                 390
```

<210> SEQ ID NO 24
<211> LENGTH: 393
<212> TYPE: PRT
<213> ORGANISM: Artificial Sequence
<220> FEATURE:
<223> OTHER INFORMATION: Description of Artificial Sequence: Taxus GGPP
      synthase protein variant
<220> FEATURE:
<221> NAME/KEY: VARIANT
<222> LOCATION: (1)..(393)
<223> OTHER INFORMATION: Computer-generated Taxus GGPP synthase protein
      variant

<400> SEQUENCE: 24

```
Met Ala Tyr Thr Ala Met Ala Ala Gly Thr Gln Ser Leu Gln Leu Arg
 1               5                  10                  15

Thr Val Gly Ser Tyr Gln Glu Cys Asn Ser Met Arg Ser Cys Phe Lys
            20                  25                  30

Leu Thr Pro Phe Lys Ser Phe His Gly Val Asn Phe Asn Val Pro Ser
        35                  40                  45

Leu Gly Ala Ala Asn Cys Glu Ile Met Gly His Leu Lys Leu Gly Ser
    50                  55                  60

Leu Pro Tyr Lys Gln Cys Ser Val Ser Ser Lys Ser Thr Lys Thr Met
65                  70                  75                  80

Ala Gln Leu Val Asp Leu Ala Glu Thr Glu Lys Ala Glu Gly Lys Asp
                85                  90                  95

Ile Glu Phe Asp Phe Asn Glu Tyr Met Lys Ser Lys Ala Val Ala Val
            100                 105                 110

Asp Ala Ala Leu Asp Lys Ala Ile Pro Leu Glu Tyr Pro Glu Lys Ile
        115                 120                 125

His Glu Ser Met Arg Tyr Ser Leu Leu Ala Gly Gly Lys Arg Val Arg
    130                 135                 140

Pro Ala Leu Cys Ile Ala Ala Cys Glu Leu Val Gly Gly Ser Gln Asp
145                 150                 155                 160
```

```
Leu Ala Met Pro Thr Ala Cys Ala Met Glu Met Ile His Thr Met Ser
            165                 170                 175

Leu Ile His Asp Asp Leu Pro Cys Met Asp Asn Asp Asp Phe Arg Arg
            180                 185                 190

Gly Lys Pro Thr Asn His Lys Val Phe Gly Glu Asp Thr Ala Val Leu
            195                 200                 205

Ala Gly Asp Ala Leu Leu Ser Phe Ala Phe Glu His Ile Ala Val Ala
        210                 215                 220

Thr Ser Lys Thr Val Pro Ser Asp Arg Thr Leu Arg Val Ile Ser Glu
225                 230                 235                 240

Leu Gly Lys Thr Ile Gly Ser Gln Gly Leu Val Gly Gly Gln Val Val
            245                 250                 255

Asp Ile Thr Ser Glu Gly Asp Ala Asn Val Asp Leu Lys Thr Leu Glu
            260                 265                 270

Trp Ile His Ile His Lys Thr Ala Val Leu Leu Glu Cys Ser Val Val
            275                 280                 285

Ser Gly Gly Ile Leu Gly Gly Ala Thr Glu Asp Glu Ile Ala Arg Ile
        290                 295                 300

Arg Arg Tyr Ala Arg Cys Val Gly Leu Leu Phe Gln Val Val Asp Asp
305                 310                 315                 320

Ile Leu Asp Val Thr Lys Ser Ser Glu Glu Leu Gly Lys Thr Ala Gly
            325                 330                 335

Lys Asp Leu Leu Thr Asp Lys Ala Thr Tyr Pro Lys Leu Met Gly Leu
            340                 345                 350

Glu Lys Ala Lys Glu Phe Ala Ala Glu Leu Ala Thr Arg Ala Lys Glu
            355                 360                 365

Glu Leu Ser Ser Phe Asp Gln Ile Lys Ala Ala Pro Leu Leu Gly Leu
        370                 375                 380

Ala Asp Tyr Ile Ala Phe Arg Gln Asn
385                 390
```

<210> SEQ ID NO 25
<211> LENGTH: 1179
<212> TYPE: DNA
<213> ORGANISM: Artificial Sequence
<220> FEATURE:
<223> OTHER INFORMATION: Description of Artificial Sequence: nucleic
    acid sequence encoding Taxus GGPP synthase
<220> FEATURE:
<221> NAME/KEY: CDS
<222> LOCATION: (1)..(1179)
<223> OTHER INFORMATION: Computer-generated nucleic acid sequence
    encoding Taxus GGPP synthase protein

<400> SEQUENCE: 25

```
atg gct tac acg gca atg gca gca ggg acc caa agc ttg caa ctc cgc    48
Met Ala Tyr Thr Ala Met Ala Ala Gly Thr Gln Ser Leu Gln Leu Arg
 1               5                  10                  15 act gtt gct tcc tat caa gac tgc aat agt atg agg agt tgt ttt aaa    96
Thr Val Ala Ser Tyr Gln Asp Cys Asn Ser Met Arg Ser Cys Phe Lys
                20                  25                  30 ttg aca cct ttt aaa agt ttt cat gga gtg aat ttc aat gtt ccc tca   144
Leu Thr Pro Phe Lys Ser Phe His Gly Val Asn Phe Asn Val Pro Ser
            35                  40                  45 ctg ggt gct gct aat tgt gag att atg ggt cac ctg aaa ctt ggg tca   192
Leu Gly Ala Ala Asn Cys Glu Ile Met Gly His Leu Lys Leu Gly Ser
        50                  55                  60
```

```
ttg cca tat aaa caa tgt tcg gtg tca tct aaa tcc aca aaa aca atg      240
Leu Pro Tyr Lys Gln Cys Ser Val Ser Ser Lys Ser Thr Lys Thr Met
 65                  70                  75                  80 gcc cag ttg gtt gat ttg gct gaa aca gag aag gcg gag gga aag gat      288
Ala Gln Leu Val Asp Leu Ala Glu Thr Glu Lys Ala Glu Gly Lys Asp
                 85                  90                  95 att gaa ttt gat ttc aac gag tat atg aag tcc aag gct gtg gca gtg      336
Ile Glu Phe Asp Phe Asn Glu Tyr Met Lys Ser Lys Ala Val Ala Val
            100                 105                 110 gat gcg gca ctg gat aag gca atc cca ctt gaa tat cct gaa aaa ata      384
Asp Ala Ala Leu Asp Lys Ala Ile Pro Leu Glu Tyr Pro Glu Lys Ile
        115                 120                 125 cat gaa tca atg agg tat tca ctt cta gca gga ggt aag cgc gtc agg      432
His Glu Ser Met Arg Tyr Ser Leu Leu Ala Gly Gly Lys Arg Val Arg
130                 135                 140 cct gct ctg tgc att gca gca tgt gag ctt gta gga ggg agt cag gac      480
Pro Ala Leu Cys Ile Ala Ala Cys Glu Leu Val Gly Gly Ser Gln Asp
145                 150                 155                 160 ctt gcc atg cca act gcc tgt gca atg gag atg att cat acc atg tct      528
Leu Ala Met Pro Thr Ala Cys Ala Met Glu Met Ile His Thr Met Ser
                165                 170                 175 ctg att cat gat gac ttg ccg tgc atg gat aat gat gat ttc aga aga      576
Leu Ile His Asp Asp Leu Pro Cys Met Asp Asn Asp Asp Phe Arg Arg
            180                 185                 190 ggg aag cca aca aat cac aag gtc ttt gga gag gac act gct gtt ctt      624
Gly Lys Pro Thr Asn His Lys Val Phe Gly Glu Asp Thr Ala Val Leu
        195                 200                 205 gca ggg gac gcc ctg ctt tca ttt gca ttt gag cat att gct gtg gct      672
Ala Gly Asp Ala Leu Leu Ser Phe Ala Phe Glu His Ile Ala Val Ala
210                 215                 220 aca agc aag act gtg cct agt gat agg act tta agg gtg ata tct gaa      720
Thr Ser Lys Thr Val Pro Ser Asp Arg Thr Leu Arg Val Ile Ser Glu
225                 230                 235                 240 ttg ggt aag aca ata ggc tct caa ggg ctt gta ggg ggg cag gtg gtt      768
Leu Gly Lys Thr Ile Gly Ser Gln Gly Leu Val Gly Gly Gln Val Val
                245                 250                 255 gat att aca tcc gag ggg gat gct aat gtg gac ctg aaa acc ctg gaa      816
Asp Ile Thr Ser Glu Gly Asp Ala Asn Val Asp Leu Lys Thr Leu Glu
            260                 265                 270 tgg att cat ata cac aag act gct gtg ctc ttg gaa tgt tca gtt gtg      864
Trp Ile His Ile His Lys Thr Ala Val Leu Leu Glu Cys Ser Val Val
        275                 280                 285 agt gga ggg atc ctt ggt ggt gct aca gag gac gag att gcg aga att      912
Ser Gly Gly Ile Leu Gly Gly Ala Thr Glu Asp Glu Ile Ala Arg Ile
290                 295                 300 cgg cgg tac gcc cgg tgt gtg ggg ctt ctg ttt cag gtt gtg gat gac      960
Arg Arg Tyr Ala Arg Cys Val Gly Leu Leu Phe Gln Val Val Asp Asp
305                 310                 315                 320 ata ctt gat gtc act aaa tct tct gaa gaa ttg gga aag act gca gga     1008
Ile Leu Asp Val Thr Lys Ser Ser Glu Glu Leu Gly Lys Thr Ala Gly
                325                 330                 335 aag gat ttg ctt act gat aag gct act tat ccc aag ttg atg ggc ctg     1056
Lys Asp Leu Leu Thr Asp Lys Ala Thr Tyr Pro Lys Leu Met Gly Leu
            340                 345                 350 gag aaa gca aaa gaa ttt gcc gct gaa ttg gcg acg aga gcc aag gaa     1104
Glu Lys Ala Lys Glu Phe Ala Ala Glu Leu Ala Thr Arg Ala Lys Glu
        355                 360                 365 gag ctg tca tcc ttt gat cag ata aag gct gca cct ttg ttg ggt ctt     1152
Glu Leu Ser Ser Phe Asp Gln Ile Lys Ala Ala Pro Leu Leu Gly Leu
370                 375                 380
```

```
      gca gat tac att gca ttc agg caa aac                                        1179
      Ala Asp Tyr Ile Ala Phe Arg Gln Asn
      385                 390
```

<210> SEQ ID NO 26
<211> LENGTH: 393
<212> TYPE: PRT
<213> ORGANISM: Artificial Sequence
<220> FEATURE:
<223> OTHER INFORMATION: Description of Artificial Sequence: Taxus GGPP
      synthase protein  variant
<220> FEATURE:
<221> NAME/KEY: VARIANT
<222> LOCATION: (1)..(393)
<223> OTHER INFORMATION: Computer-generated Taxus GGPP synthase protein
      variant

<400> SEQUENCE: 26

```
Met Ala Tyr Thr Ala Met Ala Ala Gly Thr Gln Ser Leu Gln Leu Arg
 1               5                  10                  15

Thr Val Ala Ser Tyr Gln Asp Cys Asn Ser Met Arg Ser Cys Phe Lys
                20                  25                  30

Leu Thr Pro Phe Lys Ser Phe His Gly Val Asn Phe Asn Val Pro Ser
            35                  40                  45

Leu Gly Ala Ala Asn Cys Glu Ile Met Gly His Leu Lys Leu Gly Ser
    50                  55                  60

Leu Pro Tyr Lys Gln Cys Ser Val Ser Ser Lys Ser Thr Lys Thr Met
65                  70                  75                  80

Ala Gln Leu Val Asp Leu Ala Glu Thr Glu Lys Ala Glu Gly Lys Asp
                85                  90                  95

Ile Glu Phe Asp Phe Asn Glu Tyr Met Lys Ser Lys Ala Val Ala Val
            100                 105                 110

Asp Ala Ala Leu Asp Lys Ala Ile Pro Leu Glu Tyr Pro Glu Lys Ile
        115                 120                 125

His Glu Ser Met Arg Tyr Ser Leu Leu Ala Gly Gly Lys Arg Val Arg
    130                 135                 140

Pro Ala Leu Cys Ile Ala Ala Cys Glu Leu Val Gly Gly Ser Gln Asp
145                 150                 155                 160

Leu Ala Met Pro Thr Ala Cys Ala Met Glu Met Ile His Thr Met Ser
                165                 170                 175

Leu Ile His Asp Asp Leu Pro Cys Met Asp Asn Asp Asp Phe Arg Arg
            180                 185                 190

Gly Lys Pro Thr Asn His Lys Val Phe Gly Glu Asp Thr Ala Val Leu
        195                 200                 205

Ala Gly Asp Ala Leu Leu Ser Phe Ala Phe Glu His Ile Ala Val Ala
    210                 215                 220

Thr Ser Lys Thr Val Pro Ser Asp Arg Thr Leu Arg Val Ile Ser Glu
225                 230                 235                 240

Leu Gly Lys Thr Ile Gly Ser Gln Gly Leu Val Gly Gln Val Val
                245                 250                 255

Asp Ile Thr Ser Glu Gly Asp Ala Asn Val Asp Leu Lys Thr Leu Glu
            260                 265                 270

Trp Ile His Ile His Lys Thr Ala Val Leu Leu Glu Cys Ser Val Val
        275                 280                 285

Ser Gly Gly Ile Leu Gly Gly Ala Thr Glu Asp Glu Ile Ala Arg Ile
    290                 295                 300
```

```
Arg Arg Tyr Ala Arg Cys Val Gly Leu Leu Phe Gln Val Val Asp Asp
305                 310                 315                 320

Ile Leu Asp Val Thr Lys Ser Ser Glu Glu Leu Gly Lys Thr Ala Gly
                325                 330                 335

Lys Asp Leu Leu Thr Asp Lys Ala Thr Tyr Pro Lys Leu Met Gly Leu
                340                 345                 350

Glu Lys Ala Lys Glu Phe Ala Ala Glu Leu Ala Thr Arg Ala Lys Glu
                355                 360                 365

Glu Leu Ser Ser Phe Asp Gln Ile Lys Ala Ala Pro Leu Leu Gly Leu
370                 375                 380

Ala Asp Tyr Ile Ala Phe Arg Gln Asn
385                 390

<210> SEQ ID NO 27
<211> LENGTH: 393
<212> TYPE: PRT
<213> ORGANISM: Artificial Sequence
<220> FEATURE:
<223> OTHER INFORMATION: Description of Artificial Sequence: Taxus GGPP
      synthase protein  variant
<220> FEATURE:
<221> NAME/KEY: VARIANT
<222> LOCATION: (1)..(393)
<223> OTHER INFORMATION: Computer-generated Taxus GGPP synthase protein
      variant

<400> SEQUENCE: 27

Met Ala Tyr Thr Ala Met Ala Ala Gly Thr Gln Ser Leu Gln Leu Arg
  1               5                  10                  15

Thr Val Ala Ser Tyr Gln Glu Cys Asn Ser Met Arg Ser Cys Phe Lys
                 20                  25                  30

Leu Thr Pro Phe Lys Ser Phe His Gly Val Asn Phe Asn Val Pro Ser
             35                  40                  45

Leu Ala Ala Ala Asn Cys Glu Ile Met Gly His Leu Lys Leu Gly Ser
         50                  55                  60

Leu Pro Tyr Lys Gln Cys Ser Val Ser Ser Lys Ser Thr Lys Thr Met
 65                  70                  75                  80

Ala Gln Leu Val Asp Leu Ala Glu Thr Glu Lys Ala Glu Gly Lys Asp
                 85                  90                  95

Ile Glu Phe Asp Phe Asn Glu Tyr Met Lys Ser Lys Ala Val Ala Val
            100                 105                 110

Asp Ala Ala Leu Asp Lys Ala Ile Pro Leu Glu Tyr Pro Glu Lys Ile
        115                 120                 125

His Glu Ser Met Arg Tyr Ser Leu Leu Ala Gly Gly Lys Arg Val Arg
    130                 135                 140

Pro Ala Leu Cys Ile Ala Ala Cys Glu Leu Val Gly Gly Ser Gln Asp
145                 150                 155                 160

Leu Ala Met Pro Thr Ala Cys Ala Met Glu Met Ile His Thr Met Ser
                165                 170                 175

Leu Ile His Asp Asp Leu Pro Cys Met Asp Asn Asp Asp Phe Arg Arg
            180                 185                 190

Gly Lys Pro Thr Asn His Lys Val Phe Gly Glu Asp Thr Ala Val Leu
        195                 200                 205

Ala Gly Asp Ala Leu Leu Ser Phe Ala Phe Glu His Ile Ala Val Ala
    210                 215                 220

Thr Ser Lys Thr Val Pro Ser Asp Arg Thr Leu Arg Val Ile Ser Glu
225                 230                 235                 240
```

```
Leu Gly Lys Thr Ile Gly Ser Gln Gly Leu Val Gly Gly Gln Val Val
                245                 250                 255

Asp Ile Thr Ser Glu Gly Asp Ala Asn Val Asp Leu Lys Thr Leu Glu
            260                 265                 270

Trp Ile His Ile His Lys Thr Ala Val Leu Leu Glu Cys Ser Val Val
        275                 280                 285

Ser Gly Gly Ile Leu Gly Gly Ala Thr Glu Asp Glu Ile Ala Arg Ile
    290                 295                 300

Arg Arg Tyr Ala Arg Cys Val Gly Leu Leu Phe Gln Val Val Asp Asp
305                 310                 315                 320

Ile Leu Asp Val Thr Lys Ser Ser Glu Glu Leu Gly Lys Thr Ala Gly
                325                 330                 335

Lys Asp Leu Leu Thr Asp Lys Ala Thr Tyr Pro Lys Leu Met Gly Leu
            340                 345                 350

Glu Lys Ala Lys Glu Phe Ala Ala Glu Leu Ala Thr Arg Ala Lys Glu
        355                 360                 365

Glu Leu Ser Ser Phe Asp Gln Ile Lys Ala Ala Pro Leu Leu Gly Leu
    370                 375                 380

Ala Asp Tyr Ile Ala Phe Arg Gln Asn
385                 390

<210> SEQ ID NO 28
<211> LENGTH: 393
<212> TYPE: PRT
<213> ORGANISM: Artificial Sequence
<220> FEATURE:
<223> OTHER INFORMATION: Description of Artificial Sequence: Taxus GGPP
      synthase protein variant
<220> FEATURE:
<221> NAME/KEY: VARIANT
<222> LOCATION: (1)..(393)
<223> OTHER INFORMATION: Computer-generated Taxus GGPP synthase protein
      variant

<400> SEQUENCE: 28

Met Ala Tyr Thr Ala Met Ala Ala Gly Thr Gln Ser Leu Gln Leu Arg
  1               5                  10                  15

Thr Val Ala Ser Tyr Gln Glu Cys Asn Ser Met Arg Ser Cys Phe Lys
                 20                  25                  30

Leu Thr Pro Phe Lys Ser Phe His Gly Val Asn Phe Asn Val Pro Ser
             35                  40                  45

Leu Gly Gly Ala Asn Cys Glu Ile Met Gly His Leu Lys Leu Gly Ser
         50                  55                  60

Leu Pro Tyr Lys Gln Cys Ser Val Ser Ser Lys Ser Thr Lys Thr Met
 65                  70                  75                  80

Ala Gln Leu Val Asp Leu Ala Glu Thr Glu Lys Ala Glu Gly Lys Asp
                 85                  90                  95

Ile Glu Phe Asp Phe Asn Glu Tyr Met Lys Ser Lys Ala Val Ala Val
            100                 105                 110

Asp Ala Ala Leu Asp Lys Ala Ile Pro Leu Glu Tyr Pro Glu Lys Ile
        115                 120                 125

His Glu Ser Met Arg Tyr Ser Leu Leu Ala Gly Gly Lys Arg Val Arg
    130                 135                 140

Pro Ala Leu Cys Ile Ala Ala Cys Glu Leu Val Gly Gly Ser Gln Asp
145                 150                 155                 160

Leu Ala Met Pro Thr Ala Cys Ala Met Glu Met Ile His Thr Met Ser
                165                 170                 175
```

```
Leu Ile His Asp Asp Leu Pro Cys Met Asp Asn Asp Asp Phe Arg Arg
            180                 185                 190

Gly Lys Pro Thr Asn His Lys Val Phe Gly Glu Asp Thr Ala Val Leu
            195                 200                 205

Ala Gly Asp Ala Leu Leu Ser Phe Ala Phe Glu His Ile Ala Val Ala
            210                 215                 220

Thr Ser Lys Thr Val Pro Ser Asp Arg Thr Leu Arg Val Ile Ser Glu
225                 230                 235                 240

Leu Gly Lys Thr Ile Gly Ser Gln Gly Leu Val Gly Gly Gln Val Val
            245                 250                 255

Asp Ile Thr Ser Glu Gly Asp Ala Asn Val Asp Leu Lys Thr Leu Glu
            260                 265                 270

Trp Ile His Ile His Lys Thr Ala Val Leu Leu Glu Cys Ser Val Val
            275                 280                 285

Ser Gly Gly Ile Leu Gly Gly Ala Thr Glu Asp Glu Ile Ala Arg Ile
            290                 295                 300

Arg Arg Tyr Ala Arg Cys Val Gly Leu Leu Phe Gln Val Val Asp Asp
305                 310                 315                 320

Ile Leu Asp Val Thr Lys Ser Ser Glu Glu Leu Gly Lys Thr Ala Gly
            325                 330                 335

Lys Asp Leu Leu Thr Asp Lys Ala Thr Tyr Pro Lys Leu Met Gly Leu
            340                 345                 350

Glu Lys Ala Lys Glu Phe Ala Ala Glu Leu Ala Thr Arg Ala Lys Glu
            355                 360                 365

Glu Leu Ser Ser Phe Asp Gln Ile Lys Ala Ala Pro Leu Leu Gly Leu
            370                 375                 380

Ala Asp Tyr Ile Ala Phe Arg Gln Asn
385                 390

<210> SEQ ID NO 29
<211> LENGTH: 393
<212> TYPE: PRT
<213> ORGANISM: Artificial Sequence
<220> FEATURE:
<223> OTHER INFORMATION: Description of Artificial Sequence: Taxus GGPP
      synthase protein variant
<220> FEATURE:
<221> NAME/KEY: VARIANT
<222> LOCATION: (1)..(393)
<223> OTHER INFORMATION: Computer-generated Taxus GGPP synthase protein
      variant

<400> SEQUENCE: 29

Met Ala Tyr Thr Ala Met Ala Ala Gly Thr Gln Ser Leu Gln Leu Arg
1               5                   10                  15

Thr Val Ala Ser Tyr Gln Glu Cys Asn Ser Met Arg Ser Cys Phe Lys
            20                  25                  30

Leu Thr Pro Phe Lys Ser Phe His Gly Val Asn Phe Asn Val Pro Ser
            35                  40                  45

Leu Gly Ala Ala Asn Cys Asp Ile Met Gly His Leu Lys Leu Gly Ser
            50                  55                  60

Leu Pro Tyr Lys Gln Cys Ser Val Ser Ser Lys Ser Thr Lys Thr Met
65                  70                  75                  80

Ala Gln Leu Val Asp Leu Ala Glu Thr Glu Lys Ala Glu Gly Lys Asp
            85                  90                  95

Ile Glu Phe Asp Phe Asn Glu Tyr Met Lys Ser Lys Ala Val Ala Val
            100                 105                 110
```

```
Asp Ala Ala Leu Asp Lys Ala Ile Pro Leu Glu Tyr Pro Glu Lys Ile
            115                 120                 125

His Glu Ser Met Arg Tyr Ser Leu Leu Ala Gly Gly Lys Arg Val Arg
130                 135                 140

Pro Ala Leu Cys Ile Ala Ala Cys Glu Leu Val Gly Gly Ser Gln Asp
145                 150                 155                 160

Leu Ala Met Pro Thr Ala Cys Ala Met Glu Met Ile His Thr Met Ser
                165                 170                 175

Leu Ile His Asp Asp Leu Pro Cys Met Asp Asn Asp Asp Phe Arg Arg
            180                 185                 190

Gly Lys Pro Thr Asn His Lys Val Phe Gly Glu Asp Thr Ala Val Leu
        195                 200                 205

Ala Gly Asp Ala Leu Leu Ser Phe Ala Phe Glu His Ile Ala Val Ala
    210                 215                 220

Thr Ser Lys Thr Val Pro Ser Asp Arg Thr Leu Arg Val Ile Ser Glu
225                 230                 235                 240

Leu Gly Lys Thr Ile Gly Ser Gln Gly Leu Val Gly Gly Gln Val Val
                245                 250                 255

Asp Ile Thr Ser Glu Gly Asp Ala Asn Val Asp Leu Lys Thr Leu Glu
            260                 265                 270

Trp Ile His Ile His Lys Thr Ala Val Leu Leu Glu Cys Ser Val Val
        275                 280                 285

Ser Gly Gly Ile Leu Gly Gly Ala Thr Glu Asp Glu Ile Ala Arg Ile
    290                 295                 300

Arg Arg Tyr Ala Arg Cys Val Gly Leu Leu Phe Gln Val Val Asp Asp
305                 310                 315                 320

Ile Leu Asp Val Thr Lys Ser Ser Glu Glu Leu Gly Lys Thr Ala Gly
                325                 330                 335

Lys Asp Leu Leu Thr Asp Lys Ala Thr Tyr Pro Lys Leu Met Gly Leu
            340                 345                 350

Glu Lys Ala Lys Glu Phe Ala Ala Glu Leu Ala Thr Arg Ala Lys Glu
        355                 360                 365

Glu Leu Ser Ser Phe Asp Gln Ile Lys Ala Ala Pro Leu Leu Gly Leu
    370                 375                 380

Ala Asp Tyr Ile Ala Phe Arg Gln Asn
385                 390

<210> SEQ ID NO 30
<211> LENGTH: 393
<212> TYPE: PRT
<213> ORGANISM: Artificial Sequence
<220> FEATURE:
<223> OTHER INFORMATION: Description of Artificial Sequence: Taxus GGPP
      synthase protein variant
<220> FEATURE:
<221> NAME/KEY: VARIANT
<222> LOCATION: (1)..(393)
<223> OTHER INFORMATION: Computer-generated Taxus GGPP synthase protein
      variant

<400> SEQUENCE: 30

Met Ala Tyr Thr Ala Met Ala Ala Gly Thr Gln Ser Leu Gln Leu Arg
1               5                   10                  15

Thr Val Ala Ser Tyr Gln Glu Cys Asn Ser Met Arg Ser Cys Phe Lys
            20                  25                  30

Leu Thr Pro Phe Lys Ser Phe His Gly Val Asn Phe Asn Val Pro Ser
        35                  40                  45
```

```
Leu Gly Ala Ala Asn Cys Glu Ile Met Ala His Leu Lys Leu Gly Ser
         50                  55                  60

Leu Pro Tyr Lys Gln Cys Ser Val Ser Ser Lys Ser Thr Lys Thr Met
 65                  70                  75                  80

Ala Gln Leu Val Asp Leu Ala Glu Thr Glu Lys Ala Glu Gly Lys Asp
                 85                  90                  95

Ile Glu Phe Asp Phe Asn Glu Tyr Met Lys Ser Lys Ala Val Ala Val
             100                 105                 110

Asp Ala Ala Leu Asp Lys Ala Ile Pro Leu Glu Tyr Pro Glu Lys Ile
         115                 120                 125

His Glu Ser Met Arg Tyr Ser Leu Leu Ala Gly Gly Lys Arg Val Arg
     130                 135                 140

Pro Ala Leu Cys Ile Ala Ala Cys Glu Leu Val Gly Gly Ser Gln Asp
145                 150                 155                 160

Leu Ala Met Pro Thr Ala Cys Ala Met Glu Met Ile His Thr Met Ser
                165                 170                 175

Leu Ile His Asp Asp Leu Pro Cys Met Asp Asn Asp Asp Phe Arg Arg
            180                 185                 190

Gly Lys Pro Thr Asn His Lys Val Phe Gly Glu Asp Thr Ala Val Leu
        195                 200                 205

Ala Gly Asp Ala Leu Leu Ser Phe Ala Phe Glu His Ile Ala Val Ala
    210                 215                 220

Thr Ser Lys Thr Val Pro Ser Asp Arg Thr Leu Arg Val Ile Ser Glu
225                 230                 235                 240

Leu Gly Lys Thr Ile Gly Ser Gln Gly Leu Val Gly Gly Gln Val Val
                245                 250                 255

Asp Ile Thr Ser Glu Gly Asp Ala Asn Val Asp Leu Lys Thr Leu Glu
            260                 265                 270

Trp Ile His Ile His Lys Thr Ala Val Leu Leu Glu Cys Ser Val Val
        275                 280                 285

Ser Gly Gly Ile Leu Gly Gly Ala Thr Glu Asp Glu Ile Ala Arg Ile
    290                 295                 300

Arg Arg Tyr Ala Arg Cys Val Gly Leu Leu Phe Gln Val Val Asp Asp
305                 310                 315                 320

Ile Leu Asp Val Thr Lys Ser Ser Glu Glu Leu Gly Lys Thr Ala Gly
                325                 330                 335

Lys Asp Leu Leu Thr Asp Lys Ala Thr Tyr Pro Lys Leu Met Gly Leu
            340                 345                 350

Glu Lys Ala Lys Glu Phe Ala Ala Glu Leu Ala Thr Arg Ala Lys Glu
        355                 360                 365

Glu Leu Ser Ser Phe Asp Gln Ile Lys Ala Ala Pro Leu Leu Gly Leu
    370                 375                 380

Ala Asp Tyr Ile Ala Phe Arg Gln Asn
385                 390

<210> SEQ ID NO 31
<211> LENGTH: 393
<212> TYPE: PRT
<213> ORGANISM: Artificial Sequence
<220> FEATURE:
<223> OTHER INFORMATION: Description of Artificial Sequence:  GGPP
      synthase protein variant
<220> FEATURE:
<221> NAME/KEY: VARIANT
<222> LOCATION: (1)..(393)
<223> OTHER INFORMATION: Computer-generated Taxus GGPP synthase protein
      variant
```

<400> SEQUENCE: 31

```
Met Ala Tyr Thr Ala Met Ala Ala Gly Thr Gln Ser Leu Gln Leu Arg
 1               5                  10                  15

Thr Val Ala Ser Tyr Gln Glu Cys Asn Ser Met Arg Ser Cys Phe Lys
                20                  25                  30

Leu Thr Pro Phe Lys Ser Phe His Gly Val Asn Phe Asn Val Pro Ser
             35                  40                  45

Leu Gly Ala Ala Asn Cys Glu Ile Met Gly His Leu Arg Leu Gly Ser
         50                  55                  60

Leu Pro Tyr Lys Gln Cys Ser Val Ser Ser Lys Ser Thr Lys Thr Met
 65                  70                  75                  80

Ala Gln Leu Val Asp Leu Ala Glu Thr Glu Lys Ala Glu Gly Lys Asp
                 85                  90                  95

Ile Glu Phe Asp Phe Asn Glu Tyr Met Lys Ser Lys Ala Val Ala Val
                100                 105                 110

Asp Ala Ala Leu Asp Lys Ala Ile Pro Leu Glu Tyr Pro Glu Lys Ile
            115                 120                 125

His Glu Ser Met Arg Tyr Ser Leu Leu Ala Gly Gly Lys Arg Val Arg
        130                 135                 140

Pro Ala Leu Cys Ile Ala Ala Cys Glu Leu Val Gly Gly Ser Gln Asp
145                 150                 155                 160

Leu Ala Met Pro Thr Ala Cys Ala Met Glu Met Ile His Thr Met Ser
                165                 170                 175

Leu Ile His Asp Asp Leu Pro Cys Met Asp Asn Asp Asp Phe Arg Arg
                180                 185                 190

Gly Lys Pro Thr Asn His Lys Val Phe Gly Glu Asp Thr Ala Val Leu
            195                 200                 205

Ala Gly Asp Ala Leu Leu Ser Phe Ala Phe Glu His Ile Ala Val Ala
        210                 215                 220

Thr Ser Lys Thr Val Pro Ser Asp Arg Thr Leu Arg Val Ile Ser Glu
225                 230                 235                 240

Leu Gly Lys Thr Ile Gly Ser Gln Gly Leu Val Gly Gly Gln Val Val
                245                 250                 255

Asp Ile Thr Ser Glu Gly Asp Ala Asn Val Asp Leu Lys Thr Leu Glu
                260                 265                 270

Trp Ile His Ile His Lys Thr Ala Val Leu Leu Glu Cys Ser Val Val
            275                 280                 285

Ser Gly Gly Ile Leu Gly Gly Ala Thr Glu Asp Glu Ile Ala Arg Ile
        290                 295                 300

Arg Arg Tyr Ala Arg Cys Val Gly Leu Leu Phe Gln Val Val Asp Asp
305                 310                 315                 320

Ile Leu Asp Val Thr Lys Ser Ser Glu Glu Leu Gly Lys Thr Ala Gly
                325                 330                 335

Lys Asp Leu Leu Thr Asp Lys Ala Thr Tyr Pro Lys Leu Met Gly Leu
            340                 345                 350

Glu Lys Ala Lys Glu Phe Ala Ala Glu Leu Ala Thr Arg Ala Lys Glu
        355                 360                 365

Glu Leu Ser Ser Phe Asp Gln Ile Lys Ala Ala Pro Leu Leu Gly Leu
    370                 375                 380

Ala Asp Tyr Ile Ala Phe Arg Gln Asn
385                 390
```

-continued

```
<210> SEQ ID NO 32
<211> LENGTH: 393
<212> TYPE: PRT
<213> ORGANISM: Artificial Sequence
<220> FEATURE:
<223> OTHER INFORMATION: Description of Artificial Sequence: variant of
      Taxus GGPP synthase protein
<220> FEATURE:
<221> NAME/KEY: VARIANT
<222> LOCATION: (1)..(393)
<223> OTHER INFORMATION: Computer-generated variant of Taxus GGPP
      synthase protein

<400> SEQUENCE: 32

Met Ala Tyr Thr Ala Met Ala Ala Gly Thr Gln Ser Leu Gln Leu Arg
  1               5                  10                  15

Thr Val Ala Ser Tyr Gln Glu Cys Asn Ser Met Arg Ser Cys Phe Lys
                 20                  25                  30

Leu Thr Pro Phe Lys Ser Phe His Gly Val Asn Phe Asn Val Pro Ser
             35                  40                  45

Leu Gly Ala Ala Asn Cys Glu Ile Met Gly His Leu Lys Leu Gly Ser
 50                  55                  60

Leu Pro Tyr Lys Gln Cys Ser Val Ser Ser Arg Ser Thr Lys Thr Met
 65                  70                  75                  80

Ala Gln Leu Val Asp Leu Ala Glu Thr Glu Lys Ala Glu Gly Lys Asp
                 85                  90                  95

Ile Glu Phe Asp Phe Asn Glu Tyr Met Lys Ser Lys Ala Val Ala Val
            100                 105                 110

Asp Ala Ala Leu Asp Lys Ala Ile Pro Leu Glu Tyr Pro Glu Lys Ile
            115                 120                 125

His Glu Ser Met Arg Tyr Ser Leu Leu Ala Gly Gly Lys Arg Val Arg
130                 135                 140

Pro Ala Leu Cys Ile Ala Ala Cys Glu Leu Val Gly Gly Ser Gln Asp
145                 150                 155                 160

Leu Ala Met Pro Thr Ala Cys Ala Met Glu Met Ile His Thr Met Ser
                165                 170                 175

Leu Ile His Asp Asp Leu Pro Cys Met Asp Asn Asp Asp Phe Arg Arg
            180                 185                 190

Gly Lys Pro Thr Asn His Lys Val Phe Gly Glu Asp Thr Ala Val Leu
            195                 200                 205

Ala Gly Asp Ala Leu Leu Ser Phe Ala Phe Glu His Ile Ala Val Ala
210                 215                 220

Thr Ser Lys Thr Val Pro Ser Asp Arg Thr Leu Arg Val Ile Ser Glu
225                 230                 235                 240

Leu Gly Lys Thr Ile Gly Ser Gln Gly Leu Val Gly Gln Val Val
                245                 250                 255

Asp Ile Thr Ser Glu Gly Asp Ala Asn Val Asp Leu Lys Thr Leu Glu
            260                 265                 270

Trp Ile His Ile His Lys Thr Ala Val Leu Leu Glu Cys Ser Val Val
            275                 280                 285

Ser Gly Gly Ile Leu Gly Gly Ala Thr Glu Asp Glu Ile Ala Arg Ile
290                 295                 300

Arg Arg Tyr Ala Arg Cys Val Gly Leu Leu Phe Gln Val Val Asp Asp
305                 310                 315                 320

Ile Leu Asp Val Thr Lys Ser Ser Glu Glu Leu Gly Lys Thr Ala Gly
                325                 330                 335
```

```
Lys Asp Leu Leu Thr Asp Lys Ala Thr Tyr Pro Lys Leu Met Gly Leu
            340                 345                 350

Glu Lys Ala Lys Glu Phe Ala Ala Glu Leu Ala Thr Arg Ala Lys Glu
            355                 360                 365

Glu Leu Ser Ser Phe Asp Gln Ile Lys Ala Ala Pro Leu Leu Gly Leu
            370                 375                 380

Ala Asp Tyr Ile Ala Phe Arg Gln Asn
385                 390

<210> SEQ ID NO 33
<211> LENGTH: 393
<212> TYPE: PRT
<213> ORGANISM: Artificial Sequence
<220> FEATURE:
<223> OTHER INFORMATION: Description of Artificial Sequence: Taxus GGPP
      synthase protein variant
<220> FEATURE:
<221> NAME/KEY: VARIANT
<222> LOCATION: (1)..(393)
<223> OTHER INFORMATION: Computer-generated Taxus GGPP synthase variant

<400> SEQUENCE: 33

Met Ala Tyr Thr Ala Met Ala Ala Gly Thr Gln Ser Leu Gln Leu Arg
  1               5                  10                  15

Thr Val Ala Ser Tyr Gln Glu Cys Asn Ser Met Arg Ser Cys Phe Lys
             20                  25                  30

Leu Thr Pro Phe Lys Ser Phe His Gly Val Asn Phe Asn Val Pro Ser
         35                  40                  45

Leu Gly Ala Ala Asn Cys Glu Ile Met Gly His Leu Lys Leu Gly Ser
     50                  55                  60

Leu Pro Tyr Lys Gln Cys Ser Val Ser Ser Arg Ser Thr Lys Thr Met
 65                  70                  75                  80

Ala Gln Leu Val Asp Leu Ala Glu Thr Glu Lys Ala Glu Gly Lys Asp
                 85                  90                  95

Ile Glu Phe Asp Phe Asn Glu Tyr Met Lys Ser Lys Ala Val Ala Val
            100                 105                 110

Asp Ala Ala Leu Asp Lys Ala Ile Pro Leu Glu Tyr Pro Glu Lys Ile
        115                 120                 125

His Glu Ser Met Arg Tyr Ser Leu Leu Ala Gly Gly Lys Arg Val Arg
    130                 135                 140

Pro Ala Leu Cys Ile Ala Ala Cys Glu Leu Val Gly Gly Ser Gln Asp
145                 150                 155                 160

Leu Ala Met Pro Thr Ala Cys Ala Met Glu Met Ile His Thr Met Ser
                165                 170                 175

Leu Ile His Asp Asp Leu Pro Cys Met Asp Asn Asp Phe Arg Arg
            180                 185                 190

Gly Lys Pro Thr Asn His Lys Val Phe Gly Glu Asp Thr Ala Val Leu
        195                 200                 205

Ala Gly Asp Ala Leu Leu Ser Phe Ala Phe Glu His Ile Ala Val Ala
    210                 215                 220

Thr Ser Lys Thr Val Pro Ser Asp Arg Thr Leu Arg Val Ile Ser Glu
225                 230                 235                 240

Leu Gly Lys Thr Ile Gly Ser Gln Gly Leu Val Gly Gly Gln Val Val
                245                 250                 255

Asp Ile Thr Ser Glu Gly Asp Ala Asn Val Asp Leu Lys Thr Leu Glu
            260                 265                 270
```

```
Trp Ile His Ile His Lys Thr Ala Val Leu Leu Glu Cys Ser Val Val
            275                 280                 285

Ser Gly Gly Ile Leu Gly Gly Ala Thr Glu Asp Glu Ile Ala Arg Ile
        290                 295                 300

Arg Arg Tyr Ala Arg Cys Val Gly Leu Leu Phe Gln Val Val Asp Asp
305                 310                 315                 320

Ile Leu Asp Val Thr Lys Ser Ser Glu Glu Leu Gly Lys Thr Ala Gly
                325                 330                 335

Lys Asp Leu Leu Thr Asp Lys Ala Thr Tyr Pro Lys Leu Met Gly Leu
            340                 345                 350

Glu Lys Ala Lys Glu Phe Ala Ala Glu Leu Ala Thr Arg Ala Lys Glu
        355                 360                 365

Glu Leu Ser Ser Phe Asp Gln Ile Lys Ala Ala Pro Leu Leu Gly Leu
    370                 375                 380

Ala Asp Tyr Ile Ala Phe Arg Gln Asn
385                 390

<210> SEQ ID NO 34
<211> LENGTH: 393
<212> TYPE: PRT
<213> ORGANISM: Artificial Sequence
<220> FEATURE:
<223> OTHER INFORMATION: Description of Artificial Sequence: Taxus GGPP
      synthase protein variant
<220> FEATURE:
<221> NAME/KEY: VARIANT
<222> LOCATION: (1)..(393)
<223> OTHER INFORMATION: Computer-generated Taxus GGPP synthase protein
      variant

<400> SEQUENCE: 34

Met Ala Tyr Thr Ala Met Ala Ala Gly Thr Gln Ser Leu Gln Leu Arg
  1               5                  10                  15

Thr Val Ala Ser Tyr Gln Glu Cys Asn Ser Met Arg Ser Cys Phe Lys
                20                  25                  30

Leu Thr Pro Phe Lys Ser Phe His Gly Val Asn Phe Asn Val Pro Ser
            35                  40                  45

Leu Gly Ala Ala Asn Cys Glu Ile Met Gly His Leu Lys Leu Gly Ser
        50                  55                  60

Leu Pro Tyr Lys Gln Cys Ser Val Ser Ser Lys Ser Thr Lys Thr Met
65                  70                  75                  80

Gly Gln Leu Val Asp Leu Ala Glu Thr Glu Lys Ala Glu Gly Lys Asp
                85                  90                  95

Ile Glu Phe Asp Phe Asn Glu Tyr Met Lys Ser Lys Ala Val Ala Val
            100                 105                 110

Asp Ala Ala Leu Asp Lys Ala Ile Pro Leu Glu Tyr Pro Glu Lys Ile
        115                 120                 125

His Glu Ser Met Arg Tyr Ser Leu Leu Ala Gly Gly Lys Arg Val Arg
    130                 135                 140

Pro Ala Leu Cys Ile Ala Ala Cys Glu Leu Val Gly Gly Ser Gln Asp
145                 150                 155                 160

Leu Ala Met Pro Thr Ala Cys Ala Met Glu Met Ile His Thr Met Ser
                165                 170                 175

Leu Ile His Asp Asp Leu Pro Cys Met Asp Asn Asp Asp Phe Arg Arg
            180                 185                 190

Gly Lys Pro Thr Asn His Lys Val Phe Gly Glu Asp Thr Ala Val Leu
        195                 200                 205
```

-continued

```
Ala Gly Asp Ala Leu Leu Ser Phe Ala Phe Glu His Ile Ala Val Ala
    210                 215                 220

Thr Ser Lys Thr Val Pro Ser Asp Arg Thr Leu Arg Val Ile Ser Glu
225                 230                 235                 240

Leu Gly Lys Thr Ile Gly Ser Gln Gly Leu Val Gly Gly Gln Val Val
                245                 250                 255

Asp Ile Thr Ser Glu Gly Asp Ala Asn Val Asp Leu Lys Thr Leu Glu
            260                 265                 270

Trp Ile His Ile His Lys Thr Ala Val Leu Leu Glu Cys Ser Val Val
        275                 280                 285

Ser Gly Gly Ile Leu Gly Gly Ala Thr Glu Asp Glu Ile Ala Arg Ile
    290                 295                 300

Arg Arg Tyr Ala Arg Cys Val Gly Leu Leu Phe Gln Val Val Asp Asp
305                 310                 315                 320

Ile Leu Asp Val Thr Lys Ser Ser Glu Glu Leu Gly Lys Thr Ala Gly
                325                 330                 335

Lys Asp Leu Leu Thr Asp Lys Ala Thr Tyr Pro Lys Leu Met Gly Leu
                340                 345                 350

Glu Lys Ala Lys Glu Phe Ala Ala Glu Leu Ala Thr Arg Ala Lys Glu
            355                 360                 365

Glu Leu Ser Ser Phe Asp Gln Ile Lys Ala Ala Pro Leu Leu Gly Leu
    370                 375                 380

Ala Asp Tyr Ile Ala Phe Arg Gln Asn
385                 390
```